(12) United States Patent
Lefker et al.

(10) Patent No.: US 7,507,732 B2
(45) Date of Patent: Mar. 24, 2009

(54) CYCLOPENTAPYRIDINE AND TETRAHYDROQUINOLINE DERIVATIVES

(75) Inventors: Bruce A. Lefker, Gales Ferry, CT (US); Kevin K. -C. Liu, East Lyme, CT (US); Hou Chen, Salem, CT (US); Steven Blair Coffey, Pawcatuck, CT (US)

(73) Assignee: Pfizer Inc., New York, NY (US)

(*) Notice: Subject to any disclaimer, the term of this patent is extended or adjusted under 35 U.S.C. 154(b) by 278 days.

(21) Appl. No.: 11/395,327

(22) Filed: Mar. 31, 2006

(65) Prior Publication Data

US 2006/0247254 A1 Nov. 2, 2006

Related U.S. Application Data

(60) Provisional application No. 60/762,159, filed on Jan. 26, 2006, provisional application No. 60/667,184, filed on Mar. 31, 2005.

(51) Int. Cl.
- *A61K 31/5377* (2006.01)
- *A61K 31/506* (2006.01)
- *A61K 31/496* (2006.01)
- *C07D 215/38* (2006.01)
- *C07D 221/04* (2006.01)
- *C07D 319/08* (2006.01)
- *C07D 413/12* (2006.01)
- *C07D 401/12* (2006.01)
- *C07D 403/12* (2006.01)

(52) U.S. Cl. ............... 514/235.2; 514/252.18; 514/253.04; 514/253.06; 544/121; 544/295; 544/362; 544/363

(58) Field of Classification Search ............... None
See application file for complete search history.

(56) References Cited

U.S. PATENT DOCUMENTS

| | | | |
|---|---|---|---|
| 4,985,352 A | 1/1991 | Julius et al. |
| 5,626,791 A | 5/1997 | Fenkl et al. |
| 5,698,766 A | 12/1997 | Julius et al. |
| 6,040,448 A | 3/2000 | Greenlee et al. |
| 6,331,629 B1 | 12/2001 | Greenlee et al. |
| 6,380,238 B1 | 4/2002 | Adams et al. |
| 6,384,224 B2 | 5/2002 | Greenlee et al. |
| 6,953,787 B2 | 10/2005 | Smith et al. |
| 2002/0013317 A1 | 1/2002 | Greenlee et al. |
| 2002/0014720 A1 | 2/2002 | Sicilia et al. |
| 2003/0105106 A1 | 6/2003 | Chiang et al. |
| 2004/0209902 A1 | 10/2004 | Lin et al. |

FOREIGN PATENT DOCUMENTS

| EP | 361489 | 4/1990 |
|---|---|---|
| EP | 0385237 | 9/1990 |
| EP | 0572863 | 12/1993 |
| EP | 0655440 | 5/1995 |
| EP | 657426 | 6/1995 |
| EP | 863136 | 9/1998 |
| JP | 01211581 | 8/1989 |
| JP | 04066571 | 3/1992 |
| JP | 04103572 | 4/1992 |
| JP | 00191533 | 7/2000 |
| WO | WO9808846 | 3/1998 |
| WO | WO9830548 | 7/1998 |
| WO | WO9921850 | 5/1999 |
| WO | WO9943647 | 9/1999 |
| WO | WO9958490 | 11/1999 |
| WO | WO0012077 | 3/2000 |
| WO | WO0012475 | 3/2000 |
| WO | WO0012482 | 3/2000 |
| WO | WO0012502 | 3/2000 |
| WO | WO0012510 | 3/2000 |
| WO | WO0028993 | 5/2000 |
| WO | WO0044737 | 8/2000 |
| WO | WO0076984 | 12/2000 |
| WO | WO0240456 | 5/2002 |
| WO | WO0270509 | 9/2002 |
| WO | WO0281443 | 10/2002 |
| WO | WO03000663 | 1/2003 |
| WO | WO03000666 | 1/2003 |
| WO | WO2004/108682 | 12/2004 |
| WO | WO2006015263 | 2/2006 |

OTHER PUBLICATIONS

Gaster et al. Annual Reports in Medicinal Chemistry, vol. 33, p. 21-30 (1998).*
Isaac et al. Bioorganic & Medicinal Chemistry letters, vol. 10, p. 919-921 (2000).*
Nitsch et al. J. Biol. Chem. vol. 271, p. 4188-4194 (1996).*

(Continued)

*Primary Examiner*—Emily Bernhardt
(74) *Attorney, Agent, or Firm*—Gregg C. Benson; Arlene K. Musser

(57) ABSTRACT

6,7-Dihydro-5H-cyclopenta[b]pyridine and 5,6,7,8-tetrahydroquinoline compounds of Formula (I), including salts, hydrates and solvates thereof, that act as 5-$HT_2$ receptor ligands and their uses in the treatment of diseases linked to the activation of 5-$HT_{2c}$ receptors are described herein.

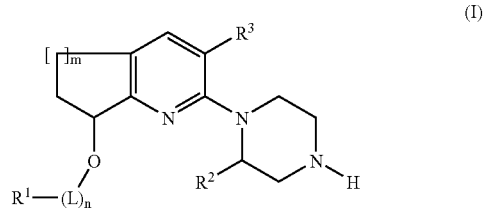

(I)

34 Claims, No Drawings

OTHER PUBLICATIONS

Vippagunta et al. Advanced Drug Delivery Reviews, vol. 48, pp. 3-26 (2001).*

M. J. Bishop and B. M. Nilson: New 5-HT2c receptor agonists, Expert Opin. Ther. Patents, vol. 13, No. 11, 2003, pp. 1691-1705.

J. Ruble, et al., Enantioselective Construction of Quaternary Stereocenters: Rearrangements of O-Acylated Azlactones Catalyzed by a Planar-Chiral Derivative of 4-(Pyrrolidino)pyridine, J. Amer. Chem. Soc., vol. 120 (44), 1998, pp. 11532-11533.

S. Rosenzweig-Lipson, et al., Poster at the Society for Neuroscience 34th Annual Meeting, San Diego; Society for Neuroscience Abstracts 2004 (Abs 394.6).

S. Grauer., et al., Poster at the Society for Neuroscience 34th Annual Meeting, San Diego, 2004; Society for Neuroscience Abstracts, 2004 (Abs 394.7).

J. Dunlop, et al, Poster at the Society for Neuroscience 34th Annual Meeting; Society for Neuroscience Abstracts 2004 (Abs 394.10).

* cited by examiner

CYCLOPENTAPYRIDINE AND TETRAHYDROQUINOLINE DERIVATIVES

This application claims the benefit of U.S. Provisional Application Ser. No. 60/762,159 filed on Jan. 26, 2006, U.S. Provisional Application Ser. No. 60/667,184 filed on Mar. 31, 2005.

FIELD OF THE INVENTION

The present invention relates to 6,7-dihydro-5H-cyclopenta[b]pyridine and 5,6,7,8-tetrahydroquinoline derivatives. The compounds have been found to act as 5-HT receptor ligands, in particular $5\text{-}HT_{2c}$ receptor agonists; therefore, the present invention also relates to their uses in the treatment of diseases linked to the activation of the $5\text{-}HT_{2c}$ receptor in animals.

BACKGROUND

Receptors for serotonin (5-hydroxytryptamine, 5-HT) are an important class of G protein-coupled receptors. Serotonin is thought to play a role in processes related to learning and memory, sleep, thermoregulation, mood, motor activity, pain, sexual and aggressive behaviors, appetite, neurodegenerative regulation, and biological rhythms. As expected, serotonin is linked to pathophysiological conditions such as anxiety, depression, obsessive-compulsive disorders, schizophrenia, suicide, autism, migraine, emesis, alcoholism and neurodegenerative disorders.

The serotonin receptors are currently classified into seven subfamilies ($5\text{-}HT_1$ through $5\text{-}HT_7$). See, Hoyer, D., et al., "VII International Union of Pharmacology classification of receptors for 5-hydroxytryptamine", *Pharmacol. Rev.*, 56, 157-203 (1994). The subfamilies have been further divided into subtypes. For example, the $5\text{-}HT_2$ receptor is currently divided into three subtypes: $5\text{-}HT_{2a}$, $5\text{-}HT_{2b}$ and $5\text{-}HT_{2c}$. These $5\text{-}HT_2$ receptor subtypes are linked to phospholipase C with the generation of two second messengers, diacylglycerol (which activates protein kinase C) and inositol trisphosphate (which releases intracellular stores of $Ca^{2+}$). The choroid plexus, an epithelial tissue that is the primary site of cerebrospinal fluid production, contains very high density $5\text{-}HT_{2c}$ receptors. See, Sanders-Bush, E. and S. E. Mayer, "5-Hydroxytryptamine (Serotonin) Receptor agonists and Antagonists", *Goodman & Gilman's The Pharmacological Basis of Therapeutics*, Chapter 11, 9th Ed., McGraw-Hill, New York, N.Y. (1996).

Bishop, M. J. and Nilsson, B. M., "New $5\text{-}HT_{2c}$ Receptor Agonists" Expert Opin. Ther. Patents, 2003, 13(11): 1691-1705, review patent applications that describe compounds having agonist activity at the $5\text{-}HT_{2c}$ receptor. The review also addresses indications for which evidence exists to support the use of $5\text{-}HT_{2c}$ agonists in their treatment, such as obesity, schizophrenia, anxiety, depression, obsessive-compulsive disorder, sexual dysfunction, epilepsy, and urinary incontinence, among others.

Julius, et al., isolated and characterized the $5\text{-}HT_{2c}$ receptor and later reported that transgenic mice lacking the $5\text{-}HT_{2c}$ receptor exhibit seizures and an eating disorder resulting in increased consumption of food (see, U.S. Pat. Nos. 4,985,352 and 5,698,766, respectively). Consequently, compounds selective for the $5\text{-}HT_{2c}$ receptor may provide useful therapies for the treatment of seizure and eating disorders without the side effects typically associated with nonselectivity of the ligand.

Several compounds have been proposed as $5\text{-}HT_{2c}$ receptor agonists or antagonists for use in the treatment of obesity and other related diseases associated with decreased neurotransmission of serotonin in mammals. See, e.g., EP 863136 (azetidine and pyrrolidine derivatives); EP 657426 (tricyclic pyrrole derivatives); EP 655440 (substituted 1-aminoethyl indoles); EP 572863 (pyrazinoindole derivatives); WO98/030548 (aminoalkylindazole compounds); WO 98/56768 (tricyclic pyrrole and pyrazole derivatives); WO 99/43647 (azetidine and pyrrolidine derivatives); WO 99/58490 (arylhydronaphthalenalkanamine derivatives); WO 00/12475 (indoline derivatives); WO 00/12482 (indazole derivatives); WO 00/12502 (pyrroloquinoline derivatives); WO 00/12510 (pyrroloindole, pyridoindole and azepinoindole derivatives); WO 00/28993 (naphthylacetylpiperazine derivatives); WO 00/44737 (aminoalkylbenzofuran derivatives); WO 00/76984 (2,3-disubstituted pyrazines); US Publication No. 2002/0147200 A1 or WO 02/40456 (pyrazine, pyridine, and pyrimidine derivatives); WO 03/000666 (pyrazine derivatives); and US Publication No. 2003/0105106 A1 or WO 03/000663 (pyrimidine derivatives). For a review of obesity medications, see A. Halpern and M. C. Mancini, "Treatment of obesity: an update on anti-obesity medications," *Obesity Reviews*, 4, 2542 (2003).

Schizophrenia is a complex multifactorial illness caused by genetic and non-genetic risk factors that produce a wide variety of symptoms. Historically, the disease has been characterized by positive and negative symptoms. The positive symptoms include delusions and hallucinations and the negative symptoms include apathy, withdrawal, lack of motivation and pleasure. More recently, deficits in affect, attention, cognition and information processing have been recognized as key pathologies in this complex disorder. No single biological element has emerged as a dominant pathogenic factor in this disease. It is likely that schizophrenia is a syndrome that is produced by the combination of many low penetrance risk factors. The symptoms of schizophrenia, however, are correlated with enhanced dopamine neurotransmission in the mesolimbic system.

A $5\text{-}HT_{2c}$ agonist was shown to have activity in pre-clinical models of depression (rat forced swim test, learned helplessness, olfactory bulbectomy model, resident-intruder model). Antidepressant-like Effects of the $5\text{-}HT_{2c}$ Selective Agonist WAY-163909 in Rodents. Rosenzweig-Lipson S., et al., Poster at the Society for Neuroscience 34th Annual Meeting, San Diego, 2004; *Society for Neuroscience Abstracts* 2004, 34: San Diego (Abs 394.6). $5\text{-}HT_{2c}$ agonists may improve the negative symptoms and apathy associated with schizophrenia. The selective $5\text{-}HT_{2c}$ agonist of Rosenzweig-Lipson S., et al. has also been reported to exhibit an atypical antipsychotic-like profile in rodent behavioral models. WAY-163909, A $5\text{-}HT_{2c}$ Agonist, Exhibits an Atypical Antipsychotic-Like Profile in a Battery of Rodent Behavioral Models. Grauer, S., et al., Poster at the Society for Neuroscience 34th Annual Meeting, San Diego, 2004; *Society for Neuroscience Abstracts*, 2004, San Diego (Abs 394.7). A rationale for the treatment of schizophrenia recognizes that $5\text{-}HT_{2c}$ agonists selectively decrease firing and release of dopamine in the mesolimbic dopaminergic pathway. Grauer, S., et al., supra.

It is notable that the $5\text{-}HT_{2c}$ agonist studied by Rosenzweig-Lipson S., et al. and Grauer, S., et al., supra, is reported to produce a dose-dependent reduction of food intake in rats. Pharmacological Characterization of WAY-163909, a Novel 5-HT2c Receptor Selective Agonist. Dunlop, J., et al., Poster at the Society for Neuroscience 34th Annual Meeting, San Diego, 2004; *Society for Neuroscience Abstracts* 2004, San Diego (Abs 394.10).

Toxicity and non-selectivity of ligands for the various 5-HT receptors remain a challenge. It is suspected that the non-selectivity of some ligands contributes to various adverse side effects such as hallucinations and cardiovascular complications. Therefore, there remains a need for 5-HT$_{2c}$ selective receptor ligands.

SUMMARY

The present invention provides compounds of the Formula:

wherein;

m is 1 or 2;

n is 0 or 1;

L is —CHR$^{0a}$—, where R$^{0a}$ is hydrogen or (C$_1$-C$_4$)alkyl;

R$^2$ is hydrogen or methyl;

R$^3$ is selected from the group consisting of H, Cl, Br, F, CH$_3$ and CN;

R$^1$ is (a) a group of Formula (1A)

where (i) p, r and s are each independently 0 or 1, and

R$^{1a}$, R$^{1b}$ and R$^{1c}$ are each independently selected from the group consisting of F, Cl, Br, I, cyano, —CH$_2$—CN, —NH$_2$, —OH, (C$_1$-C$_6$)alkyl, (C$_1$-C$_6$)alkoxy, (C$_1$-C$_4$)alkylthio, fluoro-substituted (C$_1$-C$_4$)alkyl, fluoro-substituted (C$_1$-C$_4$)alkoxy, fluoro-substituted (C$_1$-C$_4$)alkylthio, —NH—C(O)—(C$_1$-C$_4$)alkyl, —C(O)—(C$_1$-C$_4$)alkyl, —C(O)—O(C$_1$-C$_4$)alkyl, —C(O)—NH$_2$, —C(O)—NH(C$_1$-C$_4$)alkyl, a 3- to 6-membered carbocyclic ring, and phenyl substituted with F, Cl, Br, or I;

(ii) p and r are each 0 or 1, s is 1,

R$^{1a}$ and R$^{1b}$ are each independently selected from F, Cl, Br, I, cyano, —NH$_2$, —C(O)—(C$_1$-C$_4$)alkyl, (C$_1$-C$_6$)alkyl, (C$_1$-C$_6$)alkoxy, (C$_1$-C$_4$)alkylthio, fluoro-substituted (C$_1$-C$_4$)alkyl, fluoro-substituted (C$_1$-C$_4$)alkoxy, or fluoro-substituted (C$_1$-C$_4$)alkylthio, and (R$^{1c}$)$_s$ is bound to an adjacent carbon atom of the ring other than the carbon to which the group of Formula 1A is bound to the remainder of the molecule, and (R$^{1c}$)$_s$ taken together with the two carbons to which it is bound form a ring selected from the group consisting of:

a 5- to 6-membered carbocyclic ring which optionally contains a keto group, a 5- to 6-membered heterocyclic ring containing 1 to 2 heteroatoms independently selected from O, S or N, and which optionally contains a keto group, a 6-membered aromatic ring, and a 5- to 6-membered heteroaromatic ring containing 1 to 2 heteroatoms independently selected from O, S or N, where said carbocyclic ring, said heterocyclic ring, said aromatic ring and said heteroaromatic ring are optionally substituted with 1 to 2 substituents selected from the group consisting of (C$_1$-C$_4$)alkyl, cyano, acetyl, F, Cl, Br, I, phenylamino, (C$_1$-C$_4$)alkylamino, a 5- to 6-membered heterocyclic ring containing 1 to 3 hetero atoms independently selected from N, O and S which is optionally substituted with 1 to 3 substituents selected from (C$_1$-C$_4$)alkyl, and a 5- to 6-membered heteroaryl ring containing 1 to 3 hetero atoms independently selected from N, O and S which is optionally substituted with 1 to 3 substituents selected from (C$_1$-C$_4$)alkyl; or (iii) p and r are each 0, s is 1, and R$^{1c}$ is independently selected from the group consisting of phenyl, phenoxy optionally substituted with F, Cl, Br, or I; benzyl, benzyloxy, —NH(C$_1$-C$_4$)alkyl, —N[(C$_1$-C$_4$)alkyl]$_2$, —CH$_2$—NH(C$_1$-C$_4$)alkyl, —CH$_2$—N[(C$_1$-C$_4$)alkyl]$_2$, —NH(phenyl), —NH(5- to 6-membered heteroaryl containing 1 to 3 hetero atoms independently selected from O, N, and S, which is optionally substituted with 1 to 3 halo groups), —N(CH$_3$)—SO$_2$(C$_1$-C$_4$)alkyl, —NH—SO$_2$(C$_1$-C$_4$)alkyl, —NHC(O)NH$_2$, —C(O)—N[(C$_1$-C$_4$)alkyl]$_2$, —C(O)-(5- to 6-membered heterocycle containing 1 to 3 hetero atoms independently selected from O, N, and S), —C(O)—NH(5- to 6-membered heterocycle containing 1 to 3 hetero atoms independently selected from O, N, and S), —C(O)-(5- to 6-membered carbocycle), —CH$_2$—C(O)—O(C$_1$-C$_4$)alkyl, a 3- to 6-membered heterocyclic ring containing 1 to 3 heteroatoms independently selected from O, N or S, and a 5- to 6-membered heteroaryl containing 1 to 3 heteroaroms independently selected from O, N or S which is optionally substituted with one to three substituents independently selected from F, Cl, Br, I, and —CF$_3$;

(b) a 5- to 6-membered heteroaryl containing 1 to 3 heteroatoms independently selected from O, S or N, where said heteroaryl is optionally fused to a 5- to 6-membered carbocyclic ring or a 6-membered aromatic ring and said heteroaryl is optionally substituted with 1 to 2 substituents independently selected from the group consisting of cyano, F, Cl, Br, I, (C$_1$-C$_4$)alkyl, (C$_1$-C$_4$)alkoxy, and —C(O)—O(C$_1$-C$_4$)alkyl;

or a pharmaceutically acceptable salt thereof, or a solvate or hydrate of said compound or said salt.

An embodiment of the present invention includes a pharmaceutical composition comprising a compound of the present invention, and a pharmaceutically acceptable carrier. Preferably, the composition comprises a therapeutically effective amount of a compound of the present invention. The composition may also contain at least one additional pharmaceutical agent.

Yet another embodiment of the present invention includes a method for treating 5-HT$_{2c}$ receptor-mediated diseases, conditions, or disorders (as described herein) in animals comprising the step of administering to an animal in need of such treatment a therapeutically effective amount of a compound of the present invention (or a pharmaceutical composition thereof).

One aspect of the present invention is a method for treating obesity or controlling weight gain (including reducing or maintaining weight) comprising the step of administering to an animal in need of such treatment or control a therapeutically effective amount of a compound of the present invention.

Another aspect of the present invention is a method for treating psychosis (e.g., schizophrenia), anxiety, and related disorders comprising the step of administering to an animal in need of such treatment a therapeutically effective amount of a compound of the present invention.

Yet another aspect of the present invention is a method for treating female sexual dysfunction (FSD) comprising the step of administering to a female in need of such treatment a therapeutically effective amount of a compound of the present invention.

In yet another aspect of the present invention, a method is provided for treating male erectile dysfunction (MED) comprising the step of administering to a male in need of such treatment a therapeutically effective amount of a compound of the present invention.

In a further aspect of the present invention, a method is provided for treating lower urinary tract dysfunction, including urinary incontinence.

Compounds of the present invention may be administered in combination with other pharmaceutical agents (e.g., anti-obesity agents, anti-psychotic agents, agents for treating cognitive defects, anxiolytics, agents used for treating sexual dysfunction, agents for treating lower urinary tract dysfunction, etc.) described herein. Combination therapy may be administered as (a) a single pharmaceutical composition which comprises a compound of the present invention, at least one additional pharmaceutical agent and a pharmaceutically acceptable carrier; or (b) two separate pharmaceutical compositions comprising (i) a first composition comprising a compound of the present invention and a pharmaceutically acceptable carrier, and (ii) a second composition comprising at least one additional pharmaceutical agent and a pharmaceutically acceptable carrier. The pharmaceutical compositions may be administered simultaneously or sequentially and in any order.

DETAILED DESCRIPTION OF THE INVENTION

As used herein, the term "alkyl" refers to a hydrocarbon radical of the general formula $C_nH_{2n+1}$. The alkane radical may be straight or branched. For example, the term "$(C_1-C_6)$ alkyl" refers to a monovalent, straight, or branched aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, and the like). Similarly, the alkyl portion (i.e., alkyl moiety) of an alkoxy, acyl (e.g., alkanoyl), alkylamino, dialkylamino, and alkylthio group have the same definition as above. When indicated as being "optionally substituted", the alkane radical or alkyl moiety may be unsubstituted or substituted with one or more substituents (generally, one to three substituents except in the case of halogen substituents such as perchloro or perfluoroalkyls) independently selected from the group of substituents listed below in the definition for "substituted." "Halo-substituted alkyl" refers to an alkyl group substituted with one or more halogen atoms (e.g., fluoromethyl, difluoromethyl, trifluoromethyl, perfluoroethyl, and the like).

The terms "partially or fully saturated carbocyclic ring" (also referred to as "partially or fully saturated cycloalkyl") refers to nonaromatic rings that are either partially or fully hydrogenated and may exist as a single ring, bicyclic ring or a spiral ring. Unless specified otherwise, the carbocyclic ring is generally a 3- to 8-membered ring (preferably, 3- to 6-membered ring). For example, partially or fully saturated carbocyclic rings (or cycloalkyl) include groups such as cyclopropyl, cyclopropenyl, cyclobutyl, cyclobutenyl, cyclopentyl, cyclpentenyl, cyclopentadienyl, cyclohexyl, cyclohexenyl, cyclohexadienyl, norbornyl (bicyclo[2.2.1]heptyl), norbornenyl, bicyclo[2.2.2]octyl, and the like. When designated as being "optionally substituted", the partially saturated or fully saturated cycloalkyl group may be unsubstituted or substituted with one or more substituents (typically, one to three substituents) independently selected from the group of substituents listed below in the definition for "substituted." A substituted carbocyclic ring also includes groups wherein the carbocyclic ring is fused to a phenyl ring (e.g., indanyl). The carbocyclic group may be attached to the chemical entity or moiety by any one of the carbon atoms within the carbocyclic ring system. Similarly, any cycloalkyl portion of a group (e.g., cycloalkylalkyl, cycloalkylamino, etc.) has the same definition as above.

The term "partially saturated or fully saturated heterocyclic ring" (also referred to as "partially saturated or fully saturated heterocycle") refers to nonaromatic rings that are either partially or fully hydrogenated and may exist as a single ring, bicyclic ring or a spiral ring. Unless specified otherwise, the heterocyclic ring is generally a 3- to 6-membered ring containing 1 to 3 heteroatoms (preferably 1 or 2 heteroatoms) independently selected from sulfur, oxygen or nitrogen. Partially saturated or fully saturated heterocyclic rings include groups such as epoxy, aziridinyl, tetrahydrofuranyl, dihydrofuranyl, dihydropyridinyl, pyrrolidinyl, N-methylpyrrolidinyl, imidazolidinyl, imidazolinyl, piperidinyl, piperazinyl, pyrazolidinyl, 2H-pyranyl, 4H-pyranyl, 2H-chromenyl, oxazinyl, morpholino, thiomorpholino, tetrahydrothienyl, tetrahydrothienyl 1,1-dioxide, and the like.

When indicated as being "optionally substituted", the partially saturated or fully saturated heterocycle group may be unsubstiuted or substituted with one or more substituents (typically, one to three substituents) independently selected from the group of substituents listed below in the definition for "substituted." A substituted heterocyclic ring includes groups wherein the heterocyclic ring is fused to an aryl or heteroaryl ring (e.g., 2,3-dihydrobenzofuranyl, 2,3-dihydroindolyl, 2,3-dihydrobenzothiophenyl, 2,3-dihydrobenzothiazolyl, etc.). The heterocyclic group may be attached to the chemical entity or moiety by any one of the ring atoms within the heterocyclic ring system. Similarly, any heterocycle portion of a group (e.g., heterocycle-substituted alkyl, heterocycle carbonyl, etc.) has the same definition as above.

The term "aryl" or "aromatic ring" refers to aromatic moieties having a single (e.g., phenyl) or a fused ring system (e.g., naphthalene, anthracene, phenanthrene, etc.). A typical aryl group is a 6- to 10-membered aromatic carbocyclic ring(s). When indicated as being "optionally substituted", the aryl groups may be unsubstituted or substituted with one or more substituents (preferably no more than three substituents) independently selected from the group of substituents listed below in the definition for "substituted" (unless specified otherwise). Substituted aryl groups include a chain of aromatic moieties (e.g., biphenyl, terphenyl, phenylnaphthalyl, etc.). The aryl group may be attached to the chemical moiety by any one of the carbon atoms of the aromatic ring system. The aryl portion (i.e., aromatic moiety) of an aroyl or aroyloxy (i.e., (aryl)-C(O)—O—) has the same definition as above.

The term "heteroaryl" or "heteroaromatic ring" refers to aromatic moieties containing at least one heteroatom (e.g., oxygen, sulfur, nitrogen or combinations thereof) within a 5- to 10-membered aromatic ring system (e.g., pyrrolyl, pyridyl, pyrazolyl, indolyl, indazolyl, thienyl, furanyl, benzofuranyl, oxazolyl, imidazolyl, tetrazolyl, triazinyl, pyrimidyl, pyrazinyl, thiazolyl, purinyl, benzimidazolyl, quinolinyl, isoquinolinyl, benzothiophenyl, benzoxazolyl, etc.). The heteroaromatic moiety may consist of a single or fused ring system. A typical single heteroaryl ring is a 5- to 6-membered ring containing one to three heteroatoms independently selected from oxygen, sulfur and nitrogen and a typical fused heteroaryl ring system is a 9- to 10-membered ring system containing one to four heteroatoms independently selected from oxygen, sulfur and nitrogen. When indicated as being "optionally substituted", the heteroaryl groups may be unsubstituted or substituted with one or more substituents (preferably no more than three substituents) independently selected from the group of substituents listed below in the definition for "substituted" (unless specified otherwise). The heteroaryl group may be attached to the chemical entity or moiety by any one of the atoms within the aromatic ring system (e.g., pyrid-2-yl, pyrid-3-yl, pyrid-4-yl, pyrid-5-yl, or pyrid-6-yl). Similarly, the heteroaryl portion (i.e., heteroaromatic moiety) of a heteroaroyloxy (i.e., (heteroaryl)-C(O)—O—) has the same definition as above.

The term "acyl" refers to alkyl, partially saturated or fully saturated cycloalkyl, partially saturated or fully saturated heterocycle, aryl, and heteroaryl substituted carbonyl groups. For example, acyl includes groups such as $(C_1-C_6)$alkanoyl (e.g., formyl, acetyl, propionyl, butyryl, valeryl, caproyl, t-butylacetyl, etc.), $(C_3-C_6)$cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions above. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "substituted" specifically envisions and allows for one or more substitutions that are common in the art. However, it is generally understood by those skilled in the art that the substituents should be selected so as to not adversely affect the pharmacological characteristics of the compound or adversely interfere with the use of the medicament. Suitable substituents for any of the groups defined above include $(C_1-C_6)$alkyl, $(C_3-C_7)$cycloalkyl, $(C_2-C_6)$alkenyl, $(C_1-C_6)$alkylidenyl, aryl, heteroaryl, 3- to 6-membered heterocycle, halo (e.g., chloro, bromo, iodo and fluoro), cyano, hydroxy, $(C_1-C_6)$alkoxy, aryloxy, sulfhydryl(mercapto), $(C_1-C_6)$alkylthio, arylthio, amino, mono- or di-$(C_1-C_6)$alkyl amino, quaternary ammonium salts, amino$(C_1-C_6)$alkoxy, aminocarboxylate (i.e., $(C_1-C_6)$alkyl-O—C(O)—NH—), hydroxy$(C_2-C_6)$alkylamino, amino$(C_1-C_6)$alkylthio, cyanoamino, nitro, $(C_1-C_6)$carbamyl, keto(oxo), acyl, $(C_1-C_6)$alkyl-$CO_2$—, glycolyl, glycyl, hydrazino, guanyl, sulfamyl, sulfonyl, sulfinyl, thio$(C_1-C_6)$alkyl-C(O)—, thio$(C_1-C_6)$alkyl-$CO_2$—, and combinations thereof. In the case of substituted combinations, such as "substituted aryl$(C_1-C_6)$alkyl", either the aryl or the alkyl group may be substituted, or both the aryl and the alkyl groups may be substituted with one or more substituents (typically, one to three substituents except in the case of perhalo substitutions). An aryl or heteroaryl substituted carbocyclic or heterocyclic group may be a fused ring (e.g., indanyl, dihydrobenzofuranyl, dihydroindolyl, etc.).

The term "halo" refers to a chloro, bromo, fluoro or iodo group.

The term "solvate" refers to a molecular complex of a compound represented by Formula (I) (including pharmaceutically acceptable salts thereof) with one or more solvent molecules. Such solvent molecules are those commonly used in the pharmaceutical art, which are known to be innocuous to the recipient, e.g., water, ethanol, and other Class 3 solvents (see, US Federal Drug Administration Guidelines for a list of Class 3 solvents). The term "hydrate" refers to the complex where the solvent molecule is water.

The term "protecting group" or "Pg" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBz) and 9-fluorenylmethylenoxycarbonyl (Fmoc). For a general description of protecting groups and their use, see T. W. Greene, *Protective Groups in Organic Synthesis*, John Wiley & Sons, New York, 1991.

The term "ligand" refers to a compound that binds to a receptor. As used herein, the ligand may possess partial or full agonist or antagonist activity. The term "agonist", unless indicated otherwise, includes both partial and full agonists. Full agonists are preferred. The term "modulator" refers to a ligand that increases or decreases the action of an agonist by combining with a distinct site on the receptor macromolecule.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "animal" refers to humans, companion animals (e.g., dogs, cats and horses), food-source animals, zoo animals, marine animals, birds and other similar animal species.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment.

The term "compound(s) of the present invention" (unless specifically identified otherwise) refers to compounds of Formula (I), (II), (IIB), or (IIC), pharmaceutically acceptable salts thereof, and/or and hydrates or solvates of the compounds, and/or the salts, as well as, all stereoisomers (including diastereoisomers and enantiomers), tautomers and isotopically labeled compounds.

Compounds of formula I may contain chiral centers and therefore may exist in different enantiomeric and diastereomeric forms. Individual isomers can be obtained by known methods, such as optical resolution, optically selective reaction, or chromatographic separation in the preparation of the final product or its intermediate. This invention relates to all optical isomers and all stereoisomers of compounds of the formula I, both as racemic mixtures and as individual enantiomers and diastereoisomers of such compounds, and mixtures thereof, and to all pharmaceutical compositions and methods of treatment recited herein that contain or employ them, respectively.

A preferred stereochemistry for the compound of Formula (I) is shown in Formula (II).

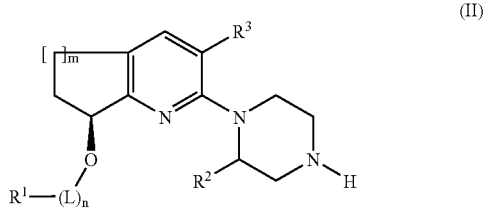
(II)

where m, n, L, R¹ and R² are as defined above for the compound of Formula (I).

Where R² is methyl, a preferred stereochemistry for the compound of formula (I) is shown in Formula (IIB).

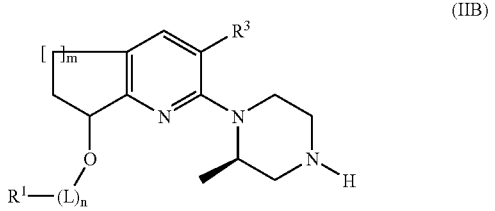
(IIB)

R² of formula (IIB) is (R)-methyl.

In another embodiment in which R² is methyl, a preferred stereochemistry for the compound of formula (I) is shown in formula (IIC).

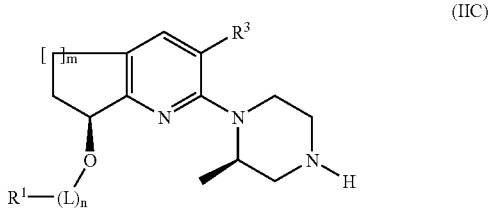
(IIC)

R² of formula (IIC) is (R)-methyl.

Compounds of the present invention may be synthesized by synthetic routes that include processes analogous to those known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, New York (1967-1999 ed.), or *Beilsteins Handbuch der organischen Chemie*, 4, Aufl. ed. Springer-Verlag, Berlin, including supplements (also available via the Beilstein online database)).

For illustrative purposes, the reaction scheme depicted below provides a potential route for synthesizing the compounds of the present invention as well as key intermediates. Those skilled in the art will appreciate that other synthetic routes may be used to synthesize the inventive compounds. Although specific starting materials and reagents are depicted in the scheme and discussed below, other starting materials and reagents can be easily substituted to provide a variety of intermediates and/or reaction conditions. In addition, many of the compounds prepared by the method described below can be further modified in light of this disclosure using conventional chemistry well known to those skilled in the art.

In the preparation of compounds of the present invention, protection of remote functionality (e.g., secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, *Protective Groups in Organic Synthesis*, John Wiley & Sons, New York, 1991.

Scheme I illustrates the general procedures for preparing a compound of Formula (I) or (II) where m is 0 or 1 and n is 1 (designated as a compound of Formula (I-A)).

Scheme I

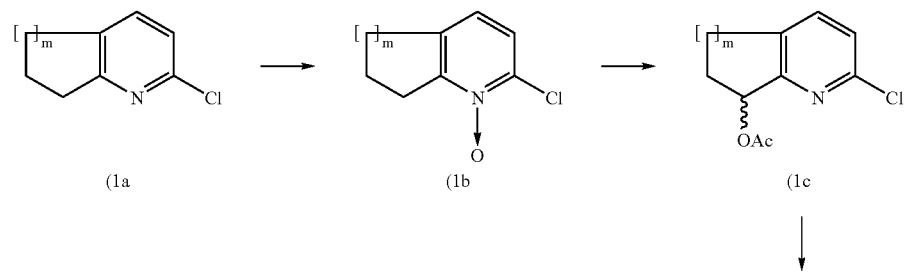

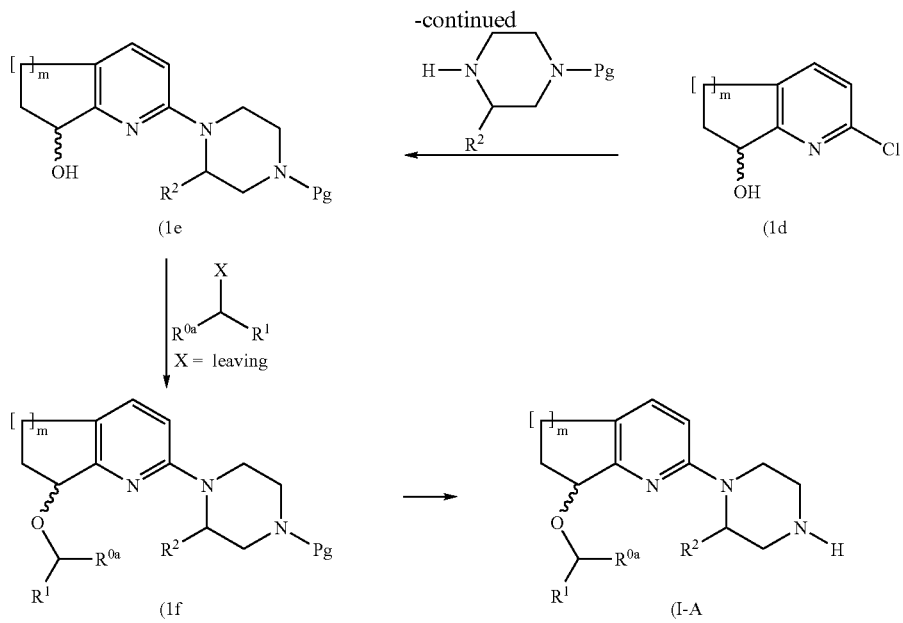

The N-oxide intermediate (1b) is produced by oxidizing the corresponding 2-chloro-6,7-dihydro-5H-cyclopenta[b]pyridine (i.e., m=1) or 2-chloro-5,6,7,8-tetrahydroquinoline (i.e., m=2) with an appropriate oxidizing agent well-known to those skilled in the art. For example, starting material (1a) may be treated with m-chloroperbenzoic acid in a non-protic solvent (e.g., methylene chloride). The acetate intermediate (1c) may then be formed by treating the N-oxide (1b) with acetic anhydride at elevated temperatures (e.g., 110° C.). For general reference to acetic anhydride/acetate rearrangements, see J. Am. Chem. Soc. 1991, 113 (1), 183-196. The racemic acetate intermediate (1c) may be separated into the two pure enantiomers at this stage using a Chiralpak AD column (dimension 4.6 mm×25 cm) with an appropriate solvent. For example, the mobile phase may contain about 85% heptane and about 15% EtOH without a modifier. The flow rate is generally set at about 1 mL/min.

The acetate protection group may then be removed by treating with aqueous base (e.g., potassium carbonate in water) in a protic solvent (e.g., methanol). The desired monoprotected piperazine is then coupled with the chloro intermediate (1d) using a palladium catalyst amination. For example, the desired piperazine may be coupled to the chloro intermediate (1d) in the presence of a palladium catalyst (e.g., Pd$_2$(OAc)$_2$ or Pd$_2$(dba)$_3$), 2,2'-bis(diphenylphosphino)-1,1'-binaphthyl (BINAP), and a strong base (e.g., sodium t-butoxide) in an aprotic solvent (e.g., toluene or THF) to yield the intermediate (1e). The desired ether linkage may be incorporated into intermediate (1e) using standard ether forming conditions. For example, intermediate (1e) may be reacted with the desired R$^1$—C(R$^{0a}$)—X (where X is a leaving group) in the presence of a strong base (e.g., sodium hydride) and tetrabutylammonium iodide in a polar solvent (e.g., dimethylformamide (DMF)) to give the intermediate (1f). Lastly, the amino-protecting group is removed to produce the compound of Formula (I-A). For example, when the amino-protecteding group is BOC, the intermediate (1f) is typically treated with a trifluoroacetic acid in methylene chloride solution to cleave the BOC protecting group.

Scheme II illustrates an alternative route to compounds of Formula (I) or (II) where m is 0 or 1 and n is 1.

Scheme II

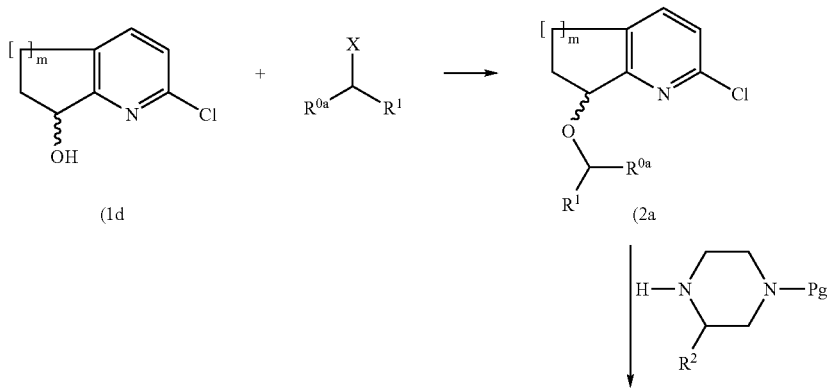

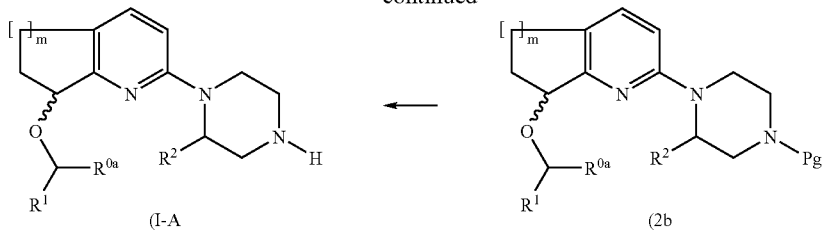

The compound of Formula (I-A) may be alternatively synthesized by starting with intermediate (1d) from Scheme I above, where the ether linkage is introduced first followed by the addition of the piperazine group. Similar to the reactions described above in Scheme I, intermediate (1d) may be first reacted with the desired $R^1$—C($R^{0a}$)—X (where X is a leaving group), a strong base (e.g., sodium hydride) and tetrabutylammonium iodide in a polar solvent (e.g., dimethylformamide (DMF)) to give the intermediate (2a). The piperazine group may then introduced using a palladium catalyzed amination. Finally, the amino-protecting group is removed to produce the compound of Formula (I-A).

Scheme III illustrates the general procedures for preparing a compound of Formula (I) or (II) where m is 0 or 1 and n is 0.

Scheme III

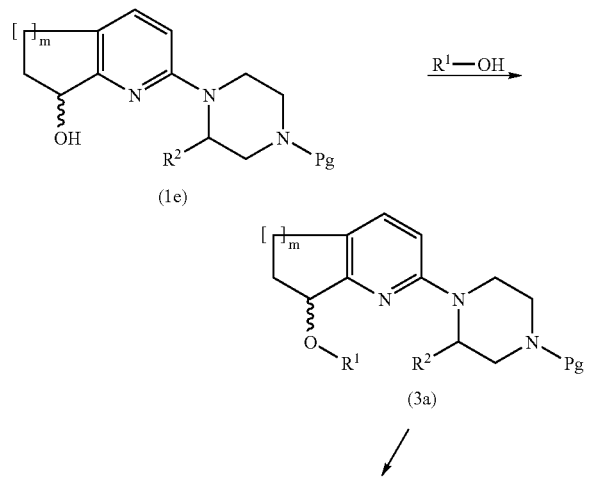

Again similar to the procedures described above in Schemes I and II. The $R^1$ group may be introduced by using modified Mitsonobu conditions. For example, intermediate (1e) is coupled with the desired hydroxy compound ($R^1$—OH) using solid phase triphenylphosphine (i.e., polymer bound triphenyphosphine) and diethyl azodicarboxylate (DEAD). The amino-protecting group may then be removed using standard reaction conditions appropriate for the particular protecting group used. For example, trifluoroacetic acid may be used to remove a BOC protecting group.

Scheme IV illustrates an alternative route to compounds of Formula (I) or (II) where m is 0 or 1 and n is 0.

Scheme IV

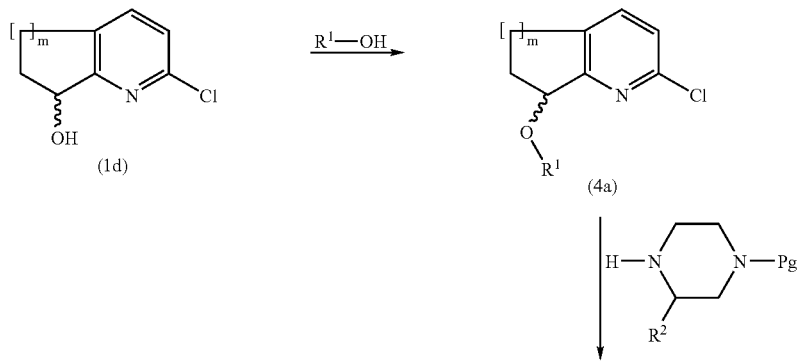

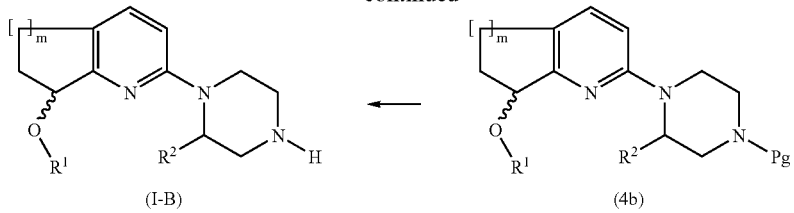

(I-B)          (4b)

Alternatively, the compound of Formula (I-B) may be synthesized by introducing the ether linkage first followed by the addition of the piperazine group. Similar to the reaction conditions described in Schemes III. The ether linkage may be introduced using a modified Mitsonabu coupling reaction. For example, intermediate (1d) is coupled with the desired hydroxy compound ($R^1$—OH) using solid phase triphenylphosphine (i.e., polymer bound triphenyphosphine) and diethyl azodicarboxylate (DEAD) to produce intermediate (4a). The piperazine group may then be introduced using a palladium catalyzed amination as described above in Schemes I and II. Finally, the amino-protecting group is removed using standard conditions that are appropriate for the particular protecting group used.

Conventional methods and/or techniques of separation and purification known to one of ordinary skill in the art can be used to isolate the compounds of the present invention, as well as the various intermediates related thereto. Such techniques will be well-known to one of ordinary skill in the art and may include, for example, all types of chromatography (high pressure liquid chromatography (HPLC), column chromatography using common adsorbents such as silica gel, and thin-layer chromatography), recrystallization, and differential (i.e., liquid-liquid) extraction techniques.

Enantiomeric mixtures may be separated into the pure enantiomers using techniques well-known to those skilled in the art, such as chiral liquid chromatography columns or thin layer chromatography. For example, the racemic compound or enantio-enriched compound may be separated on a Chiralpak™ AD column (dimension 4.6 mm×25 cm) using an appropriate mobile phase with or without a modifer (e.g., TFA) at a flow rate of about 1 mL/minute. The enantiomeric separation may be made with one of the intermediates (preferably, the acetate intermediate (1c)) or the final product.

The enantiomers can alternatively be resolved and separated by crystallization with a chiral molecule. The pure enantiomer could be recovered from a diasteriomeric derivative.

If it is desired to obtain a high degree of optical purity, compounds may be further purified by chiral HPLC as is well known in the art, for example, using a Chiralcel OJ or Chiralpak AD column in heptane/IPA with or without a base or acid modifier. A chiral separation was performed, for instance, using Chiralpak AD with 95/5 heptane/IPA.

The term "salts" refers to inorganic and organic salts of a compound of the present invention. These salts can be prepared in situ during the final isolation and purification of a compound, or by separately reacting the compound with a suitable organic or inorganic acid and isolating the salt thus formed. Representative salts include the hydrobromide, hydrochloride, hydroiodide, sulfate, bisulfate, nitrate, acetate, trifluoroacetate, oxalate, besylate, palmitiate, pamoate, malonate, stearate, laurate, malate, borate, benzoate, lactate, phosphate, hexafluorophosphate, benzene sulfonate, tosylate, formate, citrate, maleate, fumarate, succinate, tartrate, naphthylate, mesylate, glucoheptonate, lactobionate, and laurylsulphonate salts, and the like. See, e.g., Berge, et al., *J. Pharm. Sci.*, 66, 1-19 (1977).

The compounds of the present invention may exist in unsolvated as well as solvated forms with pharmaceutically acceptable solvents such as water, ethanol, and the like, and it is intended that the invention embrace both solvated and unsolvated forms. Suitable pharmaceutically acceptable solvents include the Class 3 solvents listed in the United States Federal Drug Administration Guidelines.

The present invention also embraces isotopically-labeled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, fluorine and chlorine, such as $^2$H, $^3$H, $^{13}$C, $^{14}$C, $^{15}$N, $^{18}$O, $^{17}$O, $^{18}$F, and $^{36}$Cl.

Certain isotopically-labeled compounds of the present invention (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the present invention can generally be prepared by following procedures analogous to those disclosed in the Schemes and/or in the Examples hereinbelow, by substituting an isotopically labeled reagent for a non-isotopically labeled reagent.

Compounds of the present invention are selective 5-$HT_{2c}$ agonists. The compounds may be used to treat diseases or conditions that are effectively treated by agonism of the 5-$HT_{2c}$ receptor. The compounds may be used to treat 5-$HT_2$ receptor-mediated diseases.

An embodiment of the present invention is a pharmaceutical composition comprising a therapeutically effective amount of a compound of the present invention and a pharmaceutically acceptable carrier and optionally, a pharmaceutically acceptable excipient or diluent. The pharmaceutical compositions may be used to treat 5-$HT_2$ receptor-mediated diseases.

A typical formulation is prepared by mixing a compound of the present invention and a carrier, and optionally, a diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable dosage of the drug and to give the patient an elegant and easily handleable product.

A pharmaceutical compostiiton of the present invention can be administered to a patient in any conventional oral, rectal, transdermal, parenteral, (for example, intravenous, intramuscular, or subcutaneous) intracisternal, intravaginal, intraperitoneal, intravesical, local (for example, powder, ointment or drop), or buccal, or nasal, dosage form.

The present invention further provides methods of treating 5-HT$_2$ receptor-mediated diseases, conditions, or disorders in an animal in need of such treatment that include administering to the animal (preferably, a human) a therapeutically effective amount of a compound of the present invention or a pharmaceutical composition comprising an effective amount of a compound of the present invention and a pharmaceutically acceptable carrier. In particular, the compounds of the present invention act as potent full agonists at the 5-HT$_{2c}$ receptor, and as antagonists or weak partial agonists at the 5-HT$_{2a}$ and 5-HT$_{2b}$ receptors. The compounds of the present invention are functionally selective for 5-HT$_{2c}$ against 5-HT$_{2a}$ and 5-HT$_{2b}$, by virtue of their much greater agonistic potency (lower EC$_{50}$) for 5-HT$_{2c}$ than that observed for 5-HT$_{2a}$ and/or 5-HT$_{2b}$ or their lack of agonistic activity at 5-HT$_{2a}$ and/or 5-HT$_{2b}$.

Receptor binding data or binding selectivity data may not always correlate with or reflect functional data or functional selectivity data. For example, a compound may be selective for the 5-HT$_{2c}$ receptor when functional assays are analyzed, but in the binding assays the compound may have the same potency at other 5-HT receptors. Thus, the term "selective" as used herein in relation to the present invention with respect to methods of treatment means "functionally selective".

In connection with the alleviation of side effects, preferred are compounds of the present invention that exhibit 5-HT$_{2a}$ antagonism and/or 5-HT$_{2b}$ antagonism in vivo.

Accordingly, the compounds of the present invention described herein are useful in treating 5-HT$_2$ receptor-mediated diseases, conditions, or disorders. Consequently, the compounds of the present invention may be used in the manufacture of a medicament for the therapeutic applications described herein.

Diseases, conditions, and/or disorders modulated by 5HT$_2$ receptor ligands include eating disorders (e.g., binge eating disorder, anorexia, and bulimia), weight loss or control (e.g., reduction in calorie or food intake, and/or appetite suppression), obesity, depression, atypical depression, bipolar disorders, psychoses, schizophrenia, behavioral addictions, suppression of reward-related behaviors (e.g., conditioned place avoidance, such as suppression of cocaine- and morphine-induced conditioned place preference), substance abuse, addictive disorders, impulsivity, alcoholism (e.g., alcohol abuse, addiction and/or dependence including treatment for abstinence, craving reduction and relapse prevention of alcohol intake), tobacco abuse (e.g., smoking addiction, cessation and/or dependence including treatment for craving reduction and relapse prevention of tobacco smoking), premenstrual syndrome or late luteal phase syndrome, migraine, panic disorder, anxiety, post-traumatic syndrome, dementia (including memory loss, Alzheimer's disease, dementia of aging, vascular dementia, mild cognitive impairment, age-related cognitive decline, and mild neurocognitive disorder), seizure disorders, epilepsy, gastrointestinal disorders (e.g., dysfunction of gastrointestinal motility or intestinal propulsion), attention deficit disorders or attention hyperactivity disorders (ADD/ADHD), disruptive behavior disorders, impulse control disorders, borderline personality disorder, obsessive compulsive disorder, chronic fatigue syndrome, anorexia nervosa, disorders of sleep (e.g., sleep apnea), autism, epilepsy, mutism, spinal cord injury, damage of the central nervous system (e.g., trauma, stroke, neurodegenerative diseases or toxic or infective CNS diseases (e.g., encephalitis or meningitis)), cardiovascular disorders (e.g., thrombosis), Parkinson's disease, diabetes insipidus, and type II diabetes.

In another embodiment, this invention relates to a method for treating psychotic disorders and conditions such as schizophrenia, delusional disorders and drug induced psychosis; anxiety disorders such as panic and obsessive-compulsive disorder; and movement disorders including Parkinson's disease and Huntington's disease, comprising an amount of a compound of formula I effective in treating said disorder or condition.

Examples of psychotic disorders that can be treated according to the present invention include, but are not limited to, schizophrenia, for example of the paranoid, disorganized, catatonic, undifferentiated, or residual type; schizophreniform disorder; schizoaffective disorder, for example of the delusional type or the depressive type; delusional disorder; substance-induced psychotic disorder, for example psychosis induced by alcohol, amphetamine, cannabis, cocaine, hallucinogens, inhalants, opioids, or phencyclidine; personality disorder of the paranoid type; and personality disorder of the schizoid type.

In use to treat psychotic disorders of the schizophrenic types, the compounds would in particular be useful for removing or ameliorating such symptoms as anxiety, agitation, excessive aggression, tension, and social or emotional withdrawal in psychotic patients. In addition, the compounds may be useful in the blocking of serotonin-induced contractions of bronchial tissues and of blood vessels, arteries as well as veins. The compounds of the present invention may also be useful as sedating-, anxiolytic-, anti-aggressive-, anti-stress-, muscular protectant-, and cardiovascular protectant agents and, consequently, they would be useful to protect warm-blooded animals, for example, in stress situations, e.g., during transport periods and the like situations.

Examples of movement disorders that can be treated according to the present invention include but are not limited to selected from Huntington's disease and dyskinesia associated with dopamine agonist therapy, Parkinson's disease, restless leg syndrome, and essential tremor.

Other disorders that can be treated according to the present invention are obsessive/compulsive disorders, Tourette's syndrome and other tic disorders.

This invention also provides a method for treating an anxiety disorder or condition in a mammal which method comprises administering to said mammal an amount of a compound of formula I effective in treating said disorder or condition. Examples of anxiety disorders that can be treated according to the present invention include, but are not limited to, panic disorder; agoraphobia; a specific phobia; social phobia; obsessive-compulsive disorder; post-traumatic stress disorder; acute stress disorder; and generalized anxiety disorder.

This invention further provides a method of treating a drug addiction, for example an alcohol, amphetamine, cocaine, or opiate addiction, in a mammal, including a human, which method comprises administering to said mammal an amount of a compound of formula I effective in treating drug addiction. A "drug addiction", as used herein, means an abnormal desire for a drug and is generally characterized by motivational disturbances such a compulsion to take the desired drug and episodes of intense drug craving.

This invention also provides a method of treating a disorder or condition comprising as a symptom a deficiency in attention and/or cognition in a mammal, including a human, which method comprises administering to said mammal an amount of a compound of formula I effective in treating said disorder or condition. The phrase "deficiency in attention and/or cognition" as used herein in "disorder comprising as a symptom a deficiency in attention and/or cognition" refers to a subnormal functioning in one or more cognitive aspects such as memory, intellect, or learning and logic ability, in a particular individual relative to other individuals within the same general age population. "Deficiency in attention and/or cognition" also refers to a reduction in any particular individual's functioning in one or more cognitive aspects, for example as occurs in age-related cognitive decline.

Examples of disorders that comprise as a symptom a deficiency in attention and/or cognition that can be treated according to the present invention are dementia, for example Alzheimer's disease, multi-infarct dementia, alcoholic dementia or other drug-related dementia, dementia associated with intracranial tumors or cerebral trauma, dementia associated with Huntington's disease or Parkinson's disease, or AIDS-related dementia; delirium; amnestic disorder; post-traumatic stress disorder; mental retardation; a learning disorder, for example reading disorder, mathematics disorder, or a disorder of written expression; attention-deficit/hyperactivity disorder; age-related cognitive decline; cognitive deficits associated with psychoses, and cognitive deficits associated with schizophrenia.

This invention also provides a method of treating a mood disorder or mood episode in a mammal, including a human, comprising administering to said mammal an amount of a compound of formula I effective in treating said disorder or episode. Examples of mood disorders and mood episodes that can be treated according to the present invention include, but are not limited to, major depressive episode of the mild, moderate or severe type, a manic or mixed mood episode, a hypomanic mood episode; a depressive episode with atypical features; a depressive episode with melancholic features; a depressive episode with catatonic features; a mood episode with postpartum onset; post-stroke depression; major depressive disorder; dysthymic disorder; minor depressive disorder; premenstrual dysphoric disorder; post-psychotic depressive disorder of schizophrenia; a major depressive disorder superimposed on a psychotic disorder such as delusional disorder or schizophrenia; a bipolar disorder, for example bipolar I disorder, bipolar II disorder, and cyclothymic disorder.

This invention further provides a method of treating a neurodegenerative disorder or condition in a mammal, including a human, which method comprises administering to said mammal an amount of a compound of formula I effective in treating said disorder or condition. As used herein, and unless otherwise indicated, a "neurodegenerative disorder or condition" refers to a disorder or condition that is caused by the dysfunction and/or death of neurons in the central nervous system. The treatment of these disorders and conditions can be facilitated by administration of an agent which prevents the dysfunction or death of neurons at risk in these disorders or conditions and/or enhances the function of damaged or healthy neurons in such a way as to compensate for the loss of function caused by the dysfunction or death of at-risk neurons. The term "neurotrophic agent" as used herein refers to a substance or agent that has some or all of these properties.

Examples of neurodegenerative disorders and conditions that can be treated according to the present invention include, but are not limited to, Parkinson's disease; Huntington's disease; dementia, for example Alzheimer's disease, multi-infarct dementia, AIDS-related dementia, and Fronto temporal Dementia; neurodegeneration associated with cerebral trauma; neurodegeneration associated with stroke, neurodegeneration associated with cerebral infarct; hypoglycemia-induced neurodegeneration; neurodegeneration associated with epileptic seizure; neurodegeneration associated with neurotoxin poisoning; and multi-system atrophy.

In one embodiment of the present invention, the neurodegenerative disorder or condition comprises neurodegeneration of striatal medium spiny neurons in a mammal, including a human. In a further embodiment of the present invention, the neurodegenerative disorder or condition is Huntington's disease.

In another embodiment of the present invention, the compounds of the present invention may be used in the prophylaxis and/or treatment of sexual dysfunction. Sexual dysfunction (SD) is a significant clinical problem, which can affect both males and females. The causes of SD may be both organic as well as psychological. Organic aspects of SD are typically caused by underlying vascular diseases, such as those associated with hypertension or diabetes mellitus, by prescription medication and/or by psychiatric disease such as depression. Physiological factors include fear, performance anxiety and interpersonal conflict. SD impairs sexual performance, diminishes self-esteem and disrupts personal relationships thereby inducing personal distress. In the clinic, SD disorders have been divided into female sexual dysfunction (FSD) disorders and male sexual dysfunction (MSD) disorders (Melman et al 1999). FSD includes female sexual arousal disorder (FSAD), desire disorders such as hypoactive sexual disorder (lack of interest in sex), and orgasmic disorders such as anorgasmia (unable to achieve orgasm). Male sexual dysfunction (MSD) includes male erectile dysfunction (MED) and ejaculatory disorders such as an orgasmia (unable to achieve orgasm) or desire disorders such as hypoactive sexual desire disorder (lack of interest in sex).

The compounds of the invention are particularly beneficial for the prophylaxis and/or treatment of sexual dysfunction in the male (e.g. male erectile dysfunction—MED) and in the female—female sexual dysfunction (FSD), e.g. female sexual arousal disorder (FSAD).

In a further aspect, the present invention provides a method for treating lower urinary tract dysfunction by administering to a mammal a compound of Formula I in an amount effective to treat the disorder. Conditions of lower urinary tract dysfunction include overactive bladder, increased daytime frequency, nocturia, urgency, urinary incontinence (any condition in which there is an involuntary leakage of urine), including stress urinary incontinence, urge urinary incontinence and mixed urinary incontinence, overactive bladder with associated urinary incontinence, enuresis, nocturnal enuresis, continuous urinary incontinence, situational urinary incontinence such as incontinence during sexual intercourse, and lower urinary tract symptoms (LUTS) associated with benign prostatic hyperplasia (BPH).

The compounds of the present invention can be administered to a patient at dosage levels in the range of from about 0.1 mg to about 1,000 mg per day (preferably, about 1 mg to about 500 mg per day, more preferably, about 2.5 mg to about 250 mg per day, still more preferably about 5 mg to about 150 mg per day, and most preferably, about 60 mg to about 100 mg per day). For a normal adult human having a body weight of about 70 kg, a dosage in the range of from about 0.01 mg to about 2 mg per kilogram body weight is typically sufficient. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

The compounds of the invention may also be used in conjunction with other pharmaceutical agents for the treatment of the diseases/conditions described herein. Therefore, methods of treatment that include administering compounds of the present invention in combination with other pharmaceutical agents are also provided. Suitable pharmaceutical agents that may be used in combination with the compounds of the present invention include anti-obesity agents such as apolipoprotein-B secretion/microsomal triglyceride transfer protein (apo-B/MTP) inhibitors, 11β-hydroxy steroid dehydrogenase-1 (11β-HSD type 1) inhibitors, $PYY_{3-36}$ and analogs thereof, MCR-4 agonists, cholecystokinin-A (CCK-A) agonists, monoamine reuptake inhibitors (such as sibutramine), sympathomimetic agents, $\beta_3$ adrenergic receptor agonists, dopamine agonists (such as bromocriptine), melanocyte-stimulating hormone receptor analogs, cannabinoid 1 receptor antagonists (e.g., rimonabant), melanin concentrating hormone antagonists, leptins (the OB protein), leptin analogs, leptin receptor agonists, galanin antagonists, lipase inhibitors (such as tetrahydrolipstatin, i.e. orlistat), anorectic agents (such as a bombesin agonist), Neuropeptide-Y receptor antagonists (e.g., NPY Y5 receptor antagonists, such as the spiro compounds described in U.S. Pat. Nos. 6,566,367; 6,649,624; 6,638,942; 6,605,720; 6,495,559; 6,462,053; 6,388,077; 6,335,345; and 6,326,375; US Publication Nos. 2002/0151456 and 2003/036652; and PCT Publication Nos. WO 03/010175. WO 03/082190 and WO 02/048152), thyromimetic agents, dehydroepiandrosterone or an analog thereof, glucocorticoid receptor agonists or antagonists, orexin receptor antagonists, urocortin binding protein antagonists, glucagon-like peptide-1 receptor agonists, ciliary neurotrophic factors (such as Axokine™ available from Regeneron Pharmaceuticals, Inc., Tarrytown, N.Y. and Procter & Gamble Company, Cincinnati, Ohio), human agouti-related proteins (AGRP), ghrelin receptor antagonists, histamine 3 receptor antagonists or inverse agonists, and neuromedin U receptor agonists. Other anti-obesity agents, including the preferred agents set forth hereinbelow, are well known, or will be readily apparent in light of the instant disclosure, to one of ordinary skill in the art.

Preferred are anti-obesity agents selected from the group consisting of orlistat, sibutramine, bromocriptine, ephedrine, leptin, rimonabant, pseudoephedrine, $PYY_{3-36}$ or an analog thereof, and 2-oxo-N-(5-phenylpyrazinyl)spiro-[isobenzofuran-1(3H),4'-piperidine]-1'-carboxamide.

Other suitable pharmaceutical agents that may be administered in combination with the compounds of the present invention include agents designed to treat tobacco abuse (e.g., nicotine receptor partial agonists, bupropion hypochloride (also known under the tradename Zyban™) and nicotine replacement therapies), ADD/ADHD treatment agents (e.g., Ritalin™, Strattera™, Concerta™ and Adderall™), and agents to treat alcoholism, such as opioid antagonists (e.g., naltrexone (also known under the tradename ReVia™) and nalmefene), disulfiram (also known under the tradename Antabuse™), and acamprosate (also known under the tradename Campral™)). In addition, agents for reducing alcohol withdrawal symptoms may also be co-administered, such as benzodiazepines, beta-blockers, clonidine, carbamazepine, pregabalin, and gabapentin (Neurontin™). Treatment for alcoholism is preferably administered in combination with behavioral therapy including such components as motivational enhancement therapy, cognitive behavioral therapy, and referral to self-help groups, including Alcohol Anonymous (AA). In addition to Zyban, other useful nicotine receptor partial agonists are described in U.S. Pat. Nos. 6,235,734; 6,410,550; and 6,462,035; all of which are incorporated herein by reference.

Other pharmaceutical agents that may be used in combination include antidepressants (e.g., fluoxetine hydrochloride (Prozac™)); and neuroprotective agents (e.g., memantine).

In another embodiment, compounds of the present invention are used in combination with cognitive improvement agents such as donepezil hydrochloride (Aricept™) and other acetylcholinesterase inhibitors; cannabinoid receptor 1 (CB1) antagonists; and alpha 7 nicotinic acetylcholine receptor agonists. Representative alpha 7 agonist compounds are listed in U.S. Pat. Nos. 6,911,543; 6,809,094; and 6,881,734, all of which are incorporated herein by reference.

According to a yet further aspect, the present invention additionally provides a method for the treatment and/or prevention of male sexual dysfunction via treatment with a combination of a compound of the present invention and at least one additional pharmaceutical agent. Preferred additional pharmaceutical agents used in treating male sexual dysfunction (e.g., male erectile dysfunction) include: (1) one or more dopaminergic agents (e.g. D2, D3 or D4 agonists and apomorphine); (2) one or more of an NPY (neuropeptide Y) (preferably an NPY-1 and/or NPY-5 inhibitor); (3) one or more of a melanocortin receptor agonist or modulator or melanocortin enhancer; (4) one or more of an NEP inhibitor; (5) one or more of a PDE inhibitor (preferably, a cGMP PDE-5 inhibitor); and (6) one or more of a bombesin receptor antagonist or modulator.

According to another aspect of the present invention, there is provided use of a compound of the present invention and one or more additional active agents for the treatment of female sexual dysfunction (FSD). Preferably, the one or more additional active agents is/are selected from the group consisting of: estrogen receptor modulators (e.g., estrogen agonists and/or estrogen antagonists); testosterone replacement agents and/or testosterone (Tostrelle) and/or dihydrotestosterone and/or dehydroepiandrosterone (DHEA) and/or a testosterone implant; estrogen, estrogen and medroxyprogesterone or medroxyprogesterone acetate (MPA) (as a combination), or a combination of estrogen and a methyl testosterone hormone replacement therapy agent; one or more dopaminergic agents; one or more NPY (neuropeptide Y) inhibitors; one or more melanocortin receptor modulators or melanocortin enhancers; one or more NEP (neutral endopeptidase) inhibitors; one or more PDE (phosphodiesterase) inhibitors; and one or more bombesin receptor modulators.

In another aspect, the compounds of the invention can be used in combination with other agents for the treatment of lower urinary tract dysfunction. Such other agents include: muscarinic acetylcholine receptor antagonists such as tolterodine; alpha adrenergic receptor antagonists, in particular an alpha1 adrenergic receptor antagonist or an alpha2 adrenergic receptor antagonist; alpha adrenergic receptor agonists or partial agonists, in particular an alpha1 adrenergic receptor agonist or partial agonist, or an alpha2 adrenergic receptor agonist or partial agonist; serotonin and noradrenalin reuptake inhibitor (SNRI); noradrenalin reuptake inhibitor (NRI) such as reboxetine, either in its racemic or (S,S)-enantiomeric form; vanilloid receptor (VR) antagonists, such as capsaicin; alpha2delta ligand, such as gabapentin or pregabalin; beta3 adrenergic-receptor agonists; 5HT1a receptor antagonists or 5HT1a receptor inverse agonists; prostanoid receptor antagonists, e.g. EP1 receptor antagonist.

The dosage of the additional pharmaceutical agent will be generally dependent upon a number of factors including the health of the subject being treated, the extent of treatment desired, the nature and kind of concurrent therapy, if any, and the frequency of treatment and the nature of the effect desired. The determination of dosage ranges and optimal dosages for a particular patient is also well within the ability of one of ordinary skill in the art having the benefit of the instant disclosure.

The present invention also relates to a method of treating a mammal suffering from schizophrenia or psychoses, comprising administering a compound of Formula I, or a pharmaceutically acceptable salt thereof, in an amount that is effective in treating schizophrenia or psychoses, and an antipsychotic drug or pharmaceutically acceptable salt thereof. The compound of Formula I and the antipsychotic drug may be administered together or separately, simultaneously or at separate intervals. An embodiment of the present invention provides a pharmaceutical composition comprising a compound of the formula I, or a pharmaceutically acceptable salt thereof, and an antipsychotic drug or pharmaceutically acceptable salt thereof.

The antipsychotic drug may be, for example, Chlorpromazine, Fluphenazine, Haloperidol, Loxapine, Mesoridazine, Molindone, Perphenazine, Pimozide, Thioridazine, Thiothixene, or Trifluoperazine. These drugs all have an affinity for the dopamine 2 receptor. The antipsychotic drug may also be, for example, Asenapine, Ziprasidone, Olanzapine, Clozapine, Risperidone, Sertindole, Quetiapine, Aripiprazole or Amisulpride.

The combinations may result in synergistic action allowing a lower dose of the atypical antipsychotic to be administered while achieving at least the same psychotropic effect as achieved with a standard dose of the atypical antipsychotic. The dosage of the atypical antipsychotic may be reduced by about 25-90%, for example, about 40-80% and typically about 50-70%. The reduction in amount of antipsychotic required will be dependent on the amount of the compound of Formula I given.

The selection of the dosage of each therapeutic agent is that which can provide relief to the patient as measured by a reduction or amelioration of symptoms associated with the disorder or condition of the patient. As is well known, the dosage of each component depends on several factors such as the potency of the selected specific compound, the mode of administration, the age and weight of the patient, the severity of the condition to be treated, and the like. Determining a dose is within the skill of the ordinary artisan. To the extent necessary for completeness, the synthesis of the components of the compositions and dosages are as described in the listed patents above or the Physicians' Desk Reference, 57th ed., Thompson, 2003 which are expressly incorporated herein by reference. Desirably, when ziprasidone is selected as the active agent, the daily dose contains from about 5 mg to about 460 mg. More preferably, each dose of the first component contains about 20 mg to about 320 mg of the ziprasidone, and even more preferably, each dose contains from about 20 mg to about 160 mg of ziprasidone. Pediatric dosages may be less such as for example in the range of about 0.5 mg to about 40 mg daily. This dosage form permits the full daily dosage to be administered in one or two oral doses, for example.

General outlines of the dosages for the atypical antipsychotics, and some preferred dosages, are provided herein. This list is not intended to be complete but is merely a guideline for any of the desired combinations of the present invention.

Olanzapine: from about 0.25 to about 100 mg, once/day; preferably, from about 1 to about 30 mg, once/day; and most preferably about 1 to about 25 mg once/day; Clozapine: from about 12.5 to about 900 mg daily; preferably, from about 150 to about 450 mg daily; Risperidone: from about 0.25 to about 16 mg daily; preferably, from about 2-8 mg daily; Sertindole: from about 0.0001 to about 1.0 mg/kg daily; Quetiapine: from about 1.0 to about 40 mg/kg given once daily or in divided doses; Asenapine: from about 0.005 to about 60 mg total per day, given as a single dose or in divided doses; Paliperidone: from about 0.01 mg/kg to about 4 mg/kg body weight, more preferably from about 0.04 to about 2 mg/kg body weight; Bifeprunox.

A preferred atypical antipsychotic used according to the invention is ziprasidone. Ziprasidone (5-[2-[4-(1,2-benzisothiazol-3-yl)piperazin-1-yl]ethyl]-6-chloroindolin-2-one) is a benzisothiazolyl piperazine atypical antipsychotic with in vitro activity as a $5\text{-HT}_{1A}$ receptor agonist and an inhibitor of serotonin and norepinephrine reuptake (U.S. Pat. No. 4,831,031). The postsynaptic $5\text{-HT}_{1A}$ receptor has been implicated in both depressive and anxiety disorders (N M Barnes, T Sharp, 38 Neuropharmacology 1083-152, 1999). Oral bioavailability of ziprasidone taken with food is approximately 60%, half-life is approximately 6-7 hours, and protein binding is extensive.

Ziprasidone is efficacious for the treatment of patients with schizophrenia and schizomood disorders, refractory schizophrenia, cognitive impairment in schizophrenia, affective and anxiety symptoms associated with schizoaffective disorder and bipolar disorder. The drug is considered a safe and efficacious atypical antipsychotic (Charles Caley & Chandra Cooper, 36 *Ann. Pharmacother.*, 839-51; (2002).

The present invention is useful in treating mental disorders and conditions, the treatment of which is facilitated by the administration of ziprasidone. Thus, the present invention has application where ziprasidone use is indicated as, e.g., in U.S. Pat. Nos. 6,245,766; 6,245,765; 6,387,904; 5,312,925; 4,831, 031; and European EP 0901789 published Mar. 17, 1999, all of which are incorporated herein by reference.

Other atypical antipsychotics which can be used include, but are not limited to:

Olanzapine, 2-methyl-4-(4-methyl-1-piperazinyl)-10H-thieno[2,3-b][1,5]-benzodiazepine. Olanizapine is a known compound and is described in U.S. Pat. No. 5,229,382 as being useful for the treatment of schizophrenia, schizophreniform disorder, acute mania, mild anxiety states, and psychosis. U.S. Pat. No. 5,229,382 is herein incorporated herein by reference in its entirety;

Clozapine, 8-chloro-11-(4-methyl-1-piperazinyl)-5H-dibenzo[b,e][1,4]diazepine. Clozapine is described in U.S. Pat. No. 3,539,573, which is herein incorporated by reference in its entirety. Clinical efficacy in the treatment of schizophrenia is described (Hanes, et al., Psychopharmacol. Bull., 24, 62 (1988));

Risperidone, 3-[2-[4-(6-fluoro-1,2-benzisoxazol-3-yl)piperidino]ethyl]-2-methyl-6,7,8,9-tetrahydro-4H-pyrido-[1,2-a]pyrimidin-4-one. Risperidone and its use in the treatment of psychotic diseases are described in U.S. Pat. No. 4,804,663, which is herein incorporated by reference in its entirety;

Sertindole, 1-[2-[4-[5-chloro-1-(4-fluorophenyl)-1H-indol-3-yl]-1-piperidinyl]ethyl]-imidazolidin-2-one. Sertindole is described in U.S. Pat. No. 4,710,500. Its use in the treatment of schizophrenia is described in U.S. Pat. Nos. 5,112,838 and 5,238,945. U.S. Pat. Nos. 4,710,500; 5,112,838; and 5,238,945 are herein incorporated by reference in their entireties;

Quetiapine, 5-[2-(4-dibenzo[b,f][1,4]thiazepin-11-yl-1-piperazinyl)ethoxy]ethanol. Quetiapine and its activity in assays which demonstrate utility in the treatment of schizophrenia are described in U.S. Pat. No. 4,879,288, which is herein incorporated by reference in its entirety. Quetiapine is typically administered as its (E)-2-butenedioate (2:1) salt.

Aripiprazole, 7-{4-[4-(2,3-dichlorophenyl)-1-piperazinyl]-butoxy}-3-,4-dihydro carbostyril or 7-{4-[4-(2,3-dichlorophenyl)-1-piperazinyl]-butoxy}-3,4-dihydro-2(1H)-quinolinone. Aripiprazole is an atypical antipsychotic agent used for the treatment of schizophrenia and described in U.S. Pat. Nos. 4,734,416 and 5,006,528, which are herein incorporated by reference in their entireties.

Amisulpride, which is described in U.S. Pat. No. 4,401,822. U.S. Pat. No. 4,401,822 is incorporated herein in its entirety.

Asenapine, trans-5-chloro-2-methyl-2,3,3a,12b-tetrahydro-1H-dibenz[2,3:6,7]-oxepino[4,5-c]pyrrole. Preparation and use of asenapine is described in U.S. Pat. Nos. 4,145,434 and 5,763,476, the entire contents of which are incorporated herein by reference.

Paliperidone, 3-[2-[4-(6-fluoro-1,2-benzisoxazol-3-yl)-1-piperidinyl]ethyl]-6,7,8,9-tetrahydro-9-hydroxy-2-methyl-4H-pyrido[1,2-a]pyrimidin-4-one. Preparation and use of paliparidone is described, for example, in U.S. Pat. Nos. 6,320,048; 5,158,952; and 5,254,556, the entire contents of which are incorporated herein by reference.

Bifeprunox, 2-[4-[4-(5-fluoro-1H-indol-3-yl)-3,6-dihydro-1(2H)-pyridinyl]butyl]-1H-isoindole-1,3(2H)-dione. Preparation and use of bifeprunox is described in U.S. Pat. No. 6,225,312, which is incorporated in its entirety herein.

A preferred combination is ziprasidone with a compound of Formula I or pharmaceutically acceptable salt thereof of the present invention.

The present invention includes each of the following compounds, as well as pharmaceutically acceptable salts of the compounds, and solvates or hydrates of the compounds or salts:

(7S)-7-[(2,5-difluorobenzyl)oxy]-2-piperazin-1-yl-6,7-dihydro-5H-cyclopenta[b]pyridine;
(7S)-7-[(3-fluorobenzyl)oxy]-2-[(2R)-2-methylpiperazin-1-yl]-6,7-dihydro-5H-cyclopenta[b]pyridine;
(7S)-7-[(2-chlorobenzyl)oxy]-2-[(2R)-2-methylpiperazin-1-yl]-6,7-dihydro-5H-cyclopenta[b]pyridine;
3-[({(7S)-2-[(2R)-2-methylpiperazin-1-yl]-6,7-dihydro-5H-cyclopenta[b]pyridin-7-yl}oxy)methyl]benzonitrile;
(7S)-7-[(2,5-difluorobenzyl)oxy]-2-[(2R)-2-methylpiperazin-1-yl]-6,7-dihydro-5H-cyclopenta[b]pyridine;
(7S)-7-[(2,5-dichlorobenzyl)oxy]-2-[(2R)-2-methylpiperazin-1-yl]-6,7-dihydro-5H-cyclopenta[b]pyridine;
(7S)-7-[(2-chloro-5-fluorobenzyl)oxy]-2-[(2R)-2-methylpiperazin-1-yl]-6,7-dihydro-5H-cyclopenta[b]pyridine;
(7S)-7-[(2-methyl-5-chlorobenzyl)oxy]-2-[(2R)-2-methylpiperazin-1-yl]-6,7-dihydro-5H-cyclopenta[b]pyridine;
(7S)-7-[(5-fluoro-2-methyl-benzyl)oxy]-2-[(2R)-2-methylpiperazin-1-yl]-6,7-dihydro-5H-cyclopenta[b]pyridine;
4-methyl-3-[({(7S)-2-[(2R)-2-methylpiperazin-1-yl]-6,7-dihydro-5H-cyclopenta[b]pyridin-7-yl}oxy)methyl]benzonitrile;
(7S)-7-(2-chlorophenoxy)-2-piperazin-1-yl-6,7-dihydro-5H-cyclopenta[b]pyridine;
(7S)-7-(3-chlorophenoxy)-2-piperazin-1-yl-6,7-dihydro-5H-cyclopenta[b]pyridine;
3-{[(7S)-2-piperazin-1-yl-6,7-dihydro-5H-cyclopenta[b]pyridin-7-yl]oxy}benzonitrile;
3-{[(7R)-2-piperazin-1-yl-6,7-dihydro-5H-cyclopenta[b]pyridin-7-yl]oxy}benzonitrile;
(7R)-7-(3,5-difluorophenoxy)-2-piperazin-1-yl-6,7-dihydro-5H-cyclopenta[b]pyridine;
(7S)-7-(2,3-dihydro-1H-inden-4-yloxy)-2-piperazin-1-yl-6,7-dihydro-5H-cyclopenta[b]pyridine;
(7S)-7-[(6-fluoro-2,3-dihydro-1H-inden-4-yl)oxy]-2-piperazin-1-yl-6,7-dihydro-5H-cyclopenta[b]pyridine;
(7S)-7-(1-naphthyloxy)-2-piperazin-1-yl-6,7-dihydro-5H-cyclopenta[b]pyridine;
5-{[(7S)-2-piperazin-1-yl-6,7-dihydro-5H-cyclopenta[b]pyridin-7-yl]oxy}isoquinoline;
8-{[(7S)-2-piperazin-1-yl-6,7-dihydro-5H-cyclopenta[b]pyridin-7-yl]oxy}quinoline;
8-{[(7S)-2-piperazin-1-yl-6,7-dihydro-5H-cyclopenta[b]pyridin-7-yl]oxy}quinoline-2-carbonitrile;
4-{[(7S)-2-piperazin-1-yl-6,7-dihydro-5H-cyclopenta[b]pyridin-7-yl]oxy}-1,3-benzoxazole;
7-(2-chlorophenoxy)-2-[(2R)-2-methylpiperazin-1-yl]-6,7-dihydro-5H-cyclopenta[b]pyridine;
(7S)-7-(2,3-dihydro-1H-inden-4-yloxy)-2-[(2R)-2-methylpiperazin-1-yl]-6,7-dihydro-5H-cyclopenta[b]pyridine;
(7S)-7-(6-fluoro-2,3-dihydro-1H-inden-4-yloxy)-2-[(2R)-2-methylpiperazin-1-yl]-6,7-dihydro-5H-cyclopenta[b]pyridine;
4-{[(7S)-2-piperazin-1-yl-6,7-dihydro-5H-cyclopenta[b]pyridin-7-yl]oxy}isoquinoline;
8-(2-fluorophenoxy)-2-piperazin-1-yl-5,6,7,8-tetrahydroquinoline;
(8S)-8-(3-fluorophenoxy)-2-piperazin-1-yl-5,6,7,8-tetrahydroquinoline;
3-{[(8R)-2-piperazin-1-yl-5,6,7,8-tetrahydroquinolin-8-yl]oxy}benzonitrile;
3-{[(8S)-2-piperazin-1-yl-5,6,7,8-tetrahydroquinolin-8-yl]oxy}benzonitrile;
(8S)-8-(5-fluoro-2-methylphenoxy)-2-piperazin-1-yl-5,6,7,8-tetrahydroquinoline;
(8S)-8-(2-chloro-5-methylphenoxy)-2-piperazin-1-yl-5,6,7,8-tetrahydroquinoline;

(8S)-8-(3,5-difluorophenoxy)-2-piperazin-1-yl-5,6,7,8-tetrahydroquinoline; and (8S)-8-(3-chloro-2-fluorophenoxy)-2-piperazin-1-yl-5,6,7,8-tetrahydroquinoline;

(8S)-8-(2,3-dihydro-1H-inden-4-yloxy)-2-piperazin-1-yl-5,6,7,8-tetrahydroquinoline;

(8S)-8-(6-fluoro-2,3-dihydro-1H-inden-4-yloxy)-2-piperazin-1-yl-5,6,7,8-tetrahydroquinoline;

(8S)-8-(6-fluoro-2,3-dihydro-1H-inden-4-yloxy)-2-[(2R)-2-methylpiperazin-1-yl]-5,6,7,8-tetrahydroquinoline;

3-Chloro-7(S)-(2,5-difluoro-benzyloxy)-2-(2-(R)-methyl-piperazin-1-yl)-6,7-dihydro-5H-[1]-pyridine;

3-Chloro-7-(5-fluoro-2-methyl-benzyloxy)-2-(2-methyl-piperazin-1-yl)-6,7-dihydro-5H-[1]pyridine;

3-[3-Chloro-2-(2-methyl-piperazin-1-yl)-6,7-dihydro-5H-[1]pyridin-7-yloxymethyl]-4-methyl-benzonitrile;

3-Chloro-8-(2,3-dichloro-phenoxy)-2-piperazin-1-yl-5,6,7,8-tetrahydro-quinoline;

3-Chloro-8-(2-fluoro-phenoxy)-2-piperazin-1-yl-5,6,7,8-tetrahydro-quinoline;

3-Chloro-8-(5-fluoro-2-methyl-phenoxy)-2-piperazin-1-yl-5,6,7,8-tetrahydro-quinoline;

3-Chloro-8-(3,5-difluoro-phenoxy)-2-piperazin-1-yl-5,6,7,8-tetrahydro-quinoline;

3-Chloro-8-(3-fluoro-phenoxy)-2-piperazin-1-yl-5,6,7,8-tetrahydro-quinoline;

3-Chloro-8-(3-chloro-2-fluoro-phenoxy)-2-piperazin-1-yl-5,6,7,8-tetrahydro-quinoline;

3-Chloro-7-(2-chloro-phenoxy)-2-piperazin-1-yl-6,7-dihydro-5H-[1]pyridine; and

3-Chloro-7-(3-chloro-phenoxy)-2-piperazin-1-yl-6,7-dihydro-5H-[1]pyridine.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

Unless specified otherwise, starting materials are generally available from commercial sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), and AstraZeneca Pharmaceuticals (London, England).

General Experimental Procedures

NMR spectra were recorded on a Varian Unity™ 400 (available from Varian Inc., Palo Alto, Calif.) at room temperature at 400 MHz for proton. Chemical shifts are expressed in parts per million (δ) relative to residual solvent as an internal reference. The peak shapes are denoted as follows: s, singlet; d, doublet; t, triplet; q, quartet; m, multiplet; br s, broad singlet; 2 s, two singlets. Atmospheric pressure chemical ionization mass spectra (APCI) were obtained on a Fisons™ Platform II Spectrometer (carrier gas: acetonitrile: available from Micromass Ltd, Manchester, UK). Chemical ionization mass spectra (CI) were obtained on a Hewlett-Packard™ 5989 instrument (ammonia ionization, PBMS: available from Hewlett-Packard Company, Palo Alto, Calif.). Electrospray ionization mass spectra (ES) were obtained on a Waters™ ZMD instrument (carrier gas: acetonitrile: available from Waters Corp., Milford, Mass.). Where the intensity of chlorine or bromine-containing ions are described, the expected intensity ratio was observed (approximately 3:1 for $^{35}Cl/^{37}Cl$-containing ions and 1:1 for $^{79}Br/^{81}Br$-containing ions) and the intensity of only the lower mass ion is given. In some cases only representative $^1H$ NMR peaks are given. MS peaks are reported for all examples. Optical rotations were determined on a PerkinElmer™ 241 polarimeter (available from PerkinElmer Inc., Wellesley, Mass.) using the sodium D line (λ=589 nm) at the indicated temperature and are reported as follows $[\alpha]_D^{temp}$, concentration (c=g/100 mL), and solvent.

Column chromatography was performed with either Baker™ silica gel (40 μm; J. T. Baker, Phillipsburg, N.J.) or Silica Gel 50 (EM Sciences™, Gibbstown, N.J.) in glass columns or in Flash 40 Biotage™ columns (ISC, Inc., Shelton, Conn.) under low nitrogen pressure.

Preparative thin-layer chromatography was performed using Analtech silica gel GF with UV254 indicator (Analtech Inc., Newark, Del.) 20 cm×20 cm×1 mm plates. When needed multiple plates are used. After eluting the plates with the indicated solvent, the desired band is marked under UV light, and scrapped off. The desire product is extracted from the silica using the designated solvent.

Racemic compounds or enantio-enriched compounds were separated on a Chiralpak™ AD column (dimension 4.6 mm×25 cm). Chiralpak™ AD columns are available from Daicel™.

As used herein, the following acronyms have the corresponding meanings.

TFA—trifluoroacetic acid
THF—tetrahydrofuran
TLC—thin layer chromatography
DMF—dimethylformamide
BOC—tert-butoxycarbonyl
dba—dibenz[a,h]anthracene
BINAP—2,2'-bis(diphenylphosphino)-1,1'-binaphthyl
DEAD—diethyl azodicarboxylate Preparation of Intermediates Preparation of Intermediate
2-chloro-6,7-dihydro-5H-cyclopenta[b]pyridine
N-oxide (I-1a)

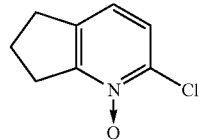

I-1a

A solution of m-chloroperbenzoic acid 70% (520.9 mg, 2.113 mmol) in 5 mL of $CH_2Cl_2$ was added drop wise to a stirring solution of 2-chloro-6,7-dihydro-5H-cyclopenta[b]pyridine (295 mg, 1.921 mmol) in 3 mL of $CH_2Cl_2$ and the resulting solution was allowed to stir at room temperature overnight. The reaction mixture was quenched with a saturated aqueous solution of $NaHCO_3$ and the $CH_2Cl_2$ layer was separated. The aqueous phase was then extracted with $CH_2Cl_2$ (3x), and the combined organic extracts were washed with brine and then dried over anhydrous $Na_2SO_4$. After removing solvent at reduced pressure, the residue was purified by preparative TLC (eluting with 70% EtOAc/Hexane) to afford the title compound (I-1a).

MS calculated=169.91, MS+1 observed=170.0

Preparation of Intermediate 2-chloro-6,7-dihydro-5H-cyclopenta[b]pyridin-7-yl acetate (I-1b)

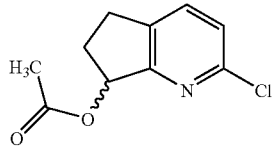

I-1b

In round bottom flask equipped with a condenser, intermediate (I-1a: 249.7 mg, 1.472 mmol) was dissolved in 6 mL acetic anhydride and heated at 110° C. overnight. The reaction mixture was allowed to cool and the solvent was removed under reduced pressure. The resulting residue was dissolved up in $CH_2Cl_2$, and washed successively with saturated aqueous solution of $NaHCO_3$ (2×) and brine (1×). After drying over anhydrous $Na_2SO_4$, the solution was removed under reduce pressure and purified by preparative TLC (eluting with 20% EtOAc/Hexane) to afford the title compound (I-1b).

MS calculated=211.65, MS+1 observed=212.0

Racemic acetate was separated on column Chiralpak AS (dimension 4.6 mm×25 cm). The mobile phase contained 85% heptane and 15% EtOH without modifier. The flow rate was set at 1 mL/minute.

7(S)2-chloro-6,7-dihydro-5H-cyclopenta[b]pyridin-7-yl acetate:

MS calculated=211.65, MS+1 observed=212.0

7(R)2-chloro-6,7-dihydro-5H-cyclopenta[b]pyridin-7-yl acetate:

MS calculated=211.65, MS+1 observed=212.0

Preparation of Intermediate 2-chloro-6,7-dihydro-5H-cyclopenta[b]pyridin-7-ol (I-1c)

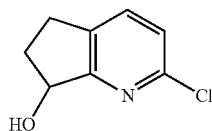

I-1c

To a solution of intermediate I-1b (233.6 mg, 1.104 mmol) in 3.7 mL methanol, was added a 10% $K_2CO_3$ aqueous solution (366 mg, 2.649 mmol, 3.7 mL $H_2O$) and the mixture was allowed to stir at room temperature overnight. The reaction mixture was extracted with $CH_2Cl_2$ (5×), washed with brine and dried over anhydrous $MgSO_4$. After removing solvent under reduced pressure, the residue was purified by preparative TLC (eluting with 25% EtOAc/Hexane) to afford the title compound (I-1c).

MS calculated=169.91, MS+1 observed=170.0

Preparation of Intermediate 2-[4-(2,2-dimethylpropanoyl)piperazin-1-yl]-6,7-dihydro-5H-cyclopenta[b]pyridin-7-ol (I-1d)

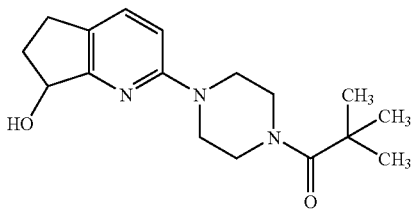

I-1d

Intermediate I-1c (163.0 mg, 0.961 mmol), piperazine-1-carboxylic acid tert-butyl ester (232.6 mg, 1.249 mmol), $Pd_2(dba)_3$ (17.6 mg, 0.0192 mmol), BINAP (23.9 mg, 0.0384 mmol), and sodium t-butoxide (129.3 mg, 1.346 mmol) was added to a pre-dried reaction vial under a nitrogen atmosphere. After dissolving in 3 mL anhydrous toluene, the reaction mixture was stirred and heated at 80° C. overnight. After cooling, the reaction was filtered through celite, washed with EtOAc, and the solvent was removed in vacuo. The residue was purified by preparative TLC (eluting with 40% EtOAc/Hexane) to afford 100 mg (14.8% yield for 4-step synthesis) of the title compound (I-1d).

MS calculated=319.41, MS+1 observed=320.2

Preparation of Intermediate (7S)-2-chloro-7-[(3-fluorobenzyl)oxy]-6,7-dihydro-5H-cyclopenta[b]pyridine (I-2a)

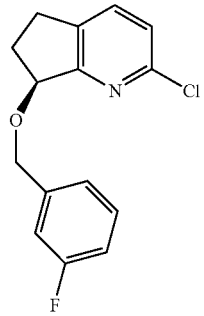

I-2a

The (S) enantiomer of Intermediate I-1c (30.0 mg, 0.177 mmol), 1-bromomethyl-3-fluoro-benzene (57 mg, 0.301 mol), sodium hydride 60% (28 mg, 0.707 mmol), and tetrabutylammonium iodide (0.7 mg, $1.77 \times 10^{-3}$ mmol) was added to a predried vial under $N_2$ atmosphere. The reagents were then dissolved in 2 mL anhydrous DMF and stirred at room temperature overnight. Water was added to the reaction mixture and then extracted with EtOAc (3×). The combined organic extracts were washed successively with $H_2O$ (2×) and brine (1×), and then dried over anhydrous $MgSO_4$. The solvent was removed in vacuo and the residue was purified by preparative TLC (eluting with 20% EtOAc/Hexane) to afford the title compound (I-2a). The (S) enantiomer of Intermediate I-1c used to synthesize this compound was obtained as described in the preparation of 1-1c, although the starting material was the (S) enantiomer of Intermediate I-1b which was obtained as described in the preparation of 1-1b.

Preparation of Intermediate (7S)-2-chloro-7-(2,3-dichlorophenoxy)-6,7-dihydro-5H-cyclopenta[b]pyridine (I-3a)

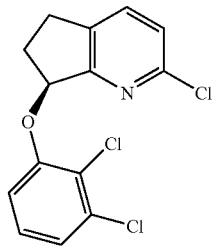

I-3a

The (R) enantiomer of Intermediate I-1c (30.0 mg, 0.177 mmol) and 2,3-dichloro-phenol (57.7 mg, 0.354 mmol) were dissolved up in 2 mL anhydrous THF in a predried reaction vial under a $N_2$ atmosphere. Polymer bound triphenylphosphine (154 mg, 2.3 mmol/g loaded, 0.354 mmol) was added and the mixture was allowed to stir at room temperature for 30 minutes. The reaction mixture was then cooled to 0° C., DEAD (40% in toluene, 161 µL, 0.354 mmol) was introduced, and then allowed to reach room temperature overnight. The resin was filtered off washing with THF, the solvent was removed in vacuo and the residue was purified by preparative TLC (eluting with 30% EtOAc/Hexane) to afford the title compound (I-3a). MS calculated=314.60, MS+1 observed=314.1

Example 1 illustrates the preparation of compounds of Formula (I) where m is 1, n is 1 and $R^2$ is hydrogen.

Example 1

Preparation of (7S)-7-[(2-ethylbenzyl)oxy]-2-piperazin-1-yl-6,7-dihydro-5H-cyclopenta[b]pyridine (1A-1)

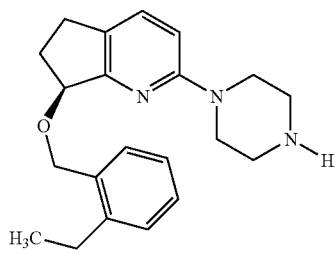

1A-1

Intermediate (S)-I-1d (25.0 mg, 0.0783 mmol), 1-bromomethyl-2-ethyl-benzene (26.5 mg, 0.133 mol), sodium hydride 60% (12.5 mg, 0.313 mmol), and tetrabutylammonium iodide (0.29 mg, 7.83×10⁻⁴ mmol) was added to a predried vial under a $N_2$ atmosphere. The reagents were dissolved in 0.6 mL anhydrous DMF and the reaction mixture was stirred at room temperature over weekend. Water was added to the mixture and then extracted with EtOAc (3×). The combined organic extracts were successively washed with $H_2O$ (2×) and brine (1×). After drying over anhydrous $MgSO_4$, the solvent was removed in vacuo and the residue was purified by preparative TLC (eluting with 20% EtOAc/ Hexane) to afford BOC-protected (7S)-7-[(2-ethylbenzyl) oxy]-2-piperazin-1-yl-6,7-dihydro-5H-cyclopenta[b]pyridine.

Trifluoroacetic acid (52.3 µL, 0.679 mmol) was added to a solution of the BOC-protected compound from above (29.7 mg, 0.0679 mmol) in 1.5 mL of $CH_2Cl_2$ and the mixture was allowed to stir at room temperature overnight. The solvent was removed in vacuo and the residue was purified by preparative TLC (eluting with 10% MeOH, 1% $NH_4OH$/ $CH_2Cl_2$) to yield 19.3 mg (73.0% for 2-step synthesis) of the title compound (1A-1).

MS calculated=337.47, MS+1 observed=338.2

1H NMR (400M Hz, $CD_3OD$): d 7.44 (d, 1H), 7.33 (d, 1H), 7.21-7.09 (m, 3H), 6.70 (d, 1H), 4.98 (d, 1H), 4.77 (m, 1H), 4.71 (d, 1H), 3.45 (m, 4H), 2.90 (m, 4H), 2.70-2.61 (m, 4H), 2.38-2.29 (m, 1H), 2.09-2.02 (m, 1H), 1.14 (t, 3H).

The compounds listed in Tables 1A, 1B and 1C below were prepared using procedures analogous to those described above for the synthesis of Compound 1A-1 using the appropriate starting materials which are available commercially, prepared using preparations well-known to those skilled in the art, or prepared in a manner analogous to routes described above for other intermediates. For those compounds that were prepared from a racemic intermediate, the racemic compound or enantio-enriched compound was separated on column Chiralpak AD (dimension 4.6 mm×25 cm). Mobile phase contained heptane and EtOH with TFA as modifier. The flow rate was set at 1 mL/min.

TABLE 1A

| Example No. | $R^{0a}$ | $R^1$ | MS Calc | MS Found (M + 1) |
|---|---|---|---|---|
| IA-1 | H | 2-ethyl-phenyl | 337.47 | 338.2 |
| 1A-2 | H | Phenyl | 309.41 | 310.2 |
| 1A-3 | H | naphthalen-1-yl | 359.47 | 360.2 |
| 1A-4 | H | quinolin-5-yl | 360.46 | 361.1 |
| 1A-5 | H | quinolin-8-yl | 360.46 | 361.1 |
| 1A-6 | H | 2-chloro-phenyl | 343.86 | 344.1 |
| 1A-7 | H | 3-chloro-phenyl | 343.86 | 344.1 |
| 1A-8 | H | 2-fluoro-phenyl | 327.40 | 328.2 |
| 1A-9 | H | 3-fluoro-phenyl | 327.40 | 328.2 |
| 1A-10 | H | 3-bromo-phenyl | 388.31 | 389.9 |
| 1A-11 | H | 2-methyl-phenyl | 323.44 | 324.4 |
| 1A-12 | H | 3-methyl-phenyl | 323.44 | 324.2 |
| 1A-13 | H | 2-isopropyl-phenyl | 351.49 | 352.1 |
| 1A-14 | H | 2-trifluoromethyl-phenyl | 377.41 | 378.2 |
| 1A-15 | H | 3-trifluoromethyl-phenyl | 377.41 | 378.2 |
| 1A-16 | H | 2-cyano-phenyl | 334.42 | 335.2 |
| 1A-17 | H | 3-cyano-phenyl | 334.42 | 335.2 |
| 1A-18 | H | 2-trifluoromethoxy-phenyl | 393.41 | 394.2 |
| 1A-19 | H | 3-trifluoromethoxy-phenyl | 393.41 | 394.2 |
| 1A-20 | H | 2-(2-fluoromethyl)-phenyl | 375.42 | 376.2 |
| 1A-21 | H | 3-(2-fluoromethyl)-phenyl | 375.42 | 376.2 |
| 1A-22 | H | 3-phenoxy-phenyl | 401.51 | 402.3 |
| 1A-23 | H | 3-benzyloxy-phenyl | 415.53 | 416.2 |
| 1A-24 | H | 3-(p-fluorophenoxy)-phenyl | 419.50 | 420.2 |
| 1A-25 | H | 3-(trifluoromethyl-thio)-phenyl | 409.47 | 410.1 |
| 1A-26 | H | biphenyl-2-yl | 385.51 | 386.2 |

TABLE 1A-continued

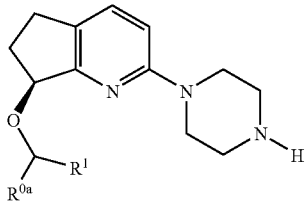

| Example No. | R^{0a} | R^1 | MS Calc | MS Found (M + 1) |
|---|---|---|---|---|
| 1A-27 | H | 4-(trifluoramethyl)biphenyl-2-yl | 453.51 | 454.2 |
| 1A-28 | H | 3-(6-bromo-2-chloro-pyrimidin4-amino)-phenyl | 515.84 | 515.1 |
| 1A-29 | H | 4-(N-methyl(methanesulfon-amido))-phenyl | 416.54 | 417.2 |
| 1A-30 | H | 2-(2,2,2-trifluoroacetamido)-phenyl | 420.43 | 421.2 |
| 1A-31 | H | pyrazol-1-yl-phenyl | 375.47 | 376.2 |
| 1A-32 | H | [1,2,4]triazol-1-yl-phenyl | 376.46 | 377.2 |
| 1A-33 | H | 3-benzamido | 352.44 | 353.2 |
| 1A-34 | H | 3-(N-methylbenzamido) | 366.46 | 367.2 |
| 1A-35 | N | 2,4-difluorophenyl | 345.39 | 346.2 |
| 1A-36 | H | 2,3-difluorophenyl | 345.39 | 346.2 |
| 1A-37 | H | 2,5-difluorophenyl | 345.39 | 346.0 |
| 1A-38 | H | 3,5-difluorophenyl | 345.39 | 346.2 |
| 1A-39 | H | 2,6-difluorophenyl | 345.39 | 346.2 |
| 1A-40 | H | 2,5-dichlorophenyl | 378.30 | 378.1 |
| 1A-41 | H | 2,6-dichlorophenyl | 378.30 | 378.1 |
| 1A-42 | H | 2,3-dichlorophenyl | 378.30 | 378.1 |
| 1A-43 | H | 2-chloro-6-fluorophenyl | 361.85 | 362.1 |
| 1A-44 | H | 3-chloro-2-fluorophenyl | 361.85 | 362.4 |
| 1A-45 | H | 2,3-dimethylphenyl | 337.46 | 338.2 |
| 1A-46 | H | 2,6-dimethylphenyl | 337.46 | 338.2 |
| 1A-47 | H | 3,5-dimethylphenyl | 337.46 | 338.2 |
| 1A-48 | H | 3,5-bis-trifluoromethyiphenyl | 445.41 | 446.1 |
| 1A-49 | H | 2,5-bis-trifluoromethylphenyl | 445.41 | 446.1 |
| 1A-50 | H | 3,5-dimethoxyphenyl | 369.46 | 370.2 |
| 1A-51 | H | 2,3-dimethoxyphenyl | 369.46 | 370.2 |
| 1A-52 | H | 3-fluoro-5-methylphenyl | 341.43 | 342.2 |
| 1A-53 | H | 2-fluoro-3-methylphenyl | 341.43 | 342.0 |
| 1A-54 | H | 5-fluoro-2-methylphenyl | 341.43 | 342.2 |
| 1A-55 | H | 3-fluoro-2-methylphenyl | 341.43 | 342.2 |
| 1A-56 | H | 5-chloro-2-methylphenyl | 357.88 | 358.2 |
| 1A-57 | H | 5-fluoro-2-trifluoromethyl-phenyl | 395.40 | 396.2 |
| 1A-58 | H | 2-fluoro-6-trifluoromethyl-phenyl | 395.40 | 396.2 |
| 1A-59 | H | 2-fluoro-3-trifluoromethyl-phenyl | 395.40 | 396.2 |
| 1A-60 | H | 3-fluoro-2-trifluoromethyl-phenyl | 395.40 | 396.2 |
| 1A-61 | H | 2-chloro-5-trifluoromethyl-phenyl | 411.85 | 412.1 |
| 1A-62 | H | 2-chloro-5-methoxy-phenyl | 373.88 | 374.1 |
| 1A-63 | H | 2-methoxy-5-acetyl-phenyl | 381.47 | 382.2 |
| 1A-64 | H | 4'-chloro-4-methoxy-biphenyl | 449.98 | 450.2 |
| 1A-65 | H | 2,3,5-trifluorophenyl | 363.38 | 364.1 |
| 1A-66 | H | 2-chloro-3,6-difluorophenyl | 379.84 | 380.1 |
| 1A-67 | H | 2-ethyl-3,5-difluorophenyl | 373.44 | 374.1 |
| 1A-68 | H | 2-methyl-3,5-difluorophenyl | 359.42 | 360.2 |
| 1A-69 | H | 6-fluoro-4H-benzo[1,3]dioxin-8-yl | 385.44 | 386.2 |
| 1A-70 | H | 6,7-dichloro-4H-benzo[1,3]-dioxin-8-yl | 436.34 | 436.1 |
| 1A-71 | CH₃ | 2-chlorophenyl | 357.88 | 358.0 |
| 1A-72 | (S)CH₃ | 2-chlorophenyl | 357.88 | 358.0 |
| 1A-73 | (R)CH₃ | 2-chlorophenyl | 357.88 | 358.0 |
| 1A-74 | CH₃ | 3-chlorophenyl | 357.88 | 358.0 |
| 1A-75 | CH₃ | 2-fluorophenyl | 341.43 | 342.1 |

TABLE 1A-continued

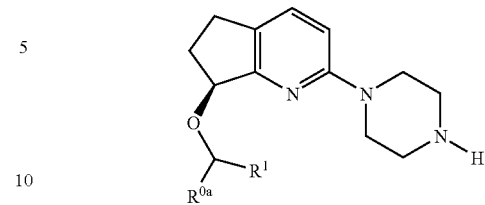

| Example No. | R^{0a} | R^1 | MS Calc | MS Found (M + 1) |
|---|---|---|---|---|
| 1A-76 | CH₃ | 3-fluorophenyl | 341.43 | 342.1 |
| 1A-77 | CH₃ | 2-methylphenyl | 337.46 | 338.1 |
| 1A-78 | CH₃ | 3-methylphenyl | 337.46 | 338.1 |
| 1A-79 | H | pyridin-3-yl | 310.40 | 311.2 |
| 1A-80 | H | pyridin-6-yl | 310.40 | 311.2 |
| 1A-81 | H | 3,5-dimethyl-isoxazol-4-yl | 328.41 | 329.2 |
| 1A-82 | H | 6-chloro-pyridin-3-yl | 344.84 | 345.1 |
| 1A-83 | H | 3-methyl-pyridin-2-yl | 324.43 | 325.2 |
| 1A-84 | H | 3-(N-morpholin4-yl-benzamido) | 437.54 | 438.2 |

TABLE 1B

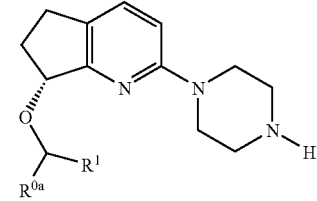

| Example No. | R^{0a} | R^1 | MS Calc | MS Found (M + 1) |
|---|---|---|---|---|
| 1B-1 | CH₃ | 3-chlorophenyl | 357.88 | 358.4 |
| 1B-2 | CH₃ | 2-chlorophenyl | 357.88 | 358.4 |

TABLE 1C

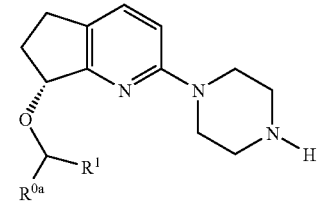

| Example No. | R^{0a} | R^1 | MS Calc | MS Found (M + 1) |
|---|---|---|---|---|
| IC-1 | H | 2-chloro-phenyl | 343.86 | 344.1 |
| IC-2 | H | 3-chloro-phenyl | 343.86 | 344.1 |
| IC-3 | H | 4-chloro-phenyl | 343.86 | 344.1 |
| IC-4 | H | 2-fluoro-phenyl | 419.50 | 420.2 |
| IC-5 | H | 2-bromo-phenyl | 388.31 | 389.9 |
| IC-6 | H | 2-cyano-phenyl | 334.42 | 335.2 |
| IC-7 | H | 3-cyano-phenyl | 334.42 | 335.1 |
| IC-8 | H | 4-cyano-phenyl | 334.42 | 335.1 |
| IC-9 | H | 2-methoxy-phenyl | 339.44 | 340.4 |

Example 2 illustrates the preparation of compounds of Formula (I) where m is 1, n is 1 and $R^2$ is methyl.

Example 2

Preparation of (7S)-7-[(3-fluorobenzyl)oxy]-2-[(2R)-2-methylpiperazin-1-yl]-6,7-dihydro-5H-cyclopenta[b]pyridine (2A-1)

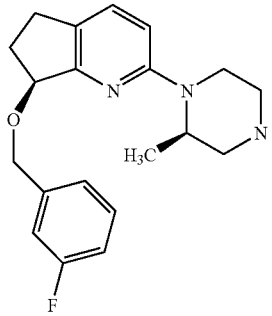

2A-1

Intermediate I-2a (47.1 mg, 0.169 mmol), (R)-3-methylpiperazine-1-carboxylic acid tert-butyl ester (43.9 mg, 0.220 mmol), $Pd_2(dba)_3$ (3.1 mg, 3.38×10$^{-3}$ mmol), BINAP (4.2 mg, 6.76×10$^{-3}$ mmol) and sodium t-butoxide (21.1 mg, 0.220 mmol) were added to a predried reaction vial under $N_2$ atmosphere. The reagents were then dissolved in 2 mL anhydrous toluene and allowed to stir at reflux overnight. The reaction mixture was allowed to cool and was then filtered through celite washing with EtOAc. The solvent was then remove in vacuo and the residue was purified by preparative TLC (eluting with 33% EtOAc/Hexane) to afford BOC-protected (7S)-7-[(3-fluorobenzyl)oxy]-2-[(2R)-2-methylpiperazin-1-yl]-6,7-dihydro-5H-cyclopenta[b]pyridine.

Trifluoroacetic acid (150 μL) was added to a solution of the BOC-protected compound from above (36.8 mg, 0.0833 mmol) in 2 mL of $CH_2Cl_2$ and the reaction mixture was allowed to stir at room temperature overnight. The solvent was removed in vacuo and the residue was purified by preparative TLC (eluting with 10% MeOH/$CH_2Cl_2$). After removing the desired band from the plate, it was stirred in a solution of 10% MeOH, 1% $NH_4OH/CH_2Cl_2$ to neutralize any product in TFA salt state. The title compound (2A-1) was isolated to give 22.8 mg (37.7% for 3-step synthesis).

MS calculated=341.43, MS+1 observed=342.0 1H NMR (400M Hz, $CD_3OD$): d 7.47 (d, 1H), 7.32 (m, 1H), 7.16 (m, 2H), 6.95 (dt, 1H), 6.69 (d, 1H), 4.78 (m, 2H), 3.96 (M, 1H), 3.20-3.04 (m, 5H), 2.94-2.88 (M, 3H), 2.70-2.72 (m, 1H), 2.34-2.38 (m, 1H), 2.12-2.07 (m, 1H), 1.17 (d, 3H).

The compounds listed in Tables 2A and 2B below were prepared using procedures analogous to those described above for the synthesis of Compound 2A-1 using the appropriate starting materials which are available commercially, prepared using preparations well-known to those skilled in the art, or prepared in a manner analogous to routes described above for other intermediates. For those compounds that were prepared from a racemic intermediate, the racemic compound or enantio-enriched compound was separated on column Chiralpak AD (dimension 4.6 mm×25 cm). Mobile phase contained heptane and EtOH with TFA as modifier. The flow rate was set at 1 mL/min.

TABLE 2A

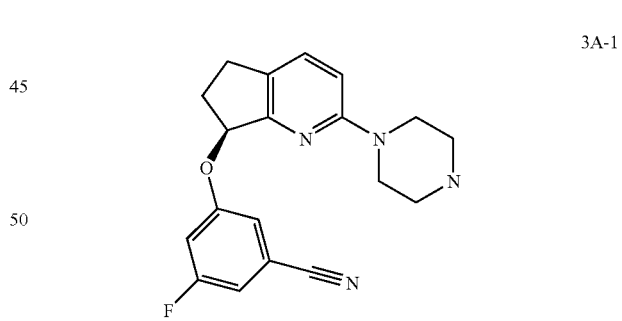

| Example No. | $R^{0a}$ | $R^1$ | MS Calc | MS Found (M + 1) |
|---|---|---|---|---|
| 2A-1 | H | 3-fluorophenyl | 341.43 | 342.0 |
| 2A-2 | H | 2-chlorophenyl | 357.88 | 358.0 |
| 2A-3 | H | 2-cyanophenyl | 348.45 | 349.0 |
| 2A-4 | H | 3-cyanophenyl | 348.45 | 349.0 |
| 2A-5 | H | 2-trifluoromethyl-phenyl | 391.43 | 392.0 |
| 2A-6 | H | 2,5-difluorophenyl | 359.42 | 360.1 |
| 2A-7 | H | 2,5-dichlorophenyl | 392.33 | 391.9 |
| 2A-8 | H | 2-chloro-5-fluorophenyl | 375.87 | 376.2 |
| 2A-9 | H | 5-fluoro-2-methylphenyl | 355.45 | 356.3 |
| 2A-10 | H | 5-chloro-2-methylphenyl | 371.91 | 372.0 |
| 2A-11 | H | 2-fluoro-5-trifluoromethyl-phenyl | 409.42 | 410.0 |
| 2A-12 | H | 5-fluoro-2-trifluoromethyl-phenyl | 409.42 | 410.0 |
| 2A-13 | H | 2-chloro-5-trifluoromethyl-phenyl | 425.88 | 426.0 |
| 2A-14 | H | 2-fluorophenyl | 341.43 | 342 |
| 2A-15 | H | 3-chlorophenyl | 357.88 | 358 |
| 2A-16 | H | 2-fluoro-5-chlorophenyl | 375.87 | 376.2 |
| 2A-17 | H | 2-fluoro-5-cyanophenyl | 366.43 | 367 |
| 2A-18 | H | 2-methyl-5-cyanophenyl | 362.47 | 363 |

Example 3 illustrates the preparation of compounds of Formula (I) where m is 1, n is 0 and $R^2$ is hydrogen.

Example 3

Preparation of 3-fluoro-5-{[(7S)-2-piperazin-1-yl-6,7-dihydro-5H-cyclopenta[b]pyridin-7-yl]oxy}benzonitrile (3A-1)

3A-1

Intermediate (R)-I-1d (20.0 mg, 0.0626 mmol) and 3-fluoro-5-hydroxy-benzonitrile (17.1 mg, 0.125) was dissolved in 1 mL anhydrous THF in a predried reaction vial under $N_2$ atmosphere. Polymer bound triphenylphosphine (57.1 mg, 2.19 mmol/g loaded, 0.125 mmol) was then added and the mixture allowed to stir at room temperature for 30 minutes. The reaction was cooled to 0° C., DEAD (40% in toluene, 56.8 μL, 0.125 mmol) was added, and reaction mixture was allowed to reach room temperature overnight. The resin was filtered off washing with THF, the solvent removed in vacuo, and then the residue was purified by preparative (eluting with TLC 20% EtOAc/Hexane) to afford the BOC-protected 3-fluoro-5-{[(7S)-2-piperazin-1-yl-6,7-dihydro-5H-cyclopenta[b]pyridin-7-yl]oxy}benzonitrile.

Trifluoroacetic acid (24.6 μL, 0.319 mmol) was added to a solution of the BOC-protected compound from above (14.0 mg, 0.0319 mmol) in 0.5 mL of $CH_2Cl_2$ and the mixture was stirred at room temperature overnight. The reaction solvent was removed in vacuo and the resulting residue was purified by preparative TLC (eluting with 10% MeOH, 1% $NH_4OH$/$CH_2Cl_2$) to yield 11.4 mg of the title compound 3A-1 (53.8% for 2-step synthesis).

MS calculated=338.39, MS+1 observed=339.2 1H NMR (400M Hz, $CD_3OD$): d 7.59 (s, 1H), 7.51 (d, 1H), 7.31 (d, 1H), 7.28 (d, 1H), 6.87 (m, 1H), 6.77 (d, 1H), 5.65 (m, 1H), 3.48 (m, 4H), 2.99 (m, 1H), 2.93 (m, 4H), 2.80 (m, 1H), 2.56 (m, 1H), 2.22 (m, 1H).

The compounds listed in Tables 3A, 3B and 3C below were prepared using procedures analogous to those described above for the synthesis of Compound 3A-1 using the appropriate starting materials which are available commercially, prepared using preparations well-known to those skilled in the art, or prepared in a manner analogous to routes described above for other intermediates. For those compounds that were prepared from a racemic intermediate, the racemic compound or enantio-enriched compound was separated on column Chiralpak AD (dimension 4.6 mm×25 cm). Mobile phase contained heptane and EtOH with TFA as modifier. The flow rate was set at 1 mL/min.

TABLE 3A

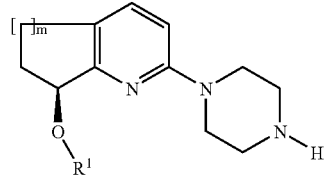

| Example No. | m | $R^1$ | MS Calc | MS Found (M + 1) |
|---|---|---|---|---|
| 3A-1 | 1 | 3-fluoro-5-benzonitrile | 338.39 | 339.2 |
| 3A-2 | 1 | 2-chlorophenyl | 329.83 | 330.1 |
| 3A-3 | 1 | 3-chlorophenyl | 329.83 | 330.1 |
| 3A-4 | 1 | 4-chlorophenyl | 329.83 | 330.1 |
| 3A-5 | 1 | 2-fluorophenyl | 313.37 | 314.1 |
| 3A-6 | 1 | 3-fluorophenyl | 313.37 | 314.1 |
| 3A-7 | 1 | 4-fluorophenyl | 313.37 | 314.1 |
| 3A-8 | 1 | 2-methylphenyl | 309.41 | 310.1 |
| 3A-9 | 1 | 2-ethylphenyl | 323.44 | 324.2 |
| 3A-10 | 1 | 2-(n-propyl)phenyl | 337.46 | 338.2 |
| 3A-11 | 1 | 3-methylphenyl | 309.41 | 310.1 |
| 3A-12 | 1 | 3-(iso-propyl)phenyl | 337.46 | 338.2 |
| 3A-13 | 1 | 4-methylphenyl | 309.41 | 310.1 |
| 3A-14 | 1 | 2-trifluoromethyl-phenyl | 363.38 | 364.1 |
| 3A-15 | 1 | 3-trifluoromethyl-phenyl | 363.38 | 364.1 |
| 3A-16 | 1 | 2-cyanophenyl | 320.39 | 321.1 |
| 3A-17 | 1 | 3-cyanophenyl | 320.39 | 321.1 |
| 3A-18 | 1 | 4-phenoxyphenyl | 387.48 | 388.2 |
| 3A-19 | 1 | 3-phenoxyphenyl | 387.48 | 388.2 |
| 3A-20 | 1 | 2-methoxyphenyl | 325.41 | 326.2 |
| 3A-21 | 1 | 3-methoxyphenyl | 325.41 | 326.2 |
| 3A-22 | 1 | 4-(n-propyloxy)phenyl | 353.46 | 354.2 |
| 3A-23 | 1 | 2-(trifluoromethoxy)phenyl | 379.38 | 380.2 |
| 3A-24 | 1 | 3-(trifluoromethoxy)phenyl | 379.38 | 380.2 |
| 3A-25 | 1 | 2-benzamido | 338.41 | 339.2 |
| 3A-26 | 1 | 3-benzamido | 338.41 | 339.2 |
| 3A-27 | 1 | 4-benzamido | 338.41 | 339.2 |
| 3A-28 | 1 | [1,3,4]oxadiazol-2-yl | 363.42 | 364.1 |
| 3A-29 | 1 | naphthalen-1-yl | 345.44 | 346.1 |
| 3A-30 | 1 | 7-methyl-naphthalen-1-yl | 359.47 | 360.2 |
| 3A-31 | 1 | 2,6-difluorophenyl | 331.36 | 332.1 |
| 3A-32 | 1 | 2,3-difluorophenyl | 331.36 | 332.1 |
| 3A-33 | 1 | 2,5-difluorophenyl | 331.36 | 332.1 |
| 3A-34 | 1 | 3,5-difluorophenyl | 331.36 | 332.1 |
| 3A-35 | 1 | 2,6-dichlorophenyl | 364.27 | 364.1 |
| 3A-36 | 1 | 2,3-dichlorophenyl | 364.27 | 364.1 |
| 3A-37 | 1 | 2,4-dichlorophenyl | 364.27 | 364.1 |
| 3A-38 | 1 | 2,5-dichlorophenyl | 364.27 | 364.1 |
| 3A-39 | 1 | 3,4-dichlorophenyl | 364.27 | 364.1 |
| 3A-40 | 1 | 3,5-dichlorophenyl | 364.27 | 364.1 |
| 3A-41 | 1 | 4-bromo-2-fluorophenyl | 392.27 | 394.1 |
| 3A-42 | 1 | 4-chloro-2-fluorophenyl | 347.82 | 348.0 |
| 3A-43 | 1 | 2-chloro-5-fluorophenyl | 347.82 | 348.0 |
| 3A-44 | 1 | 2,6-dimethylphenyl | 323.44 | 324.1 |
| 3A-45 | 1 | 2,3-dimethylphenyl | 323.44 | 324.1 |
| 3A-46 | 1 | 3,4-dimethylphenyl | 323.44 | 324.1 |
| 3A-47 | 1 | 3,5-dimethylphenyl | 323.44 | 324.1 |
| 3A-48 | 1 | 2,5-dimethylphenyl | 323.44 | 324.1 |
| 3A-49 | 1 | 5-chloro-2-methylphenyl | 343.86 | 344.1 |
| 3A-50 | 1 | 2-chloro-5-methylphenyl | 343.86 | 344.1 |
| 3A-51 | 1 | 2-fluoro-5-methylphenyl | 327.40 | 328.1 |
| 3A-52 | 1 | 5-fluoro-2-methylphenyl | 327.40 | 328.1 |
| 3A-53 | 1 | 2-fluoro-3-(trifluoromethyl)-phenyl | 381.37 | 382.1 |
| 3A-54 | 1 | 3-chloro-2-cyanophenyl | 354.84 | 355.0 |
| 3A-55 | 1 | 2-chloro-3-cyanophenyl | 354.84 | 355.0 |
| 3A-56 | 1 | 4-chloro-2-cyanophenyl | 354.84 | 355.0 |
| 3A-57 | 1 | 4-bromo-2-cyanophenyl | 399.29 | 399.3 |
| 3A-58 | 1 | 4-fluoro-3-cyanophenyl | 338.38 | 339.3 |
| 3A-59 | 1 | 3-chloro-5-cyanophenyl | 354.84 | 355.0 |
| 3A-60 | 1 | 3-cyano-5-methylphenyl | 334.42 | 335.3 |
| 3A-61 | 1 | 2-fluoro-6-methylphenyl | 343.40 | 344.1 |
| 3A-62 | 1 | 2-(4-chlorobenzamido) | 372.85 | 373.1 |
| 3A-63 | 1 | 2,3,6-trifluorophenyl | 349.35 | 350.1 |
| 3A-64 | 1 | 2,3,6-trimethylphenyl | 337.46 | 338.2 |
| 3A-65 | 1 | pyridin-2-yl | 296.37 | 297.1 |
| 3A-66 | 1 | pyridin-3-yl | 296.37 | 297.1 |
| 3A-67 | 1 | 6-methylpyridin-2-yl | 310.40 | 311.2 |
| 3A-68 | 1 | 6-cyanopyridin-2-yl | 321.38 | 322.0 |
| 3A-69 | 1 | 5-chloropyridin-2-yl | 330.82 | 331.1 |
| 3A-70 | 1 | 5-chloropyridin-3-yl | 330.82 | 331.1 |
| 3A-71 | 1 | 3-chloro-5,6,7,8-tetrahydro-isoquinolin-1-yl | 384.91 | 385.0 |
| 3A-72 | 1 | 5,6,7,8-tetrahydro-naphthalen-1-yl | 349.47 | 350.2 |
| 3A-73 | 1 | indan-4-yl | 335.45 | 336.2 |
| 3A-74 | 1 | indan-5-yl | 335.45 | 336.2 |
| 3A-75 | 1 | 5-methoxy-indan-4-yl | 365.47 | 365.9 |
| 3A-76 | 1 | 6-fluoro-indan-4-yl | 353.44 | 354.2 |
| 3A-77 | 1 | 2,2-dimethyl-2,3-dihydrobenzofuran-7-yl | 365.47 | 366.1 |
| 3A-78 | 1 | 1,3-dihydro-indol-2-on-7-yl | 350.42 | 351.1 |
| 3A-79 | 1 | N-ethyl-(1,3-dihydro-indol-2-on-4-yl) | 378.47 | 380.2 |
| 3A-80 | 1 | 1,2-benzoisoxazol-3(2H)-on-7-yl | 352.39 | 353.1 |
| 3A-81 | 1 | 1,3-dihydro-2H-benzimidazol-2-on-4-yl | 351.41 | 352.1 |
| 3A-82 | 1 | 1,3-benzoxathiol-2-on-4-yl | 369.44 | 369.9 |
| 3A-83 | 1 | isoquinolin-4-yl | 346.43 | 347.0 |
| 3A-84 | 1 | quinolin-8-yl | 346.43 | 347.2 |
| 3A-85 | 1 | isoquinolin-5-yl | 346.43 | 347.0 |
| 3A-86 | 1 | quinolin-5-yl | 346.43 | 347.0 |

TABLE 3A-continued

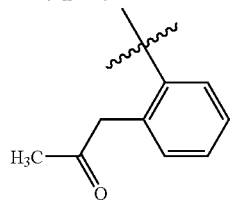

| Example No. | m | R¹ | MS Calc | MS Found (M + 1) |
|---|---|---|---|---|
| 3A-87 | 1 | 2-bromo-quinolin-8-yl | 425.33 | 424.9 |
| 3A-88 | 1 | 2-methyl-quinolin-8-yl | 360.46 | 361.0 |
| 3A-89 | 1 | 5,7-dichloro-2-methyl-quinolin-8-yl | 429.35 | 429.1 |
| 3A-90 | 1 | 7-(n-propyl)-quinolin-8-yl | 388.51 | 389.2 |
| 3A-91 | 1 | 2-cyano-quinolin-8-yl | 371.44 | 372.2 |
| 3A-92 | 1 | 2-methoxy-quinolin-8-yl | 376.46 | 377.0 |
| 3A-93 | 1 | 2-(n-butylamino)-quinolin-8-yl | 417.55 | 418.2 |
| 3A-94 | 1 | 2-(phenylamino)-quinolin-8-yl | 437.54 | 437.8 |
| 3A-95 | 1 | 2-piperidin-1-ylquinolin-8-yl | 429.57 | 430.2 |
| 3A-96 | 1 | 2-morpholin-4-ylquinolin-8-yl | 431.54 | 432.2 |
| 3A-97 | 1 | 2-(3,5-dimethyl-pyrazol-1-yl)quinolin-8-yl | 440.55 | 441.2 |
| 3A-98 | 1 | 4-chloro-quinolin-8-yl | 380.88 | 381.1 |
| 3A-99 | 1 | 1,3-benzoxazol-4-yl | 336.39 | 337.0 |
| 3A-100 | 1 | 2-methyl-1,3-benzoxazol-4-yl | 350.42 | 351.1 |
| 3A-101 | 1 | 2-methyl-1,3-benzothiazol-7-yl | 366.49 | 367.3 |
| 3A-102 | 2 | phenyl | 309.41 | 310.2 |
| 3A-103 | 2 | 3-chlorophenyl | 343.86 | 344.1 |
| 3A-104 | 2 | 3-fluorophenyl | 327.40 | 328.0 |
| 3A-105 | 2 | 2-bromophenyl | 388.31 | 388.1 |
| 3A-106 | 2 | 3-bromophenyl | 388.31 | 388.1 |
| 3A-107 | 2 | 4-methylphenyl | 323.44 | 324.1 |
| 3A-108 | 2 | 2-(n-propyl)phenyl | 351.49 | 352.2 |
| 3A-109 | 2 | 3-(n-propyl)phenyl | 351.49 | 352.2 |
| 3A-110 | 2 | 2-(iso-propyl)phenyl | 351.49 | 352.2 |
| 3A-111 | 2 | 2-(tert-butyl)phenyl | 365.52 | 366.2 |
| 3A-112 | 2 | 3-(tert-butyl)phenyl | 365.52 | 366.2 |
| 3A-113 | 2 | 2-(sec-butyl)phenyl | 365.52 | 366.2 |
| 3A-114 | 2 | 2-(1-methylbutyl)phenyl | 379.54 | 380.3 |
| 3A-115 | 2 | 2-cyclopentylphenyl | 377.53 | 378.2 |
| 3A-116 | 2 | 2-cyclohexylphenyl | 391.56 | 392.3 |
| 3A-117 | 2 | 3-ethylphenyl | 337.46 | 338.2 |
| 3A-118 | 2 | 2-[(N,N-dimethylamino)-methyl]phenyl | 366.51 | 367.2 |
| 3A-119 | 2 | 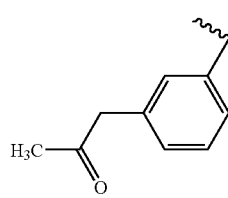 | 381.47 | 382.2 |
| 3A-120 | 2 | 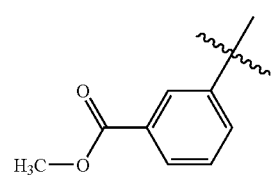 | 381.47 | 382.2 |
| 3A-121 | 2 | 2-benzylphenyl | 399.53 | 400.2 |
| 3A-122 | 2 | 2-cyanophenyl | 334.42 | 335.1 |
| 3A-123 | 2 | 3-cyanophenyl | 334.42 | 335.1 |
| 3A-124 | 2 | 2-methoxyphenyl | 339.44 | 340.2 |
| 3A-125 | 2 | 2-ethoxyphenyl | 353.46 | 354.2 |
| 3A-126 | 2 | 2-(iso-propyloxy)phenyl | 367.49 | 368.2 |
| 3A-127 | 2 | 3-methoxyphenyl | 339.44 | 340.2 |
| 3A-128 | 2 | 3-ethoxyphenyl | 353.46 | 354.2 |
| 3A-129 | 2 | 3-(n-butyloxy)phenyl | 381.52 | 382.2 |
| 3A-130 | 2 | 4-(n-propyloxy)phenyl | 367.49 | 368.2 |
| 3A-131 | 2 | 3-(trifluoromethoxy)phenyl | 393.41 | 394.2 |
| 3A-132 | 2 | 3-phenoxyphenyl | 401.51 | 402.2 |
| 3A-133 | 2 | 4-phenoxyphenyl | 401.51 | 402.2 |
| 3A-134 | 2 | 3-(N,N-dimethylamino)phenyl | 352.48 | 353.2 |
| 3A-135 | 2 | 3-acetylphenyl | 351.45 | 352.2 |
| 3A-136 | 2 | 2-acetylphenyl | 351.45 | 352.2 |
| 3A-137 | 2 | 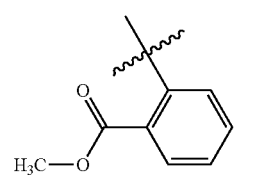 | 367.48 | 368.2 |
| 3A-138 | 2 | 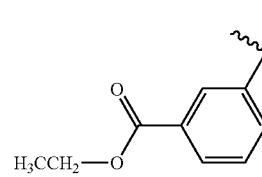 | 367.48 | 368.2 |
| 3A-139 | 2 | 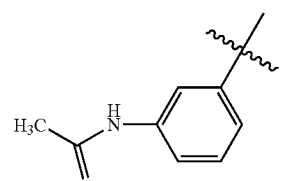 | 381.47 | 382.2 |
| 3A-140 | 2 | 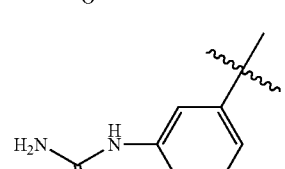 | 366.46 | 367.2 |
| 3A-141 | 2 |  | 367.45 | 368.2 |
| 3A-142 | 2 | 3-benzamido | 352.44 | 353.2 |
| 3A-143 | 2 | 2-benzamido | 352.44 | 353.2 |
| 3A-144 | 2 | N-(n-propyl)-2-benzamido | 394.52 | 395.2 |

TABLE 3A-continued

| Example No. | m | R¹ | MS Calc | MS Found (M + 1) |
|---|---|---|---|---|
| 3A-145 | 2 | [2-(pyrrolidin-1-ylcarbonyl)phenyl structure] | 406.53 | 407.2 |
| 3A-146 | 2 | 3-biphenyl | 385.51 | 386.2 |
| 3A-147 | 2 | 2-biphenyl | 385.51 | 386.2 |
| 3A-148 | 2 | 2-(1H-pyrrol-1-yl)phenyl | 374.48 | 375.2 |
| 3A-149 | 2 | 2-isoxazol-5-ylphenyl | 376.46 | 377.2 |
| 3A-150 | 2 | 2-(1,2,3-thiadiazol-4-yl)phenyl | 393.51 | 394.2 |
| 3A-151 | 2 | 2,6-dichlorophenyl | 378.30 | 378.2 |
| 3A-152 | 2 | 3,5-dichlorophenyl | 378.30 | 378.2 |
| 3A-153 | 2 | 2,6-difluorophenyl | 345.39 | 346.2 |
| 3A-154 | 2 | 2,3-difluorophenyl | 345.39 | 346.1 |
| 3A-155 | 2 | 2,4-difluorophenyl | 345.39 | 346.1 |
| 3A-156 | 2 | 2,5-difluorophenyl | 345.39 | 346.1 |
| 3A-157 | 2 | 3,5-difluorophenyl | 345.39 | 346.2 |
| 3A-158 | 2 | 2-chloro-6-fluorophenyl | 361.85 | 362.1 |
| 3A-159 | 2 | 3-chloro-2-fluorophenyl | 361.85 | 362.1 |
| 3A-160 | 2 | 4-chloro-2-fluorophenyl | 361.85 | 362.1 |
| 3A-161 | 2 | 4-bromo-2-fluorophenyl | 406.30 | 408.0 |
| 3A-162 | 2 | 2-bromo-5-fluorophenyl | 406.30 | 406.1 |
| 3A-163 | 2 | 2,6-dimethylphenyl | 337.46 | 338.2 |
| 3A-164 | 2 | 2-(n-propyl)-6-methylphenyl | 365.52 | 366.2 |
| 3A-165 | 2 | 2,3-dimethylphenyl | 337.46 | 338.2 |
| 3A-166 | 2 | 3,4-dimethylphenyl | 337.46 | 338.2 |
| 3A-167 | 2 | 2,5-dimethylphenyl | 337.46 | 338.2 |
| 3A-168 | 2 | 3,5-dimethylphenyl | 337.46 | 338.2 |
| 3A-169 | 2 | 5-(iso-propyl)-2-methylphenyl | 365.52 | 366.2 |
| 3A-170 | 2 | 2-(iso-propyl)-5-methylphenyl | 365.52 | 366.2 |
| 3A-171 | 2 | 2-(tert-butyl)-5-methylphenyl | 379.55 | 380.3 |
| 3A-172 | 2 | 2-cyclohexyl-5-methylphenyl | 405.58 | 406.3 |
| 3A-173 | 2 | 2,5-di-iso-propylphenyl | 393.57 | 394.3 |
| 3A-174 | 2 | 3-ethyl-5-methylphenyl | 351.49 | 352.2 |
| 3A-175 | 2 | 2,6-dimethoxyphenyl | 369.46 | 370.2 |
| 3A-176 | 2 | 2,3-dimethoxyphenyl | 369.46 | 370.2 |
| 3A-177 | 2 | 3,5-dimethoxyphenyl | 369.46 | 370.2 |
| 3A-178 | 2 | 2-chloro-6-methylphenyl | 357.88 | 358.2 |
| 3A-179 | 2 | 2-chloro-5-methylphenyl | 357.88 | 358.2 |
| 3A-180 | 2 | 5-chloro-2-methylphenyl | 357.88 | 358.2 |
| 3A-181 | 2 | 5-fluoro-2-methylphenyl | 341.43 | 342.2 |
| 3A-182 | 2 | 2-fluoro-3-(trifluoromethyl)-phenyl | 395.40 | 396.1 |
| 3A-183 | 2 | 2-chloro-3-(trifluoromethyl)-phenyl | 411.85 | 412.1 |
| 3A-184 | 2 | 2-fluoro-5-(trifluoromethyl)-phenyl | 395.40 | 396.2 |
| 3A-185 | 2 | 2-chloro-5-(trifluoromethyl)-phenyl | 411.85 | 412.1 |
| 3A-186 | 2 | 2-chloro-5-methoxyphenyl | 373.88 | 374.2 |
| 3A-187 | 2 | 2-fluoro-6-methoxyphenyl | 357.43 | 358.1 |
| 3A-188 | 2 | 5-methyl-2-methoxyphenyl | 353.46 | 354.2 |
| 3A-189 | 2 | 3-methoxy-5-methylphenyl | 353.46 | 354.2 |
| 3A-190 | 2 | [3-methoxy-2-(cyanomethyl)phenyl structure] | 378.47 | 379.2 |
| 3A-191 | 2 | [3-methoxy-2-(methoxycarbonyl)phenyl structure] | 397.42 | 398.2 |
| 3A-192 | 2 | [4-methoxy-3-(methoxycarbonyl)phenyl structure] | 397.42 | 398.2 |
| 3A-193 | 2 | [2-(ethoxycarbonyl)-6-methylphenyl structure] | 395.50 | 396.2 |
| 3A-194 | 2 | 3-hydroxy-5-acetylphenyl | 367.45 | 368.2 |
| 3A-195 | 2 | 2-acetyl-3-methoxyphenyl | 381.47 | 382.2 |
| 3A-196 | 2 | 2-acetyl-5-methoxyphenyl | 381.47 | 382.2 |
| 3A-197 | 2 | 2,2-dimethyl-2,3-dihydro-1-benzofuran-7-yl | 379.50 | 380.2 |
| 3A-198 | 2 | 2,3,6-trichlorophenyl | 412.75 | 414.0 |
| 3A-199 | 2 | 2,3,6-trifluorophenyl | 363.38 | 364.1 |
| 3A-200 | 2 | 2-bromo-pyridin-3-yl | 389.29 | 389.1 |
| 3A-201 | 2 | 2-methyl-pyridin-3-yl | 324.43 | 325.1 |
| 3A-202 | 2 | [5-(methoxycarbonyl)pyridin-3-yl structure] | 368.43 | 369.2 |

TABLE 3A-continued

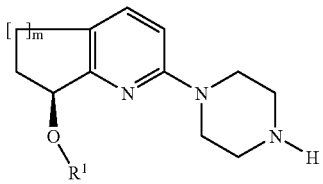

| Example No. | m | R$^1$ | MS Calc | MS Found (M + 1) |
|---|---|---|---|---|
| 3A-203 | 2 | pyridin-2-yl | 310.40 | 311.1 |
| 3A-204 | 2 | 6-methyl-pyridin-2-yl | 324.43 | 325.1 |
| 3A-205 | 2 | 2-acetyl-benzofuran-7-yl | 391.47 | 392.2 |

TABLE 3B

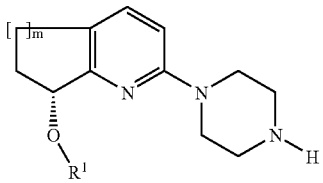

| Example No. | m | R$^1$ | MS Calc | MS Found (M + 1) |
|---|---|---|---|---|
| 3B-1 | 1 | 2-chlorophenyl | 329.83 | 330.1 |
| 3B-2 | 1 | 3-chlorophenyl | 329.83 | 330.1 |
| 3B-3 | 1 | 4-chlorophenyl | 329.83 | 330.1 |
| 3B-4 | 1 | 2-fluorophenyl | 313.37 | 314.1 |
| 3B-5 | 1 | 3-fluorophenyl | 313.37 | 314.1 |
| 3B-6 | 1 | 4-fluorophenyl | 313.37 | 314.1 |
| 3B-7 | 1 | 2-methylphenyl | 309.41 | 310.1 |
| 3B-8 | 1 | 2-ethylphenyl | 323.44 | 324.1 |
| 3B-9 | 1 | 3-methylphenyl | 309.41 | 310.1 |
| 3B-10 | 1 | 4-methylphenyl | 309.41 | 310.1 |
| 3B-11 | 1 | 2-trifluoromethyl-phenyl | 363.38 | 364.1 |
| 3B-12 | 1 | 3-trifluoromethyl-phenyl | 363.38 | 364.1 |
| 3B-13 | 1 | 2-cyanophenyl | 320.39 | 321.1 |
| 3B-14 | 1 | 3-cyanophenyl | 320.39 | 321.1 |
| 3B-15 | 1 | naphthalen-1-yl | 345.44 | 346.1 |
| 3B-16 | 1 | 2,6-difluorophenyl | 331.36 | 332.1 |
| 3B-17 | 1 | 2,3-difluorophenyl | 331.36 | 332.1 |
| 3B-18 | 1 | 2,5-difluorophenyl | 331.36 | 332.1 |
| 3B-19 | 1 | 3,5-difluorophenyl | 331.36 | 332.1 |
| 3B-20 | 1 | 2,6-dichlorophenyl | 364.27 | 364.1 |
| 3B-21 | 1 | 2,3-dichlorophenyl | 364.27 | 364.1 |
| 3B-22 | 1 | 2,4-dichlorophenyl | 364.27 | 364.1 |
| 3B-23 | 1 | 2,5-dichlorophenyl | 364.27 | 364.1 |
| 3B-24 | 1 | 3,4-dichlorophenyl | 364.27 | 364.1 |
| 3B-25 | 1 | 3,5-dichlorophenyl | 364.27 | 364.1 |
| 3B-26 | 1 | 2,6-dimethylphenyl | 323.44 | 324.1 |
| 3B-27 | 1 | 2,3-dimethylphenyl | 323.44 | 324.1 |
| 3B-28 | 1 | 2,5-dimethylphenyl | 323.44 | 324.1 |
| 3B-29 | 1 | 3,4-dicyanophenyl | 345.40 | 346.2 |
| 3B-30 | 1 | 2-chloro-5-methylphenyl | 343.86 | 344.0 |
| 3B-31 | 1 | 2-fluoro-5-methylphenyl | 327.40 | 328.1 |
| 3B-32 | 1 | 2-fluoro-3-trifluoromethyl-phenyl | 381.37 | 382.1 |
| 3B-33 | 1 | 4-chloro-2-cyanophenyl | 354.84 | 355.1 |
| 3B-34 | 1 | 4-bromo-2-cyanophenyl | 399.29 | 401.1 |

TABLE 3B-continued

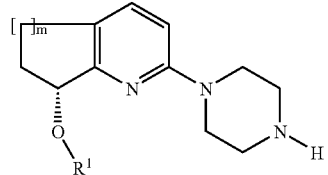

| Example No. | m | R$^1$ | MS Calc | MS Found (M + 1) |
|---|---|---|---|---|
| 3B-35 | 1 | 2-cyano-4-methoxyphenyl | 350.42 | 351.2 |
| 3B-36 | 1 | 3-cyano-4-fluorophenyl | 338.38 | 339.2 |
| 3B-37 | 1 | 2-fluoro-6-methoxyphenyl | 343.40 | 344.1 |
| 3B-38 | 1 | 2-(5-methoxybenzamido) | 368.43 | 369.2 |
| 3B-39 | 1 | pyridin-2-yl | 296.37 | 297.1 |
| 3B-40 | 1 | pyridin-3-yl | 296.37 | 297.1 |
| 3B-41 | 2 | phenyl | 309.41 | 310.2 |
| 3B-42 | 2 | 3-chlorophenyl | 343.86 | 344.1 |
| 3B-43 | 2 | 2-bromophenyl | 388.31 | 388.1 |
| 3B-44 | 2 | 3-bromophenyl | 388.31 | 388.1 |
| 3B-45 | 2 | 4-methylphenyl | 323.44 | 324.1 |
| 3B-46 | 2 | 2-(n-propyl)phenyl | 351.49 | 352.2 |
| 3B-47 | 2 | 2-(iso-propyl)phenyl | 351.49 | 352.2 |
| 3B-48 | 2 | 2-(tert-butyl)phenyl | 365.52 | 366.2 |
| 3B-49 | 2 | 2-(1-methyl-n-butyl)phenyl | 379.54 | 380.2 |
| 3B-50 | 2 | 2-cyclopentylphenyl | 377.53 | 378.2 |
| 3B-51 | 2 | 2-cyclohexylphenyl | 391.56 | 392.3 |
| 3B-52 | 2 | 3-ethylphenyl | 337.46 | 338.2 |
| 3B-53 | 2 | 3-(n-propyl)phenyl | 351.49 | 352.2 |
| 3B-54 | 2 | 3-(tert-butyl)phenyl | 365.52 | 366.2 |
| 3B-55 | 2 | 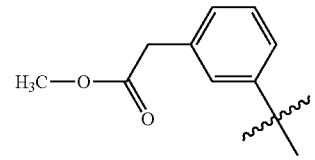 | 381.47 | 382.2 |
| 3B-56 | 2 | 2-benzyl | 399.54 | 400.2 |
| 3B-57 | 2 | 2-cyanophenyl | 334.42 | 335.1 |
| 3B-58 | 2 | 3-cyanophenyl | 334.42 | 335.1 |
| 3B-59 | 2 | 2-methoxyphenyl | 339.44 | 340.2 |
| 3B-60 | 2 | 2-ethoxyphenyl | 353.46 | 354.2 |
| 3B-61 | 2 | 2-(iso-propyloxy)phenyl | 367.49 | 368.2 |
| 3B-62 | 2 | 3-methoxyphenyl | 339.44 | 340.2 |
| 3B-63 | 2 | 3-ethoxyphenyl | 353.46 | 354.2 |
| 3B-64 | 2 | 3-(n-butyloxy)phenyl | 381.52 | 382.2 |
| 3B-65 | 2 | 4-(n-propyloxy)phenyl | 367.49 | 368.2 |
| 3B-66 | 2 | 3-trifluoromethoxy-phenyl | 393.41 | 394.2 |
| 3B-67 | 2 | 4-phenoxy | 401.51 | 402.2 |
| 3B-68 | 2 | 3-phenoxy | 401.51 | 402.2 |
| 3B-69 | 2 | 3-(N,N-dimethyl-amino)phenyl | 352.48 | 353.2 |
| 3B-70 | 2 | 3-acetylphenyl | 351.45 | 352.2 |
| 3B-71 | 2 | 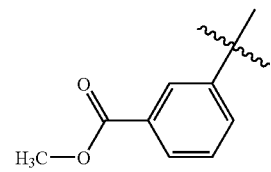 | 367.45 | 368.2 |

TABLE 3B-continued

| Example No. | m | R¹ | MS Calc | MS Found (M + 1) |
|---|---|---|---|---|
| 3B-72 | 2 | 2-(methoxycarbonyl)phenyl (methyl 2-benzoate) | 367.45 | 368.2 |
| 3B-73 | 2 | 3-(ethoxycarbonyl)phenyl | 381.47 | 382.2 |
| 3B-74 | 2 | 3-acetamidophenyl | 366.46 | 367.2 |
| 3B-75 | 2 | 3-ureidophenyl | 367.45 | 368.2 |
| 3B-76 | 2 | 3-benzamido | 352.44 | 353.2 |
| 3B-77 | 2 | 2-benzamido | 352.44 | 353.2 |
| 3B-78 | 2 | N-(n-propyl)-2-benzamido | 394.52 | 395.2 |
| 3B-79 | 2 | 2-(pyrrolidin-1-ylcarbonyl)phenyl | 406.53 | 407.2 |
| 3B-80 | 2 | 2-biphenyl | 385.51 | 386.2 |
| 3B-81 | 2 | 3-biphenyl | 385.51 | 386.2 |
| 3B-82 | 2 | 2-isoxazol-5-ylphenyl | 376.46 | 377.2 |
| 3B-83 | 2 | 2-(1,2,3-thiadiazol-4-yl)phenyl | 393.51 | 394.2 |
| 3B-84 | 2 | 2-(1H-pyrrol-1-yl)phenyl | 374.49 | 375.2 |
| 3B-85 | 2 | 2,6-dichlorophenyl | 378.30 | 378.1 |
| 3B-86 | 2 | 3,5-dichlorophenyl | 378.30 | 378.1 |
| 3B-87 | 2 | 2,6-difluorophenyl | 345.39 | 346.2 |
| 3B-88 | 2 | 2,3-difluorophenyl | 345.39 | 346.2 |
| 3B-89 | 2 | 2,4-difluorophenyl | 345.39 | 346.2 |
| 3B-90 | 2 | 2,5-difluorophenyl | 345.39 | 346.2 |
| 3B-91 | 2 | 3,5-difluorophenyl | 345.39 | 346.2 |
| 3B-92 | 2 | 2-chloro-6-fluorophenyl | 361.85 | 362.1 |
| 3B-93 | 2 | 3-chloro-2-fluorophenyl | 361.85 | 362.1 |
| 3B-94 | 2 | 4-chloro-2-fluorophenyl | 361.85 | 362.1 |
| 3B-95 | 2 | 4-bromo-2-fluorophenyl | 406.30 | 408.0 |
| 3B-96 | 2 | 2-bromo-5-fluorophenyl | 406.30 | 408.0 |
| 3B-97 | 2 | 2,6-dimethylphenyl | 337.40 | 338.2 |
| 3B-98 | 2 | 2-(n-propyl)-6-methylphenyl | 365.52 | 366.2 |
| 3B-99 | 2 | 2,3-dimethylphenyl | 337.46 | 338.2 |
| 3B-100 | 2 | 3,4-dimethylphenyl | 337.46 | 338.2 |
| 3B-101 | 2 | 2,5-dimethylphenyl | 337.46 | 338.2 |
| 3B-102 | 2 | 5-(iso-propyl)-2-methylphenyl | 365.52 | 366.2 |
| 3B-103 | 2 | 2-(iso-propyl)-5-methylphenyl | 365.52 | 366.2 |
| 3B-104 | 2 | 2-(tert-butyl)-5-methylphenyl | 379.54 | 380.3 |
| 3B-105 | 2 | 2-cyclohexyl-5-methylphenyl | 405.58 | 406.3 |
| 3B-106 | 2 | 2,5-di-iso-propyl)phenyl | 393.57 | 394.3 |
| 3B-107 | 2 | 3,5-dimethylphenyl | 337.46 | 338.2 |
| 3B-108 | 2 | 3-ethyl-5-methylphenyl | 351.49 | 352.2 |
| 3B-109 | 2 | 2,6-dimethoxyphenyl | 369.46 | 370.2 |
| 3B-110 | 2 | 2,3-dimethoxyphenyl | 369.46 | 370.2 |
| 3B-111 | 2 | 3,5-dimethoxyphenyl | 369.46 | 370.2 |
| 3B-112 | 2 | 2-chloro-6-methylphenyl | 357.88 | 358.2 |
| 3B-113 | 2 | 2-chloro-5-methylphenyl | 357.88 | 358.2 |
| 3B-114 | 2 | 2-fluoro-5-methylphenyl | 341.43 | 342.1 |
| 3B-115 | 2 | 5-chloro-2-methylphenyl | 357.88 | 358.1 |
| 3B-116 | 2 | 2-fluoro-3-trifluoromethylphenyl | 395.40 | 396.1 |
| 3B-117 | 2 | 2-chloro-3-trifluoromethylphenyl | 411.85 | 412.1 |
| 3B-118 | 2 | 2-fluoro-5-trifluoromethylphenyl | 395.40 | 396.2 |
| 3B-119 | 2 | 2-chloro-5-trifluoromethylphenyl | 411.85 | 412.1 |
| 3B-120 | 2 | 2-chloro-5-methoxyphenyl | 373.88 | 374.1 |
| 3B-121 | 2 | 2-fluoro-6-methoxyphenyl | 357.43 | 358.2 |
| 3B-122 | 2 | 2-methoxy-5-methylphenyl | 353.46 | 354.2 |
| 3B-123 | 2 | 3-methoxy-5-methylphenyl | 357.88 | 358.2 |

TABLE 3B-continued

[Structure: bicyclic pyridine with piperazine and OR¹ group, with [ ]m notation]

| Example No. | m | R¹ | MS Calc | MS Found (M + 1) |
|---|---|---|---|---|
| 3B-124 | 2 | 2-methoxy-6-(cyanomethyl)phenyl (structure shown) | 351.49 | 352.2 |
| 3B-125 | 2 | 2-methoxy-6-(methoxycarbonyl)phenyl (structure shown) | 397.47 | 398.2 |
| 3B-126 | 2 | 3-methoxy-4-(methoxycarbonyl)phenyl (structure shown) | 397.47 | 398.2 |
| 3B-127 | 2 | 2-(ethoxycarbonyl)-3-methylphenyl (structure shown) | 395.50 | 396.2 |
| 3B-128 | 2 | 2-acetamido-4-chlorophenyl (structure shown) | 380.49 | 381.2 |
| 3B-129 | 2 | 3-hydroxy-5-acetylphenyl | 367.45 | 368.2 |
| 3B-130 | 2 | 2-acetyl-3-methoxyphenyl | 381.47 | 382.2 |
| 3B-131 | 2 | 2-acetyl-5-methoxyphenyl | 381.47 | 382.2 |
| 3B-132 | 2 | 2,2-dimethyl-2,3-dihydro-1-benzofuran-7-yl | 379.50 | 380.2 |
| 3B-133 | 2 | 2,3,6-trichlorophenyl | 412.75 | 414.0 |
| 3B-134 | 2 | 2,3,6-trifluorophenyl | 363.38 | 364.1 |
| 3B-135 | 2 | 5-chloro-pyridin-3-yl | 344.84 | 345.1 |
| 3B-136 | 2 | 2-bromo-pyridin-3-yl | 389.30 | 389.1 |
| 3B-137 | 2 | 2-methyl-pyridin-3-yl | 324.43 | 325.1 |
| 3B-138 | 2 | 2-methyl-pyridin-3-yl | 324.43 | 325.2 |
| 3B-139 | 2 | 5-(methoxycarbonyl)pyridin-3-yl (structure shown) | 368.44 | 369.2 |
| 3B-140 | 2 | pyridin-2-yl | 310.40 | 311.3 |
| 3B-141 | 2 | 2-acetyl-benzofuran-7-yl | 391.47 | 392.2 |

TABLE 3C

[Structure: bicyclic pyridine with piperazine and OR¹ group, with [ ]m notation]

| Example No. | m | R¹ | MS Calc | MS Found (M + 1) |
|---|---|---|---|---|
| 3C-1 | 1 | 2-chlorophenyl | 329.83 | 330.1 |
| 3C-2 | 1 | 3-chlorophenyl | 329.83 | 330.1 |
| 3C-3 | 1 | 2-methylphenyl | 309.41 | 310.2 |
| 3C-4 | 1 | 3-methylphenyl | 309.41 | 310.2 |
| 3C-5 | 1 | 6-chloro-pyrazin-2-yl | 331.81 | 332.3 |
| 3C-6 | 2 | 2-chlorophenyl | 343.86 | 344.1 |
| 3C-7 | 2 | 3-chlorophenyl | 343.86 | 344.1 |
| 3C-8 | 2 | 4-chlorophenyl | 343.86 | 344.1 |
| 3C-9 | 2 | 2-fluorophenyl | 327.40 | 328.2 |
| 3C-10 | 2 | 3-fluorophenyl | 327.40 | 328.2 |
| 3C-11 | 2 | 4-fluorophenyl | 327.40 | 328.2 |
| 3C-12 | 2 | 2-methylphenyl | 323.44 | 324.2 |
| 3C-13 | 2 | 2-ethylphenyl | 337.46 | 338.2 |
| 3C-14 | 2 | 3-methylphenyl | 323.44 | 324.2 |
| 3C-15 | 2 | 3-(isopropyl)phenyl | 351.49 | 352.2 |
| 3C-16 | 2 | 2-trifluoromethyl-phenyl | 377.41 | 378.2 |
| 3C-17 | 2 | 3-trifluoromethyl-phenyl | 377.41 | 378.2 |
| 3C-18 | 2 | 2-cyanophenyl | 334.42 | 335.2 |
| 3C-19 | 2 | 3-cyanophenyl | 334.42 | 335.2 |
| 3C-20 | 2 | 2-methoxyphenyl | 339.44 | 340.2 |
| 3C-21 | 2 | 3-benzamido | 352.44 | 353.2 |
| 3C-22 | 2 | 2,6-dichlorophenyl | 378.30 | 378.2 |
| 3C-23 | 2 | 2,4-dichlorophenyl | 378.30 | 378.2 |
| 3C-24 | 2 | 2,3-dichlorophenyl | 378.30 | 378.2 |
| 3C-25 | 2 | 3,4-dichlorophenyl | 378.30 | 378.2 |

TABLE 3C-continued

[structure shown]

| Example No. | m | R¹ | MS Calc | MS Found (M + 1) |
|---|---|---|---|---|
| 3C-26 | 2 | 2,5-dichlorophenyl | 378.30 | 378.2 |
| 3C-27 | 2 | 3,5-dichlorophenyl | 378.30 | 378.2 |
| 3C-28 | 2 | 2,3-difluorophenyl | 345.39 | 346.2 |
| 3C-29 | 2 | 3-ethyl-5-methylphenyl | 351.49 | 352.2 |
| 3C-30 | 2 | 2-chloro-6-methylphenyl | 357.88 | 358.2 |
| 3C-31 | 2 | 2-chloro-5-methylphenyl | 357.88 | 358.2 |
| 3C-32 | 2 | 2-fluoro-6-methoxyphenyl | 357.43 | 358.2 |
| 3C-33 | 2 | indan-4-yl | 349.47 | 350.2 |
| 3C-34 | 2 | 5,6,7,8-tetrahydro-naphthalen-1-yl | 363.50 | 364.2 |
| 3C-35 | 2 | pyridin-3-yl | 310.40 | 311.3 |
| 3C-36 | 2 | pyridin-2-yl | 310.40 | 311.3 |
| 3C-37 | 2 | 6-methoxy-pyridin-2-yl | 340.43 | 341.4 |
| 3C-38 | 2 | 3-chloro-pyrazin-2-yl | 345.83 | 346.3 |
| 3C-39 | 2 | 6-chloro-pyrazin-2-yl | 345.83 | 346.3 |
| 3C-40 | 2 | quinolin-8-yl | 360.46 | 361.2 |
| 3C-41 | 2 | 2-fluorophenyl | 327.40 | 328.0 |

Example 4

Preparation of (7S)-7-(2,3-dichlorophenoxy)-2-[(2R)-2-methylpiperazin-1-yl]-6,7-dihydro-5H-cyclopenta[b]pyridine (4A-1)

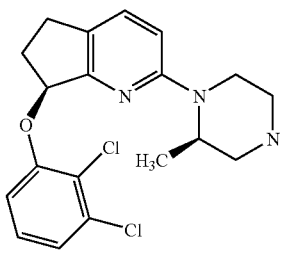

4A-1

Intermediate I-3a (30.0 mg, 0.0954 mmol), (R)-3-methyl-piperazine-1-carboxylic acid tert-butyl ester (24.8 mg, 0.124 mmol), Pd₂(dba)₃ (1.7 mg, 1.907×10⁻³ mmol), Amphos (1.5 mg, 3.814×10⁻³ mmol), and sodium t-butoxide (12.8 mg, 0.134 mmol) were added to a predried reaction vial under a $N_2$ atmosphere. The reagents were dissolved in 1 mL anhydrous toluene and stirred with heating at 90° C. overnight. The reaction mixture was filtered through celite washing with EtOAc, the solvent removed in vacuo, and the residue was then purified by preparative TLC (eluting with 25% EtOAc/Hexane) to afford BOC-protected.

Trifluoroacetic acid (59.3 μL, 0.520 mmol) was added to a solution of the BOC-protected compound from above (24.9 mg, 0.0520 mmol) in 1.0 mL of $CH_2Cl_2$, and the reaction mixture was allowed to stir at room temperature overnight. The solvent was removed in vacuo and the residue was purified by preparative TLC (eluting with 10% MeOH, 1% $NH_4OH/CH_2Cl_2$) to give 10.4 mg, (31.1% 3-step yield) of the title compound (4A-1).

MS calculated=378.30, MS+1 observed=378.2 1H NMR (400M Hz, CDCl₃): d 7.79 (d, 1H), 7.20-7.08 (m, 3H), 6.88 (d, 1H), 5.78 (m, 1H), 4.64 (bs, 1H), 4.04 (d, 1H), 3.62 (t, 1H), 3.53 (d, 1H), 3.38 (m, 2H), 3.17 (m, 2H), 2.90 (m, 1H), 2.56 (m, 1H), 2.36 (m, 1H), 1.32 (d, 3H).

The compounds listed in Tables 4A, 4B and 4C below were prepared using procedures analogous to those described above for the synthesis of Compound 4A-1 using the appropriate starting materials which are available commercially, prepared using preparations well-known to those skilled in the art, or prepared in a manner analogous to routes described above for other intermediates. For those compounds that were prepared from a racemic intermediate, the racemic compound or enantio-enriched compound was separated on column Chiralpak AD (dimension 4.6 mm×25 cm). Mobile phase contained heptane and EtOH with TFA as modifier. The flow rate was set at 1 mL/min.

TABLE 4A

[structure shown]

| Example No. | R¹ | MS Calc | MS Found (M + 1) |
|---|---|---|---|
| 4A-1 | 2,3-dichlorophenyl | 378.30 | 378.2 |
| 4A-2 | 2-chlorophenyl | 343.86 | 344.1 |
| 4A-3 | 3-chlorophenyl | 343.86 | 344.1 |
| 4A-4 | 2-fluorophenyl | 327.40 | 328.2 |
| 4A-5 | 3-fluorophenyl | 327.40 | 328.2 |
| 4A-6 | 2-methylphenyl | 323.44 | 324.2 |
| 4A-7 | 3-methylphenyl | 323.44 | 324.2 |
| 4A-8 | 2-trifluoromethylphenyl | 377.41 | 378.2 |
| 4A-9 | 2-cyanophenyl | 334.42 | 335.2 |
| 4A-10 | 3-cyanophenyl | 334.42 | 335.2 |
| 4A-11 | 3,5-difluorophenyl | 345.39 | 346.2 |
| 4A-12 | 2,5-difluorophenyl | 345.39 | 346.2 |
| 4A-13 | 2,3-difluorophenyl | 345.39 | 346.2 |
| 4A-14 | 2,5-dimethylphenyl | 357.88 | 358.2 |
| 4A-15 | 2-fluoro-5-methylphenyl | 341.43 | 342.2 |
| 4A-16 | 5-fluoro-2-methylphenyl | 341.43 | 342.2 |
| 4A-17 | isoquinolin-8-yl | 360.46 | 361.1 |
| 4A-18 | 2-methyl-quinolin-8-yl | 374.48 | 374.8 |
| 4A-19 | indan-4-yl | 349.47 | 350.0 |
| 4A-20 | 6-fluoro-indan-4-yl | 367.46 | 368.1 |
| 4A-21 | 6-methyl-pyridin-2-yl | 324.43 | 325.2 |

TABLE 4B

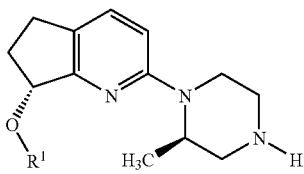

| Example No. | R¹ | MS Calc | MS Found (M + 1) |
|---|---|---|---|
| 4B-1 | 2-chlorophenyl | 343.86 | 344.1 |
| 4B-2 | 3-chlorophenyl | 343.86 | 344.1 |
| 4B-3 | 2-fluorophenyl | 327.40 | 328.1 |
| 4B-4 | 3-fluorophenyl | 327.40 | 328.1 |
| 4B-5 | 2-methylphenyl | 323.44 | 324.1 |
| 4B-6 | 3-methylphenyl | 323.44 | 324.1 |
| 4B-7 | 2-trifluoromethylphenyl | 377.41 | 378.2 |
| 4B-8 | 2-cyanophenyl | 334.42 | 335.1 |
| 4B-9 | 3-cyanophenyl | 334.42 | 335.1 |
| 4B-10 | 2,5-difluorophenyl | 345.39 | 346.1 |
| 46-11 | 3,5-difluorophenyl | 345.39 | 346.1 |
| 46-12 | 2,3-difluorophenyl | 345.39 | 346.1 |
| 46-13 | 5-fluoro-2-methylphenyl | 341.43 | 342.2 |
| 46-14 | 2-fluoro-5-methylphenyl | 341.43 | 342.2 |
| 46-15 | 2-chloro-5-Methyl-phenyl | 357.88 | 358.1 |
| 46-16 | 6-methyl-pyridin-2-yl | 324.43 | 325.2 |

TABLE 4C

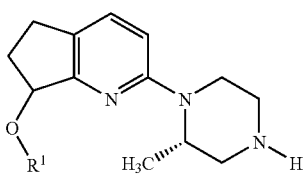

| Example No. | R¹ | MS Calc | MS Found (M + 1) |
|---|---|---|---|
| 4C-1 | (S) 2-chlorophenyl | 343.86 | 344.1 |
| 4C-2 | (R) 2-chlorophenyl | 343.86 | 344.1 |

The following compounds were made similarly to Examples 2 and 3, except a chlorination step was added before the N-Boc depotection in the synthesis. The chlorination can be accomplished with NCS or other reagents which are known in the art.

Example 5

Preparation of 3-chloro-7(S)-(2,5-difluoro-benzyloxy)-2-(2-(R)-methyl-piperazin-1-yl)-6,7-dihydro-5H-[1]-pyridine, (5A-1)

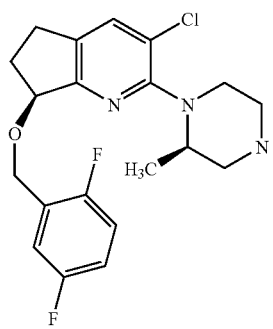

5A-1

The corresponding 4-[7-(S)-(2,5-difluoro-benzyloxy-6,7-dihydro-5H-[1]pyridine-2-yl]-3-(R)-methyl-piperazine-1-carboxylic acid tert-butyl ester (prepared according to the procedure in example 2, 20 mg, 0.044 mmol) was treated with NCS (6.1 mg, 0.046 mmol) in 1 mL acetonitrile. The mixture was refluxed for 2 hr and then cooled to room temperature. The reaction mixture was filtered through celite washing with EtOAc, the solvent removed in vacuo, and the residue was then purified by preparative TLC (eluting with 20% EtOAc/Hexane) to give the 3-chloro-pyridine intermediate. Subsequently, trifluoroacetic acid (10.7 μL, 0.14 mmol) was added to a solution of the 3-chloro-pyridine compound from above (7 mg, 0.014 mmol) in 0.5 mL of $CH_2Cl_2$, and the reaction mixture was allowed to stir at room temperature overnight. The solvent was removed in vacuo and the residue was purified by preparative TLC (eluting with 10% MeOH, 1% $NH_4OH/CH_2Cl_2$) to give 4.3 mg, (25% 2-step yield) of the title compound (5A-1).

MS calculated=393.9, MS+1 observed=394.2 1H NMR (400M Hz, $CDCl_3$): d 7.67 (s, 1H), 7.20-7.28 (m, 1H), 6.88-7.15 (m, 2H), 4.88 (m, 2H), 3.71 (m, 1H), 3.1-2.65 (m, 9H), 2.42 (m, 1H), 2.18 (m, 1H) 1.02 (d, 3H).

The compounds listed in Tables 5A and 5B below were prepared using procedures analogous to those described above for the synthesis of Compound 5A-1 using the appropriate starting materials which are available commercially, prepared using preparations well-known to those skilled in the art, or prepared in a manner analogous to routes described above for other intermediates. For those compounds that were prepared from a racemic intermediate, the racemic compound or enantio-enriched compound was separated on column Chiralpak AD (dimension 4.6 mm×25 cm). Mobile phase contained heptane and EtOH with TFA as modifier. The flow rate was set at 1 mL/min.

TABLE 5A

| Example No. | $R^{0a}$ | $R^1$ | MS Calc | MS Found (M + 1) |
|---|---|---|---|---|
| 5A-1 | H | 2,5-difluorophenyl | 393.9 | 394.2 |
| 5A-2 | H | 2-methyl-5-fluorophenyl | 389.9 | 390.2 |
| 5A-3 | H | 2-methyl-5-cyanophenyl | 396.9 | 397.2 |

TABLE 5B

| Example No. | m | $R^1$ | MS Calc | MS Found (M + 1) |
|---|---|---|---|---|
| 5B-1 | 2 | 2,3-chlorophenyl | 412.7 | 413.2 |
| 5B-2 | 2 | 2-fluoro-phenyl | 361.8 | 362.4 |
| 5B-3 | 2 | 2-methyl-5-fluorophenyl | 375.9 | 376.2 |
| 5B-4 | 2 | 3,5-difluorophenyl | 379.8 | 380.2 |
| 5B-5 | 2 | 3-fluoro-phenyl | 361.8 | 362.4 |
| 5B-6 | 2 | 2-fluoro-3-chlorophenyl | 396.3 | 397.2 |
| 5B-7 | 1 | 2-chlorophenyl | 364.3 | 365.2 |
| 5B-8 | 1 | 3-chlorophenyl | 364.3 | 365.2 |

Assays

The utility of the compounds of the present invention in the practice of the instant invention was evidenced by activity in one or more of the protocols described hereinbelow.

The following acronyms are used hereinbelow.

DMEM—Dulbecco's Modified Eagle Medium

HEPES—N-2-hydroxyethyl-piperazine-N'-2-ethane sulfonate

EDTA—Ethylenediaminetetraacetic acid

EGTA—Ethylene glycol-bis(β-aminoethyl ether)-N,N,N',N'-tetraacetic acid

PEI—Polyethyleneimine

DMSO—Dimethylsulfoxide

NCS-N-Chlorosuccinimide

Fluo 4-AM™—Fluorescent probe available from Molecular Probes, Inc., Eugene, Oreg.

PerkinElmer™ refers to PerkinElmer Life and Analytical Sciences, Inc., Boston, Mass.

Sigma™ refers to Sigma-Aldrich Corp., St. Louis, Mo.

$5HT_{2c}$ Binding Procedure

Affinity of compounds at the serotonin $5HT_{2c}$ binding site is determined by competition binding in Swiss 3T3 mouse cells (available from the American Type Culture Collection (ATCC), Manassas, Va.) transfected with the human $5HT_{2c}$ receptor against $^3$H-5HT. Cells are grown in DMEM high glucose medium, (switched to medium containing 10% dialyzed fetal bovine serum 18 hours prior to harvest), harvested, centrifuged, and resuspended in Homogenization buffer (10 mM HEPES, pH 7.5, 1 mM EDTA, 1 mM EGTA containing the following protease inhibitors: 0.1 mg/ml benzamidine (Sigma™ B 6506), 0.1 mg/ml bacitracin (Sigma™ B 0125), 0.005 mg/ml leupeptin (Sigma™ L 8511), 0.5 mg/ml aprotinin (Sigma™ A 1153). Cells are incubated in a centrifuge tube on ice for 10 minutes, then homogenized using four 10-second bursts of a Polytron™ homogenizer (Brinkman™, Westbury, N.Y.), and then centrifuged at 1000×g for 10 minutes at 4° C. The supernatant was carefully removed and transferred to new centrifuge tubes, then centrifuged for 20 minutes at 25,000×g at 4° C. The supernatant was removed and discarded, while the pellet was resuspended in homogenization buffer, then centrifuged for 20 minutes at 25,000×g at 4° C. The supernatant was discarded while the pellet (containing membranes) was resuspended in homogenization buffer, and the membranes were aliquoted and frozen at −80° C. Binding activity of test compounds to the $5HT_{2c}$ receptor was determined in 96-well plates containing 2 μl of test compound (in 100% DMSO) then 100 μl of $^3$H-5HT (Amersham Biosciences, Piscataway, N.J.; 2 nM final concentration) which was diluted in assay buffer (50 mM Tris pH 7.7, 10 mM $MgCl_2$, 3 mM $CaCl_2$, 1 mM EDTA, 10 μM pargyline, 0.1% ascorbic acid) followed by 100 μl of membranes (approximately 10 μg membrane protein per well) diluted in assay buffer. 1 μM mianserin was used to calculate non-specific binding. Assay plates were incubated for 60 minutes at 37° C., after which the assay was terminated by filtration onto UniFilter™ plates (with GF/C filters—from PerkinElmer™) that had been pre-soaked in 0.3% PEI. The filterplates were washed 2× with cold wash buffer (50 mM Tris, pH 7.4), then dried, scintillation fluid added and radioactivity determined in a Wallac Microbeta™ plate scintillation counter (PerkinElmer™). Concentration-response curves of the % inhibition of specific binding by test compounds versus the test compound concentration, was used to determine the $IC_{50}$ for each compound and the Ki value calculated based on the Cheng-Prusof equation (Ki=IC50/(1+(L/Kd)), where L is the concentration of the radioligand used in the binding assay and the Kd is based on previous saturation studies with the radioligand.

$5HT_{2a}$ Binding Procedure

Affinity of compounds at the serotonin $5HT_{2a}$ binding site is determined by competition binding in NIH 3T3 mouse cells transfected with the rat $5HT_{2a}$ receptor using 125I-DOI. Cells are grown in DMEM high glucose medium (switched to medium containing 10% dialyzed fetal bovine serum 18 hours prior to harvest), harvested, centrifuged, and resuspended in Homogenization buffer (10 mM HEPES, pH 7.5, 1 mM EDTA, 1 mM EGTA containing the following protease inhibitors: 0.1 mg/ml benzamidine (Sigma™ B 6506), 0.1 mg/ml bacitracin (Sigma™ B 0125), 0.005 mg/ml leupeptin (Sigma™ L 8511), 0.5 mg/ml aprotinin (Sigma™ A1153). Cells are incubated in a centrifuge tube on ice for 10 minutes, then homogenized using four 10-second bursts of a Polytron™ homogenizer (Brinkman™), and then centrifuged at 1000×g for 10 minutes at 4° C. The supernatant was carefully removed and transferred to new centrifuge tubes, then centrifuged for 20 minutes at 25,000×g at 4° C. The supernatant was removed and discarded, while the pellet was resuspended in homogenization buffer, then centrifuged for 20 minutes at 25,000×g at 4° C. The supernatant was discarded while the pellet (containing membranes) was resuspended in homogenization buffer, and the membranes were aliquoted and frozen at −80° C. Binding activity of test compounds was determined in 96-well plates containing 2 µl of test compound (in 100% DMSO) then 100 µl of [$^{125}$I]-DOI (catalog number NEX255, PerkinElmer™ Life Sciences; 0.1 nM final concentration) which had been diluted in assay buffer (50 mM HEPES pH 7.4, 0.5 mM EDTA, 0.5 mM EGTA, 37.5 mM KCl, 2.5 mM MgCl$_2$) followed by 100 µl of $5HT_{2a}$-expressing membranes which had been diluted in assay buffer. 1 µM mianserin was used to calculate non-specific binding. Assay plates were incubated for 60 minutes at 37° C., after which the assay was terminated by filtration onto UniFilter™ plates (with GF/C filters—from PerkinElmer™) that had been pre-soaked in 0.3% PEI. The filterplates were washed 2× with cold wash buffer (50 mM Tris, pH 7.4), then dried, scintillation fluid added and radioactivity determined in a Wallac Microbeta™ plate scintillation counter (PerkinElmer™). Concentration-response curves of the % inhibition of specific binding by test compounds versus the test compound concentration, was used to determine the $IC_{50}$ for each compound and the Ki value calculated based on the Cheng-Prusof equation (Ki=IC50/(1+(L/Kd)), where L is the concentration of the radioligand used in the binding assay and the Kd is based on previous saturation studies with the radioligand.

$5HT_{2b}$ Binding Procedure

Affinity of compounds for the human $5HT_{2b}$ receptor is determined by competition binding using membranes prepared from Chinese hamster ovary (CHO) cells containing the tetracycline operator (Flp-In Trex system—Invitrogen) that were engineered to express the human $5HT_{2b}$ receptor. Membranes were prepared from cells that had been incubated in dialyzed fetal bovine calf serum (FBS) for the previous 18 hours, in the presence of 1 µM doxicycline, and the membranes were stored at −80° C. To prepare the membranes, cells were harvested from flasks by centrifugation, then resuspended in homogenization buffer (10 mM HEPES, pH 7.5, 0.25 M sucrose, 1 mM EDTA, 1 mM EGTA containing the following protease inhibitors: 0.1 mg/ml benzamidine (Sigma™ B 6506), 0.1 mg/ml bacitracin (Sigma™ B 0125), 0.005 mg/ml leupeptin (Sigma™ L 8511), 0.5 mg/ml aprotinin (Sigma™ A1153) on ice. Cells are incubated in a centrifuge tube on ice for 10 minutes, then homogenized using four 10-second bursts of a Polytron™ homogenizer (Brinkman™), and then centrifuged at 1000×g for 10 minutes at 4° C. The supernatant was carefully removed and transferred to new centrifuge tubes, then centrifuged for 20 minutes at 25,000×g at 4° C. The supernatant was removed and discarded, while the pellet was resuspended in homogenization buffer, then centrifuged for 20 minutes at 25,000×g at 4° C. The supernatant was discarded while the pellet (containing membranes) was resuspended in homogenization buffer, and the membranes were aliquoted and frozen at −80° C. The binding assay was set up in 96-well plates, which contained 2 µl of test compound (in 100% DMSO) then 100 µl of $^3$H-LSD (final concentration=3 nM) diluted in assay buffer (50 mM Tris pH 7.4, 4 mM CaCl$_2$, 0.1% Ascorbic Acid), followed by the addition of 100 µl of membranes (approximately 15 µg membrane protein, diluted in assay buffer) from $5HT_{2b}$-expressing cells. 1 µM mianserin was used to calculate non-specific binding. The assay plates were incubated at 37° C. for 60 minutes, then the assay was terminated by filtration onto 96-well UniFilter™ plates (with GF/C filters—from PerkinElmer™) which were pre-soaked in 0.3% PEI. The filterplates were washed 2× with cold wash buffer (50 mM Tris, pH 7.4), then dried, scintillation fluid added and radioactivity determined in a Wallac Microbeta™ plate scintillation counter (PerkinElmer™). Concentration-response curves of the % inhibition of specific binding by test compounds versus the test compound concentration, was used to determine the $IC_{50}$ for each compound and the Ki value calculated based on the Cheng-Prusoff equation (Ki=IC50/(1+(L/Kd)), where L is the concentration of the radioligand used in the binding assay and the Kd is based on previous saturation studies with the radioligand.

Determination of potencies in binding assays provides an indication of the ability of a compound to displace another compound from the active site of the receptor. In other words, binding assays provide information on the ability of a test compound to interact with the receptor, but not on the ability of the compound to activate or block activation of the receptor. Whereas, functional assays are able to provide indication of the compound to activate a receptor or block the activation of the receptor as a consequence of prior binding. Activation or blockade of the activation of the receptor are what leads to the physiological activities of the ligands. Agonistic activity at a receptor and antagonistic activity at a receptor are completely different from one another and lead to very different and often opposing pharmacological responses. Consequently, the following assays provide useful information with respect to the mode of activation.

Functional Assays

In Vitro Functional Assays

Swiss 3T3 cells expressing r-$5HT_{2c}$, r-$5HT_{2a}$, h-$5HT_{2c}$, h-$5HT_{2a}$ or CHO cells expressing Tet-inducible h-$5HT_{2b}$ (co-expressing with G□16) receptors are seeded at a densities of 12,500 cells/well for $5HT_{2c}$ and $5HT_{2a}$ cells and at 25,000 cells/well for $5HT_{2b}$ cells in 384 well black/clear collagen-coated plates. All cells were grown in culture media supplemented with 10% fetal bovine serum. Twenty four (24) hours later culture media was replaced with media supplemented with 10% dialyzed serum. $5HT_{2b}$ cells were induced in the presence of 1 µg/ml doxycyclin in culture media with dialyzed serum. Twenty four (24) hours later the cells are loaded with the calcium sensitive dye, Fluo 4-AM™ (4 µM dissolved in DMSO containing pluronic acid) in serum free DMEM in the presence of probenicid (2.6 mM) for 75 minutes at 37° C. in a CO$_2$ incubator. Unincorporated dye is removed by washing 3 times with a HEPES-buffer containing probenicid (2.6 mM) using an EMBLA cell washer (final volume 30 µl).

Plates are added to a fluorometric imaging plate reader (FLIPR 384™ available from Molecular Devices Corporation) individually and fluorescence measurements are taken every 2 seconds over an 90 seconds period. Test compound additions are made simultaneously to all 384 wells after 20 seconds of baseline recording. Concentration-response curves are generated using XLDA and agonist efficacies are generated as % of the response to 10 µM 5-HT (considered as 100%). Estimation of antagonist potencies (functional Ki's)

are generated by measuring inhibition of the test compound response to 5-HT (10 nM for 5-HT$_{2c}$ and 5HT$_{2b}$, 50 nM for 5-HT$_{2a}$) and applying the Cheng Prusoff equation.

Compounds of the present invention have a binding Ki at human 5-HT$_{2c}$ receptors of less than 1,000 nM and greater than 0.1 nM. Compounds of the present invention typically have a binding Ki below 500 nM and exhibit serotonin receptor 2c agonist activity.

Preferred compounds have a binding Ki at human 5-HT$_{2c}$ receptors of less than 200 nM. More preferred compounds have a binding Ki below 100 nM.

The compounds of the present invention are not full agonists at the 5HT$_{2a}$ and 5HT$_{2b}$ receptors. They are antagonists or weak partial agonists at the 5-HT$_{2a}$ and 5-HT$_{2b}$ receptors. Also, compounds of the invention exhibit good selectivity for the 5HT$_{2c}$ receptor. The compounds of the present invention are functionally selective for 5-HT$_{2c}$ against 5-HT$_{2a}$ and 5-HT$_{2b}$, by virtue of their much greater agonistic potency (lower EC$_{50}$) for 5-HT$_{2c}$ than that observed for 5-HT$_{2a}$ and/or 5-HT$_{2b}$ or their lack of agonistic activity at 5-HT$_{2a}$ and/or 5-HT$_{2b}$.

Some of the compounds of the invention were found to have receptor binding data as follows:

| Example No. | 2cKi (nM) | 2aKi (nM) | 2bKi (nM) |
|---|---|---|---|
| 1A-37 | 26.6 | 25.0 | 159 |
| 2A-4 | 6.9 | 33.9 | 803 |
| 3A-79 | 12.9 | 43.9 | 332 |
| 3A-76 | 3.0 | 2.8 | 53 |
| 3A-83 | 17.9 | 46.8 | 145 |
| 4A-4 | 5.11 | 4.14 | 21 |
| 5B-6 | 5.82 | 7.11 | 12 |

Obesity and Related Disorders

Spontaneous Food Intake

The following screen is used to evaluate the efficacy of test compounds for inhibiting spontaneous food intake in Sprague-Dawley rats.

Male Sprague-Dawley rats may be obtained from Charles River Laboratories, Inc. (Wilmington, Mass.). The rats are individually housed and fed powdered chow. They are maintained on a 12 hour light/dark cycle and received food and water ad libitum. The animals are acclimated to the vivarium for a period of one week before testing is conducted. Rats are transferred to individual test cages 30 hours before the study. The rats are administered test compound or vehicle alone (no compound) 15-30 minutes prior to the onset of the dark cycle. The test compounds are dosed at ranges between 0.1 and 100 mg/kg depending upon the compound. The standard vehicle is 0.5% (w/v) methylcellulose or 30% β-cyclodextrin in water and the standard route of administration is oral. However, different vehicles and routes of administration are used to accommodate various compounds when required.

Food intake is monitored using an automated Columbus Instruments system (Columbus, Ohio). Individual rat food intake is recorded continuously at 10-minute intervals, starting at the time of dosing, for a period of at least 12 hours. Compound efficacy is determined by comparing the food intake pattern of compound-treated rats to vehicle.

Schizophrenia and Related Disorders

The compounds of the present invention are useful in the treatment of Schizophrenia and related disorders. This activity can be demonstrated in models using well-established procedures. For example, the compounds of the present invention may be assessed in a number of standard behavioural tests predictive of antipsychotic activity. For example, apomorphine-induced climbing behaviour and hypothermia in mice (see, e.g., Moore, N. A. et al. *Psychopharmacology* 94 (2), 263-266 (1988), and 96, 539 (1988)). Conditioned Avoidance Responding (inhibition of CAR) has been a classic and effective test used for the detection of drugs with potential antipsychotic activity, primarily developed to test neuroleptics acting through dopamine receptor blockade). Similarly, effects in d-Amphetamine locomotor (antagonism of the increased activity produced by d-amphetamine to show dopamine receptor blockade) and PCP locomotor (antagonism of the increased activity produced by the activation of dopamine neuronal function by the non-competitive N-methyl-D-aspartate (NMDA) receptor antagonist; phencyclidine (PCP)) assays can be used to predict anti-psychotic activity. At least one compound of the present invention has been shown to be active in the following protocols.

Locomotor & Stimulant-Induced Locomotor Activity

The locomotor activity boxes consist of 48 individual plexiglass behavioral chambers (30 cm×30 cm) enclosed in sound attenuating cabinets. A single 10 watt bulb in each cabinet is controlled by a 24 hour timer, which allows the behavioral to be maintained on any light/dark cycle desired. The plexiglass chambers are fitted with grid floors which are divided into quadrants and a metal touchplate positioned 7 cm from the floor on all four walls of the chamber. Horizontal locomotor activity is measured as the number of cross-overs an animal makes from one quadrant to another within its chamber. When the animal stands up (rears) and makes contact with the metal touchplate it is recorded by the computer as vertical locomotor activity.

Subjects are placed in the chambers overnight (approx. 15 hours) prior to the experiment. The next day each animal is weighed and treated with the test compound and then immediately returned to the test chamber. At a set pretreatment time, subjects are removed from the test chamber and treated with phencyclidine hydrochloride (3.2 mg/kg, sc), or d-Amphetamine sulphate (1 mg/kg, sc) and then immediately returned to the test chamber. Horizontal movements (cross-overs) are recorded by a computer for a three-hour test period.

In order to measure spontaneous locomotor activity, each animal is weighed and treated with the test compound one hour prior to being placed in the activity box. The test is always started as soon after the dark cycle (4 pm) as possible so that the effects of the compound can be observed during the animals' most active time. The apparatus is programmed to collect data overnight for a 12-hour period.

The computer is programmed to perform statistical analysis at given intervals. A one-way ANOVA is used to determine whether a difference due to treatment exists and is followed by Dunnett's multiple range test to determine differences between the control and experimental groups. Timed intervals of data (cross-overs) are analyzed individually and cumulatively for the duration of the experiment.

Conditioned Avoidance Response

Male CF rats (Charles River, Fisher-344 strain) are used in all experiments. Weights are approximately 350-400 grams at the time of testing. Animals are housed 2 per cage in environmentally controlled animal quarters (light/dark-4 am/4 pm). The conditioned avoidance shuttle chambers consist of 8 individual Plexiglas behavior chambers (Coulbourn Instruments™) each divided by a guillotine door into two sides, enclosed in sound attenuating cabinets. The Plexiglas chambers are fitted with metal grid floors, which are equipped with scrambled/constant current shockers.

Rats are trained to avoid the onset of footshock (1.5 miliampere, preceded for 5 seconds by activation of house lights, que lights, and the opening of the guillotine door) by moving to the opposite side of the chamber. Thirty trials are completed per daily session, and the number of avoidance's (max 30), escapes (max 30), escape failures (max 30), latency to avoid (max 5 sec.), latency to escape (max. 10 sec.), and adaptation crossovers (number of crossovers for a five minute period before the onset of trials, dark chamber) are recorded by the computer program. Inter-trial intervals are 30 seconds with the guillotine door closed. Drug treatment begins (30 minutes prior to session, s.c.) when rats have reached criteria of 80% avoidances for a session. Testing is performed during the lights on period of the light/dark cycle, typically between 8 am and 10 am.

Vehicle treatment is performed one day every week and statistical analysis is done comparing each drug treatment on separate days vs. the vehicle treatment that week. Testing is performed during the lights on period of the light/dark cycle, typically between 8 am and 10 am. The data is analyzed following importation into a spreadsheet using a t-test.

Anxiety and Related Disorders

Activity of compounds of the present invention for the treatment of anxiety and related disorders can be demonstrated in models using well-established procedures. For example, the following model may be used.

Acute Stress-Related Cerebellar cGMP Assay

Acute Stress Procedure: CF-1 mice (Charles River Laboratories) weighing 19-22 g are ordered one week prior to testing and are handled for two days before the experiment to reduce stress-related changes in basal cGMP levels. Animals are housed on a 12 hr light:dark schedule (6 a-6 p) in a temperature and humidity controlled room with free access to food and water.

After dosing (typically 30-60 min depending on drug), animals to be stressed are placed into a Coulbourn chamber with a steel grid floor and shocked at 1 mA for 10 seconds. Immediately following the stressor mice are placed into a plastic restraint tube and sacrificed using a beam of microwave irradiation focused on the head (2.0 kW for 0.9 sec) using a Gerling-Moore Metabostat. The cerebellum is then rapidly removed, snap frozen in liquid nitrogen, and stored at −80 C prior to the cGMP assay. Non-stressed animals are taken directly from their home cages, sacrificed by microwave irradiation and processed the same.

cGMP Assay: Whole cerebella are weighed and then homogenized in 1 ml of 1% perchloric acid in dd-water using a Brinkman Polytron at 15,000 rpm for about 15 sec each and placed on ice until all samples are homogenized.

Samples are then placed into an 85 C water bath for 5 min, centrifuged at 2500×g for 15 min at 4 C, and about 0.5 ml of the supernatant is collected for analysis.

Supernatants are diluted 1:5 in 0.05M sodium acetate buffer (pH 5.8). All other assay steps proceed according to the directions of the manufacturer of the cGMP EIA kits (Amersham Biosciences). Diluted samples are incubated overnight in treated 96-well plates and processed the following day. Samples are read at 450 nm optical wavelength and converted to pmol cGMP/mg tissue using a standard curve generated in the same experiment.

Sexual Dysfunction

Treatment of MED

Compounds of the present invention can be screened for effect of penile intracavernosal pressure (ICP) in the conscious male rat according to the methods described hereinbelow.

ICP Protocol: Intra cavernosal pressure (ICP) can be measured in the conscious rat by means of telemetric recording. A catheter is surgically implanted into the corpus cavemosum. The end of the catheter is linked to a device, which senses, processes, and transmits information digitally from within the animal. A receiver converts the radio-frequency signal from the implant to a digital pulse stream that is readable by a data collection system. The PC-based system collects telemetred data from the animal.

Surgery:—Induce and maintain general anaesthesia using 5% Isoflurane® in a carrier gas of 0.5 liter/minute oxygen and 1 liter/minute nitrous oxide to induce anaesthesia, reducing to 2% Isoflurane for maintenance anaesthesia. Administer 5mg/kg sub cutaneously (s.c.) Carprofen (Rimadyl® Large Animal Injection, 50 mg/ml, Pfizer Animal Health) at induction of anaesthesia, at end of day of surgery and on the morning of first day post-surgery to minimize pain and discomfort.

Implantation of corpus cavernosal probe:—Shave the skin of the ventral abdomen and extend to include the area around the penis and ventral scrotum. Clean and disinfect the shaved area. Place the rat in dorsal recumbency. Make a mid-line incision from the external base of the penis, running caudally for approximately 2 cm. Locate and expose the internal structure of the penis and identify the corpus cavernosum. Make a mid-line laparotomy, approximately 4 cm in length to access the abdominal cavity. Pierce the abdominal wall via the caudal incision with a suitable trocar and cannula, taking care not to damage any internal organs. Place the implant body in the abdominal cavity with the catheter orientated caudally and pass the catheter tip through the body wall via the preplaced cannula. A model TA11PA-C40, 8 mm catheter implant may be used a with modified 3 mm tip (Data Sciences International Inc.). Secure the implant body to the abdominal wall using non-absorbable sutures and partially close the abdominal incision. Reflect the tip of the penis cranially and retract the caudal incision to optimize the surgical field. Carefully isolate approximately 10 mm of the internal structure of the penis from the surrounding tissue. Carefully reflect the corpus spongiosum to one side to give access to the corpus cavernosum. Access the corpus cavernosum using a modified over-the-needle catheter to puncture the tunica. Introduce the catheter tip via the preplaced catheter and advance until fully inserted. Carefully remove the access catheter and apply a suitable tissue adhesive to the insertion site. Observe for leakage. Close the subcutaneous fat layer in the caudal incision before closing with an appropriate absorbable suture. Instil approximately 5 ml of warm saline through the abdominal incision and complete closure of the mid-line incision. Close the skin incision with an appropriate absorbable suture.

Postoperative care:—Measure food and water intake and monitor bodyweight daily for at least 7 days post surgery, then 2-3 times weekly. Give Lectade® (Pfizer Animal Health) in drinking water for 3 days post surgery. House rats singly, and transfer to reverse light/dark conditions 5 days post surgery. Named Veterinary Surgeon (or Deputy) to issue a certificate of fitness to continue 2 days post surgery. Start using rats experimentally 7 days post surgery.

Experimental Procedure:—Perform experiment in room with reverse light/dark conditions. On day of experiment, place rat in home cage on receiver pad (PhysioTel® Model RPC-1, Data Sciences International Inc.) and leave to acclimatize for approximately one hour. Ensure that the rat has food and water ad lib. Take baseline reading of intra cavernosal pressure (ICP) for approximately 5 minutes. Transfer the data via a floppy disk to an Excel spreadsheet. Inject the rat with compound subcutaneously or via the jugular vein catheter (JVC). If using the JVC, flush through with sterile saline after dosing and seal with a saline/glucose lock solution. The interval between administration of compound and ICP measurement will vary with the compound to be tested. An interval of 30-60 min post s.c. injection is a good guide. The test compounds are dissolved in 50% β-cyclodextrin in saline. They are administered at a dose of 5-10 mg/kg subcutaneously (s.c.). Apomorphine hydrochloride hemihydrate (Sigma™ A-4393) at 60 µg/kg s.c. is used as a positive control as it has pro-erectile properties. Record ICP over a 15 minute period, starting at 30 minutes post injection i.e. from 30 to 35 minutes and repeat for two further 15 minute periods commencing at 60 minutes post injection and 120 minutes post injection respectively. Record ICP for 15 minutes. A signal from the receiver pad feeds through to the Data Exchange Matrix® and hence to the software (Dataquest ART® acquisition system, Data Sciences International Inc.). Transfer the data via a floppy disk to an Excel spreadsheet for analysis.

Combination with PDE5 Inhibitor for Treatment of MED

The effects of concomitant administration of a compound of the present invention in combination with a PDE5 inhibitor (PDE5i) on the penile intracavernosal pressure (ICP) in an anaesthetised rabbit model of erection can be measured according to the following protocol.

Experimental Protocol

Male New Zealand rabbits (~2.5 kg) are pre-medicated with a combination of Medetomidine (Domitor®V) 0.5 ml/kg inramuscularly (i.m.), and Ketamine (Vetalar®) 0.25 ml/kg i.m. whilst maintaining oxygen intake via a face mask. The rabbits are tracheotomised using a Portex™ uncuffed endotracheal tube 3 ID (internal diameter), connected to ventilator and maintained at a ventilation rate of 30-40 breaths per minute, with an approximate tidal volume of 18-20 ml, and a maximum airway pressure of 10 cm $H_2O$. Anaesthesia is then switched to Isoflurane® and ventilation continued with $O_2$ at 2 litres/min. The right marginal ear vein is cannulated using a 23 G or 24 G catheter, and Lactated Ringer solution perfused at 0.5 ml/min. The rabbit is maintained at 3% Isoflurane during invasive surgery, dropping to 2% for maintenance anaesthesia. The left jugular vein is exposed, isolated and then cannulated with a PVC catheter (17 gauge/ 17 G) for the infusion of drugs and the test compounds.

The left groin area of the rabbit is shaved and a vertical incision is made approximately 5 cm in length along the thigh. The femoral vein and artery are exposed, isolated and then cannulated with a polyvinylchloride (PVC) catheter (17 G) for the infusion of drugs and compounds. Cannulation is repeated for the femoral artery, inserting the catheter to a depth of 10 cm to ensure that the catheter reaches the abdominal aorta. This arterial catheter is linked to a Gould system to record blood pressure. Samples for blood gas analysis are also taken via the arterial catheter. Systolic and diastolic pressures are measured, and the mean arterial pressure calculated using the formula (diastolic ×2+systolic)÷3. Heart rate is measured via the pulse oxymeter and a Po-ne-mah data acquisition software system (Ponemah Physiology Platform, Gould Instrument Systems Inc).

A ventral midline incision is made into the abdominal cavity. The incision is about 5 cm in length just above the pubis. The fat and muscle is bluntly dissected away to reveal the hypogastric nerve which runs down the body cavity. It is essential to keep close to the side curve of the pubis wall in order to avoid damaging the femoral vein and artery which lie above the pubis. The sciatic and pelvic nerves lie deeper and are located after further dissection on the dorsal side of the rabbit. Once the sciatic nerve is identified, the pelvic nerve is easily located. The term pelvic nerve is loosely applied; anatomy books on the subject fail to identify the nerves in sufficient detail. However, stimulation of the nerve causes an increase in intracavernosal pressure and cavernosal blood flow, and innervation of the pelvic region. The pelvic nerve is freed away from surrounding tissue and a Harvard bipolar stimulating electrode is placed around the nerve. The nerve is slightly lifted to give some tension, then the electrode is secured in position. Approximately 1 ml of light paraffin oil is placed around the nerve and electrode. This acts as a protective lubricant to the nerve and prevents blood contamination of the electrode. The electrode is connected to a Grass S88 Stimulator. The pelvic nerve is stimulated using the following parameters:—5V, pulse width 0.5 ms, duration of stimulus 20 seconds with a frequency of 16 Hz. Reproducible responses are obtained when the nerve is stimulated every 15-20 minutes. Several stimulations using the above parameters are performed to establish a mean control response. The compound(s) to be tested are infused, via the jugular vein, using a Harvard 22 infusion pump allowing a continuous 15 minute stimulation cycle. The skin and connective tissue around the penis is removed to expose the penis. A catheter set (Insyte-W, Becton-Dickinson 20 Gauge 1.1×48 mm) is inserted through the tunica albica into the left corpus cavernosal space and the needle removed, leaving a flexible catheter. This catheter is linked via a pressure transducer (Ohmeda 5299-04) to a Gould system to record intracavernosal pressure (ICP). Once an intracavernosal pressure is established, the catheter is sealed in place using Vetbond (tissue adhesive, 3M). Heart rate is measured via the pulse oxymeter and a Po-ne-mah data acquisition software system (Ponemah Physiology Platform, Gould Instrument Systems Inc).

Intracavernosal blood flow is recorded either as numbers directly from the Flowmeter using Po-ne-mah data acquisition software (Ponemah Physiology Platform, Gould Instrument Systems Inc), or indirectly from Gould chart recorder trace. Calibration is set at the beginning of the experiment (0-125 ml/min/100 g tissue).

All data is reported as mean±s.e.m. (standard error of the mean). Significant changes are identified using Student's t-tests. The test compounds are dissolved in 50% β-cyclodextrin in saline. They are administered at a dose of 5-10 mg/kg subcutaneously (s.c.).

Using the protocol described hereinbefore beneficial effects on ICP can be demonstrated for the concomitant administration of a compound of the present invention (5-10 mg/kg s.c.) and a selective inhibitor of PDE5 (3-ethyl-5-{5-[4-ethylpiperzino)sulphonyl-2-propoxyphenyl}-2-(2-pyridylmethyl)-6,7-dihydro-2H-pyrazolo[4,3-d]pyrimidin-7-one (as described in WO98/491066) (1 mg/kg i.v. (intravenously)). A number of clinical benefits of concomitant administration of a PDE5 inhibitor and a compound of the present invention may be realized. Such benefits include increased efficacy and opportunities to treat MED subgroups that do not respond to other MED mono-therapies.

Treatment of FSAD

Serotonin $5HT_{2c}$ receptor agonists are known to potentiate pelvic nerve-stimulated increases in female genital blood flow in the anaesthetised rabbit model of sexual arousal.

The normal sexual arousal response consists of a number of physiological responses that are observed during sexual excitement. These changes such as vaginal, labial and clitoral engorgement result from increases in genital blood flow. Engorgement leads to increased vaginal lubrication via plasma transudation, increased vaginal compliance (relaxation of vaginal smooth muscle) and increases in vaginal and clitoral sensitivity.

Female sexual arousal disorder (FSAD) is a highly prevalent sexual disorder affecting up to 40% of pre-, peri- and postmenopausal (±HRT) women. The primary consequence of FSAD is reduced genital engorgement or swelling which manifests itself as a lack of vaginal lubrication and a lack of pleasurable genital sensation. Secondary consequences include reduced sexual desire, pain during intercourse and difficulty in achieving orgasm. The most common cause of FSAD is decreased genital blood flow resulting in reduced vaginal, labial and clitoral engorgement (Berman, J., Goldstein, I., Werbin, T. et al. (1999a). Double blind placebo controlled study with crossover to assess effect of sildenafil on physiological parameters of the female sexual response. *J. Urol.*, 161, 805; Goldstein, I. & Berman, J. R. (1998). Vasculogenic female sexual dysfunction: vaginal engorgement and clitoral erectile insufficiency syndromes. *Int. J. Impot Res.*, 10, S84-S90; Park, K., Goldstein, I., Andry, C., et al. (1997). Vasculogenic female sexual dysfunction: The hemodynamic basis for vaginal engorgement insufficiency and clitoral erectile insufficiency. *Int. J. Impotence Res.*, 9, 27-37; Werbin, T., Salimpour, P., Berman, L., et al. (1999). Effect of sexual stimulation and age on genital blood flow in women with sexual stimulation. *J. Urol.*, 161, 688).

As explained herein, the present invention provides a means for restoring or potentiating the normal sexual arousal response in women suffering from FSAD, by enhancing genital blood flow. The following describes a method for testing such response.

FSAD Method

Female New Zealand rabbits (~2.5 kg) are pre-medicated with a combination of Medetomidine (Domitor®) 0.5 ml/kg intramuscularly (i.m.), and Ketamine (Vetalar®) 0.25 ml/kg i.m. while maintaining oxygen intake via a face mask. The rabbits are tracheotomised using a Portex™ uncuffed endotracheal tube 3 ID (internal diameter), connected to ventilator and maintained at a ventilation rate of 30-40 breaths per minute, with an approximate tidal volume of 18-20 ml, and a maximum airway pressure of 10 cm $H_2O$. Anaesthesia is then switched to Isoflurane® and ventilation continued with $O_2$ at 2 l/min. The right marginal ear vein is cannulated using a 23 G or 24 G catheter, and Lactated Ringer solution perfused at 0.5 ml/min. The rabbit is maintained at 3% Isoflurane® during invasive surgery, dropping to 2% for maintenance anaesthesia.

The left groin area of the rabbit is shaved and a vertical incision is made approximately 5 cm in length along the thigh. The femoral vein and artery are exposed, isolated and then cannulated with a PVC catheter (17 G) for the infusion of drugs and compounds. Cannulation is repeated for the femoral artery, inserting the catheter to a depth of 10 cm to ensure that the catheter has reached the abdominal aorta. This arterial catheter is linked to a Gould system to record blood pressure. Samples for blood gas analysis are also taken via the arterial catheter. Systolic and diastolic pressures are measured, and the mean arterial pressure calculated using the formula (diastolic×2+systolic)÷3. Heart rate is measured via the pulse oxymeter and Po-ne-mah data acquisition software system (Ponemah Physiology Platform, Gould Instrument Systems Inc).

A ventral midline incision is made into the abdominal cavity. The incision is about 5 cm in length just above the pubis. The fat and muscle is bluntly dissected away to reveal the hypogastric nerve which runs down the body cavity. It is essential to keep close to the side curve of the pubis wall in order to avoid damaging the femoral vein and artery, which lie above the pubis. The sciatic and pelvic nerves lie deeper and are located after further dissection on the dorsal side of the rabbit. Once the sciatic nerve is identified, the pelvic nerve is easily located. The term pelvic nerve is loosely applied; anatomy books on the subject fail to identify the nerves in sufficient detail. However, stimulation of the nerve causes an increase in vaginal and clitoral blood flow, and innervation of the pelvic region. The pelvic nerve is freed away from surrounding tissue and a Harvard bipolar stimulating electrode is placed around the nerve. The nerve is slightly lifted to give some tension, then the electrode is secured in position. Approximately 1 ml of light paraffin oil is placed around the nerve and electrode. This acts as a protective lubricant to the nerve and prevents blood contamination of the electrode. The electrode is connected to a Grass S88 Stimulator. The pelvic nerve is stimulated using the following parameters:—5V pulse width 0.5 ms, duration of stimulus 10 seconds and a frequency range of 2 to 16 Hz. Reproducible responses are obtained when the nerve is stimulated every 15-20 minutes. A frequency response curve is determined at the start of each experiment in order to determine the optimum frequency to use as a sub-maximal response, normally 4 Hz. A ventral midline incision is made, at the caudal end of the pubis, to expose the pubic area. Connective tissue is removed to expose the tunica of the clitoris, ensuring that the wall is free from small blood vessels. The external vaginal wall is also exposed by removing any connective tissue. One laser Doppler flow probe is inserted 3 cm into the vagina, so that half the probe shaft is still visible. A second probe is positioned so that it lay just above the external clitoral wall. The position of these probes is then adjusted until a signal is obtained. A second probe is placed just above the surface of a blood vessel on the external vaginal wall. Both probes are clamped in position.

Vaginal and clitoral blood flow is recorded either as numbers directly from the Flowmeter using Po-ne-mah data acquisition software (Ponemah Physiology Platform, Gould Instrument Systems Inc), or indirectly from Gould chart recorder trace. Calibration is set at the beginning of the experiment (0-125 ml/min/100 g tissue). All data are reported as mean±standard error of the mean (s.e.m.). Significant changes are identified using Student's t-tests.

Lower Urinary Tract Dysfunction (Including Urinary Incontinence)

Activity of the compounds of the present invention on lower urinary tract function, and thus their potential usefulness in treating conditions involving lower urinary tract dysfunction, can be investigated and assessed utilising a number of standard in vivo models known to those skilled in the art and frequently described in the literature (Morrison, J., et al., Neurophysiology and Neuropharmacology. In: Incontinence, Ed. Abrams, P., Cardozo, C., Khoury, S. and Wein, A. Report of the World Health Organisation Consensus Conference. Paris, France: Health Publications Ltd., 2002: 83-163; Brune M E et al. Comparison of alpha 1-adrenoceptor agonists in canine urethral pressure profilometry and abdominal leak point pressure models. J Urol. 2001, 166:1555-9; Schroder et al. (2003) J. Urol. 170, 1017-1021). As an example, compounds of the present invention can be tested for such effects in the models described herein below.

Bladder Capacity and External Urethral Sphincter (EUS) Function in the Guinea-Pig Experiments are performed in adult female guinea pigs, weighing approx 500 g. All animals are initially anaesthetised with halothane (4%), carried in oxygen (3-4L $min^{-1}$) and maintained at an appropriate surgical plane with urethane (25% w/v; 0.5 ml 100 $g^{-1}$ body weight). The trachea, a jugular vein and a carotid artery are cannulated for respiratory ventilation, injection of test compound and monitoring of blood pressure, respectively. A midline laparotomy is performed to expose the urinary bladder and a cystometry tube inserted through a small incision in the dome of the bladder and secured in place. The abdominal wound is then closed tightly around the externalised cystometry tube, which, in turn, is connected to an infusion pump and pressure transducer, for filling the bladder and recording intravesical pressure, respectively. Electromyographic (EMG) wire leads are inserted into the EUS striated muscle layer opposed to the dorsal surface of the symphysis pubis. The EMG leads are connected to an appropriate amplification and electrical filter system and changes in EUS electrical activity displayed on an oscilloscope and recorded through appropriate computer software.

Following a 30 min post surgery stabilisation period, the bladder is filled at a rate of 150 μl $min^{-1}$ with physiological saline (room temperature), until initiation of a micturition reflex is observed. Following micturition, the bladder is drained via the externalised cystometry tube. Bladder filling is then repeated at least 3 times (or until repeatable filling cycles are achieved) in order to establish a mean bladder threshold capacity for initiation of micturition. EUS EMG activity and intravesical (bladder) pressure are recorded throughout bladder filling. Subsequently, test compound or vehicle is injected intravenously utilising either a bolus dose or constant infusion and bladder filling re-initiated (150 μl $min^{-1}$) until micturition occurs, the bladder is then drained as before and the process repeated with addition of increasing doses of test compound (2 micturition responses are measured at each compound concentration). Changes in threshold bladder capacity initiating micturition and/or in EUS EMG activity are indicative of compound activity on lower urinary tract function.

Abdominal Leak Point Pressure in the Guinea-Pig

Experiments are performed in adult female guinea pigs, weighing approx 500 g. All animals are initially anaesthetised with halothane (4%), carried in oxygen (3-4 L $min^{-1}$) and maintained at an appropriate surgical plane with urethane (25% w/v; 0.5 ml 100 $g^{-1}$ body weight). The trachea, a jugular vein and a carotid artery are cannulated for respiratory ventilation, injection of test compound and monitoring of blood pressure, respectively. A midline laparotomy is performed to expose the urinary bladder and a cystometry tube inserted through a small incision in the dome of the bladder and secured in place. The abdominal wound is then closed tightly around the externalised cystometry tube, which, in turn, is connected to an infusion pump and pressure transducer, for filling the bladder and recording intravesical pressure, respectively. Electromyographic (EMG) wire leads are inserted into the EUS striated muscle layer opposed to the dorsal surface of the symphysis pubis. The EMG leads are connected to an appropriate amplification and electrical filter system and changes in EUS electrical activity displayed on an oscilloscope and recorded through appropriate computer software.

Following a 30 min post surgery stabilisation period, the bladder is filled at a rate of 150 μl $min^{-1}$ with physiological saline (room temperature), until initiation of a micturition reflex is observed. Following micturition, the bladder is drained via the externalised cystometry tube. Bladder filling is then repeated at least 3 times (or until repeatable filling cycles are achieved) in order to establish a mean bladder threshold capacity for initiation of micturition. EUS EMG activity and intravesical (bladder) pressure are recorded throughout bladder filling. Subsequently, the bladder is filled (150 μl $min^{-1}$) to 75% of this threshold volume with physiological saline and, through the use of a specially constructed frame, increasing weight is applied to the ventral surface of the abdomen of the animal just rostral to the position of the bladder until leakage of fluid is observed at the urethral meatus. This process is repeated at least 3 times in order to establish control responses; EUS EMG activity and intravesical pressure being recorded throughout. Subsequently increasing concentrations of test compound or vehicle is injected intravenously utilising either a bolus dose or constant infusion and weight induced leak responses re-investigated at each concentration. Changes in the abdominal weight required to induce leak and/or the maximum EUS EMG activity recorded immediately prior to leak are indicative of compound activity on lower urinary tract function.

Guinea-Pig Urethral Pressure Profilometry

Experiments are performed in adult female guinea pigs, weighing approx 500 g. All animals are initially anaesthetised with halothane (4%), carried in oxygen (3-4 L $min^{-1}$) and maintained at an appropriate surgical plane with urethane (25% w/v; 0.5 ml 100 $g^{-1}$ body weight). The trachea, a jugular vein and a carotid artery are cannulated for respiratory ventilation, injection of test compound and monitoring of blood pressure, respectively. A midline laparotomy is performed to expose the urinary bladder and a cystometry tube inserted through a small incision in the dome of the bladder and secured in place. The abdominal wound is then closed tightly around the externalised cystometry tube, which, in turn, is connected to an infusion pump and pressure transducer, for filling the bladder and recording intravesical pressure, respectively. Electromyographic (EMG) wire leads are inserted into the EUS striated muscle layer opposed to the dorsal surface of the symphysis pubis. The EMG leads are connected to an appropriate amplification and electrical filter system and changes in EUS electrical activity displayed on an oscilloscope and recorded through appropriate computer software.

Following a 30 min post surgery stabilisation period, the bladder is filled at a rate of 150 µl min$^{-1}$ with physiological saline (room temperature), until initiation of a micturition reflex is observed. Following micturition, the bladder is drained via the externalised cystometry tube. Bladder filling is then repeated at least 3 times (or until repeatable filling cycles are achieved) in order to establish a mean bladder threshold capacity for initiation of micturition. Subsequently, the bladder is filled (150 µl min$^{-1}$) to 75% of this threshold volume and urethral tone (peak urethral pressure (PUP), functional urethral length (FUL) and closing pressure (CP)) assessed with the aid of a 3 F Millar pressure transducer (Millar Instruments, Texas, US) inserted into the bladder through the external meatus. The urethral Millar pressure transducer is then retracted along the length of the urethra (urethral pull through) at a rate of 1 cm/min enabling the determination of PUP, FUL and CP. Urethral pull throughs are repeated every 2 min until 4 reproducible urethral profiles are observed. Subsequently increasing concentrations of test compound or vehicle is injected intravenously utilising either a bolus dose or constant infusion and a further 4 urethral pull throughs carried out at each concentration investigated. Changes in the PUP, FUL, CP or EUS EMG activity are indicative of compound activity on lower urinary tract function.

Dog Urethral Pressure Profilometry

Female beagle dogs (10-15 kg) are anaesthetised with sodium pentobarbitone (60 mg/mL solution) administered intravenously (IV) at 0.5 ml/kg via the right cephalic vein. Immediately following induction of anaesthesia the dog is intubated and respiration supported by artificial ventilation with oxygen. End tidal $CO_2$ is monitored continuously, using a Datex $CO_2/O_2$ monitor and maintained between. 4.5 and 4.8% and body temperature maintained between 37 C and 38° C. An incision is made in the right medial thigh and a polyethylene catheter (6 F) inserted into the right femoral vein for administration of compounds and fluid maintenance; immediately venous access is achieved a bolus IV dose of α-chloralose (1% w/v) is administered at 35 mg/kg. A polyethylene catheter (4 F) is inserted into the right femoral artery for blood sampling. An incision is made in the right foreleg and the brachial vein and artery isolated, maintenance of anaesthesia is achieved with α-chloralose/borax administered IV at the rate of 10 mg/kg/h via a polyethylene catheter (6 F) inserted into the right brachial vein. A laparotomy is performed from the umbilicus to the top of the pubic symphysis via the midline to expose the peritoneum in order to expose the bladder. Both ureters are cannulated towards the kidneys with polyethylene catheters (6 F) and urine collected externally; the bladder is catheterised through the dome with a polyethylene catheter (6 F), which is in turn connected to a pressure transducer. In order to maintain constant bladder pressure at 10-15 mmHg, urine is removed and ambient temperature saline infused into the bladder. Immediately following the completion of the surgical procedures a further bolus dose of α-chloralose/borax solution is administered IV at 35 mg/kg and the animal allowed to stabilise for a period ca. 1 hr, during which time haemodynamic and urological parameters were monitored.

Urethral tone (peak urethral pressure (PUP), functional urethral length (FUL) and closing pressure (CP)) is assessed with the aid of an 8 F Millar pressure transducer (Millar Instruments, Texas, US) inserted into the bladder through the external meatus. The urethral Millar pressure transducer is then retracted along the length of the urethra (urethral pull through) at a rate of 1 cm/min enabling the determination of PUP, FUL and CP. Urethral pull throughs are repeated every 6 min until 4 reproducible urethral profiles are observed. Subsequently increasing concentrations of test compound or vehicle is injected intravenously utilising either a bolus dose or constant infusion and a further 4 urethral pull throughs carried out at each concentration investigated. Changes in the PUP, FUL or CP are indicative of compound activity on lower urinary tract function.

Bladder Capacity and External Urethral Sphincter (EUS) Function in the Spontaneously Hypertensive Rat Experiments are performed in adult female spontaneously hypertensive rats (SHRs), weighing approx 250-300 g. All animals are initially anaesthetised with isoflurane (4%), carried in oxygen (3-4 L min$^{-1}$) and maintained at an appropriate surgical plane with urethane (25% w/v; 0.5 mi 100g$^{-1}$ body weight). The trachea, a jugular vein and a carotid artery are cannulated for respiratory ventilation, injection of test compound and monitoring of blood pressure, respectively. A midline laporatomy is performed to expose the urinary bladder and a cystometry tube inserted through a small incision in the dome of the bladder and secured in place. The abdominal wound is then closed tightly around the externalised cystometry tube, which, in turn, is connected to an infusion pump and pressure transducer, for filling the bladder and recording intravesical pressure, respectively. Electromyographic (EMG) wire leads are inserted into the EUS striated muscle layer opposed to the dorsal surface of the symphysis pubis. The EMG leads are connected to an appropriate amplification and electrical filter system and changes in EUS electrical activity displayed on an oscilloscope and recorded through appropriate computer software.

Following a 30 min post surgery stabilisation period, the bladder is filled at a rate of between 45 and 100 µl min$^{-1}$ with physiological saline (room temperature), until initiation of a micturition reflex is observed. Following micturition, the bladder is drained via the externalised cystometry tube. Bladder filling is then repeated at least 3 times (or until repeatable filling cycles are achieved) in order to establish a mean bladder threshold capacity for initiation of micturition. EUS EMG activity and intravesical (bladder) pressure are recorded throughout bladder filling. Subsequently, test compound or vehicle is injected intravenously utilising either a bolus dose or constant infusion and bladder filling re-initiated until micturition occurs, the bladder is then drained as before and the process repeated with addition of increasing doses of test compound (2 micturition responses are measured at each compound concentration). Changes in threshold bladder capacity initiating micturition and/or in EUS EMG activity are indicative of compound activity on lower urinary tract function.

Voided Volume in Conscious Ovariectomised Mice

Ovariectomised adult female mice are dosed (either orally or sub-cutaneously) with vehicle or increasing concentrations of compound and placed in individual metaboles with free access to water for 3 hr. Urine voided by each mouse is captured on a conical sponge within a container placed beneath each metabole, this sponge also deflects faecal pellets. The total volume of urine voided within the 3 hr period and the volume of urine per void is measured by a balance placed directly beneath the collection container. The average volume of urine per void and the frequency of voiding events are compared between vehicle and compound treated groups (up to n=16 per group), changes in these parameters in the absence of changes in the total urine output are indicative of compound activity on lower urinary tract function.

Voided volume and Bladder Activity in Conscious Telemeterised Spontaneously

Adult female spontaneously hypertensive rats are dosed (either orally or sub-cutaneously) with vehicle or increasing concentrations of compound and placed in individual metaboles with free access to water for 3 hr. Urine voided by each rat is captured on a conical sponge within a container placed beneath each metabole, this sponge also deflects faecal pellets. The total volume of urine voided within the 3 hr period and the volume of urine per void is measured by a balance placed directly beneath the collection container. The average volume of urine per void and the frequency of voiding events are compared between vehicle and compound treated groups (up to n=16 per group), changes in these parameters in the absence of changes in the total urine output are indicative of compound activity on lower urinary tract function.

What is claimed is:
1. A compound of Formula (I)

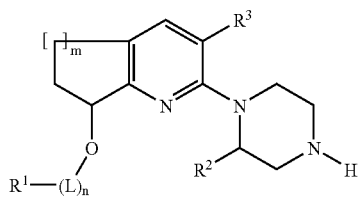

(I)

wherein;
m is 1 or 2;
n is 0 or 1;
L is —$CHR^{0a}$—, where $R^{0a}$ is hydrogen or ($C_1$-$C_4$)alkyl;
$R^2$ is hydrogen or methyl;
$R^3$ is selected from the group consisting of H, Cl, Br, F, $CH_3$ and CN;
$R^1$ is
(a) a group of Formula (IA)

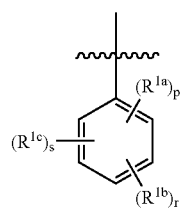

(IA)

where
(i) p, r and s are each independently 0 or 1, and
$R^{1a}$, $R^{1b}$ and $R^{1c}$ are each independently selected from the group consisting of F, Cl, Br 1, cyano, —$CH_2$—CN, —$NH_2$, —OH, ($C_1$-$C_6$)alkyl, ($C_1$-$C_6$)alkoxy, ($C_1$-$C_4$)alkylthio, fluoro-substituted ($C_1$-$C_4$)alkyl, fluoro-substituted ($C_1$-$C_4$)alkoxy, fluoro-substituted ($C_1$-$C_4$)alkylthio, —NH—C(O)—($C_1$-$C_4$)alkyl, —C(O)—($C_1$-$C_4$)alkyl, —C(O)—O($C_1$-$C_4$)alkyl, —C(O)—$NH_2$, —C(O)—NH($C_1$-$C_4$)alkyl, a 3- to 6-membered carbocyclic ring, and phenyl substituted with F, Cl, Br or I; or
(ii) p and r are each 0,
s is 1, and
$R^{1c}$ is independently selected from the group consisting of phenyl, phenoxy optionally substituted with F, Cl, Br, or I; benzyl, benzyloxy, —NH($C_1$-$C_4$)alkyl, —N[($C_1$-$C_4$)alkyl]$_2$, —$CH_2$—NH($C_1$-$C_4$)alkyl, —$CH_2$—N[($C_1$-$C_4$)alkyl]$_2$, —NH(phenyl), —NH(5- to 6-membered heteroaryl containing 1 to 3 hetero atoms independently selected from O, N, and S, which is optionally substituted with 1 to 3 halo groups), —N($CH_3$)—$SO_2$($C_1$-$C_4$)alkyl, —NH—$SO_2$($C_1$-$C_4$)alkyl, —NHC(O)$NH_2$, —C(O)—N[($C_1$-$C_4$)alkyl]$_2$, —C(O)-(5- to 6-membered heterocycle containing 1 to 3 hetero atoms independently selected from O, N, and S), —C(O)—NH(5- to 6-membered heterocycle containing 1 to 3 hetero atoms independently selected from O, N, and S), —C(O)-(5- to 6-membered carbocycle), —$CH_2$—C(O)—O($C_1$-$C_4$) alkyl, a 3- to 6-membered heterocyclic ring containing 1 to 3 heteroatoms independently selected from O, N or S, and a 5- to 6-membered heteroaryl containing 1 to 3 heteroaroms independently selected from O, N or S which is optionally substituted with one to three substituents independently selected from a F, Cl, Br, I, and $CF_3$;
(b) a 5- to 6-membered heteroaryl containing 1 to 3 heteroatoms independently selected from O, S or N, where said heteroaryl is optionally fused to a 5- to 6- membered carbocyclic ring or a 6-membered aromatic ring and said heteroaryl is optionally substituted with 1 to 2 substituents independently selected from the group consisting of cyano, F, Cl, Br, I, ($C_1$-$C_4$)alkyl, ($C_1$-$C_4$)alkoxy, and —C(O)—O($C_1$-$C_4$)alkyl; or a pharmaceutically acceptable salt thereof.

2. The compound of claim 1 wherein said compound of Formula (I) is a compound having Formula (II)

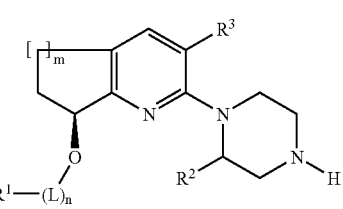

(II)

wherein m, n, L, $R^1$, $R^2$, and $R^3$ are as defined in claim 1; or a pharmaceutically acceptable salt thereof.

3. The compound of claim 1 wherein $R^2$ is (R)-methyl; or a pharmaceutically acceptable salt of said compound.

4. The compound of claim 2 wherein $R^2$ is (R)-methyl; or a pharmaceutically acceptable salt of said compound.

5. The compound of claim 1 wherein $R^{0a}$ is H or $CH_3$; or a pharmaceutically acceptable salt of said compound.

6. The compound of claim 1 wherein $R^3$ is H; or a pharmaceutically acceptable salt of said compound.

7. The compound of claim 1 wherein m is 1 and n is 1; or a pharmaceutically acceptable salt of said compound.

8. The compound of claim 7 selected from the group consisting of:
- (7S)-7-[(2,5-difluorobenzyl)oxy]-2-piperazin-1-yl-6,7-dihydro-5H-cyclopenta[b]pyridine;
- (7S)-7-[(3-fluorobenzyl)oxy]-2-[(2R)-2-methylpiperazin-1-yl]-6,7-dihydro-5H-cyclopenta[b]pyridine;
- (7S)-7-[(2-chlorobenzyl)oxy]-2-[(2R)-2-methylpiperazin-1-yl]-6,7-dihydro-5H-cyclopenta[b]pyridine;
- 3-[({(7S)-2-[(2R)-2-methylpiperazin-1-yl]-6,7-dihydro-5H-cyclopenta[b]pyrid in-7-yl}oxy)methyl]benzonitrile;
- (7S)-7-[(2,5-difluorobenzyl)oxy]-2-[(2R)-2-methylpiperazin-1-yl]-6,7-dihydro-5H-cyclopenta[b]pyridine;
- (7S)-7-[(2,5-dichlorobenzyl)oxy]-2-[(2R)-2-methylpiperazin-1-yl]-6,7-dihydro-5H-cyclopenta[b]pyridine;
- (7S)-7-[(2-chloro-5-fluorobenzyl)oxy]-2-[(2R)-2-methylpiperazin-1-yl]-6,7-dihydro-5H-Cyclopenta[b]pyridine;
- (7S)-7-[(2-methyl-5-chorobenzyl)oxy]-2-[(2R)-2-methylpiperazin-1-yl]-6,7-dihydro-5H-cyclopenta[b]pyridine;
- (7S)-7-[(5-fluoro-2-methyl-benzyl)oxy]-2-[(2R)-2-methylpiperazin-1-yl]-6,7-dihydro-5H-cyclopenta[b]pyridine; and
- 4-methyl-3-[({(7S)-2-[(2R)-2-methylpiperazin-1-yl]-6,7-dihydro-5H-cyclopenta[b]pyridin-7-yl}oxy)methyl]benzonitrile;

or a pharmaceutically acceptable salt of said compound.

9. The compound of claim 1 wherein m is 1 and n is 0; or a pharmaceutically acceptable salt of said compound.

10. The compound of claim 9 selected from the group consisting of:
- (7S)-7-(2-chlorophenoxy)-2-piperazin-1-yl-6,7-dihydro-5H-cyclopenta[b]pyridme;
- (7S)-7-(3-chlorophenoxy)-2-piperazin-1-yl-6,7-dihydro-5H-cyclopenta[b]pyridme;
- 3-{[(7S)-2-piperazin-1-yl-6,7-dihydro-5H-cyclopenta[b]pyridin-7-yl]oxy)}benzonitrile;
- 3-{[(7R)-2-piperazin-1-yl-6,7-dihydro-5H-cyclopenta[b]pyridin-7-yl]oxy}benzonitrile; and
- (7R)-7-(3,5-difluorophenoxy)-2-piperazin-1-yl-6,7-dihydro-5H-cyclopenta[b]pyridine;

or a pharmaceutically acceptable salt of said compound.

11. The compound of claim 10 which is 7-(2-chlorophenoxy)-2-[(2R)-2-methylpiperazin-1-yl]-6,7-dihydro-5H-cyclopenta[b]pyridine or a pharmaceutically acceptable salt thereof.

12. The compound of claim 1 wherein m is 2 and n is 0; or a pharmaceutically acceptable salt of said compound.

13. The compound of claim 12 selected from the group consisting of:
- 8-(2-fluorophenoxy)-2-piperazin-1-yl-5,6,7,8-tetrahydro-quinoline;
- (8S)-8-(3-fluorophenoxy)-2-piperazin-1-yl-5,6,7,8-tetrahydroquinoline;
- 3-{[(8R)-2-piperazin-1-yl-5,6,7,8-tetrahydroquinolin-8-yl]oxy}benzonitrile;
- 3-{[(8S)-2-piperazin-1-yl-5,6,7,8-tetrahydroquinolin-8-yl]oxy}benzonitrile;
- (8S)-8-(5-fluoro-2-methyl phenoxy)-2-piperazin-1-yl-5,6,7,8-tetrahydroquinoline;
- (8S)-8-(2-chloro-5-methylphenoxy)-2-piperazin-1-yl-5,6,7,8-tetrahydroquinoline;
- (8S)-8-(3,5-difluorophenoxy)-2-piperazin-1-yl-5,6,7,8-tetrahydroquinoline; and
- (8S)-8-(3-chloro-2-fluorophenoxy)-2-piperazin-1-yl-5,6,7,8-tetrahydroquinoline;

or a pharmaceutically acceptable salt of said compound.

14. The compound of claim 1 wherein $R^3$ is Cl, Br, F, $CH_3$ or CN;

or a pharmaceutically acceptable salt of said compound.

15. The compound of claim 14, selected from the group consisting of:
- 3-Chloro-7(S)-(2,5-difluoro-benzyloxy)-2-(2-(R)-methyl-piperazin-1-yl)-6,7-dihydro-5H-[1]-pyridine;
- 3-Chloro-7-(5-fluoro-2-methyl-benzyloxy)-2-(2-methyl-piperazin-1-yl)-6,7-dihydro-5H-[1]pyridine;
- 3-[3-Chloro-2-(2-methyl-piperazin-1-yl)-6,7-dihydro-5H-[1]pyridin-7-yloxymethyl]-4-methyl-benzonitrile;
- 3-Chloro-8-(2,3-dichloro-phenoxy)-2-piperazin-1-yl-5,6,7,8-tetrahydro-quinoline;
- 3-Chloro-8-(2-fluoro-phenoxy)-2-piperazin-1-yl-5,6,7,8-tetrahydro-quinoline;
- 3-Chloro-8-(5-fluoro-2-methyl-phenoxy)-2-piperazin-1-yl-5,6,7,8-tetrahydro-quinoline;
- 3-Chloro-8-(3,5-difluoro-phenoxy)-2-piperazin-1-yl-5,6,7,8-tetrahydro-quinoline;
- 3-Chloro-8-(3-fluoro-phenoxy)-2-piperazin-1-yl-5,6,7,8-tetrahydro-quinoline;
- 3-Chloro-8-(3-chloro-2-fluoro-phenoxy)-2-piperazin-1-yl-5,6,7,8-tetrahydro-quinoline;
- 3-Chloro-7-(2-chloro-phenoxy)-2-piperazin-1-yl-6,7-dihydro-5H-[1]pyridine; and
- 3-Chloro-7-(3-chloro-phenoxy)-2-piperazin-1-yl-6,7-dihydro-5H-[1]pyridine;

or a pharmaceutically acceptable salt of said compound.

16. The compound of claim 1 wherein $R^1$ is a group of Formula (IA);

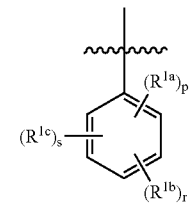

(1A)

where
(i) p, r and s are each independently 0 or 1, and
$R^{1a}$, $R^{1b}$ and $R^{1c}$ are each independently selected from the group consisting of chloro, fluoro, bromo, cyano, —$CH_2$—CN, —$NH_2$, —OH, ($C_1$-$C_4$)alkyl, ($C_1$-$C_4$)alkoxy, ($C_1$-$C_4$)alkylthio, (1-3)fluoro-substituted ($C_1$-$C_4$)alkyl, (1-3)fluoro-substituted ($C_1$-$C_4$)alkoxy, and (1-3)fluoro-substituted ($C_1$-$C_4$)alkylthio;

or a pharmaceutically acceptable salt of said compound.

17. The compound of claim 16 wherein $R^2$ is methyl; $R^{0a}$ is H or $CH_3$; and $R^3$ is H or Cl;

or a pharmaceutically acceptable salt of said compound.

18. The compound of claim 1 wherein
(ii) p and r are each 0; s is 1;
$R^{1c}$ is independently selected from the group consisting of phenyl, phenoxy optionally substituted with F, Cl, Br, or I; benzyl, benzyloxy, —NH($C_1$-$C_4$)alkyl, —N[($C_1$-$C_4$)alkyl]2, —$CH_2$—NH($C_1$-$C_4$)alkyl, —$CH_2$—N[($C_1$-$C_4$)alkyl]$_2$, —NH(phenyl), —NH(5- to 6-membered heteroaryl containing 1 to 3 hetero atoms independently selected from O, N, and S, which is optionally substituted with 1 to 3 halo groups), —N(CH$_3$)—SO2(C$_1$-C$_4$)alkyl, —NH—SO$_2$(C$_1$-C$_4$)alkyl, —NHC(O)NH$_2$, —C(O)—N[(C$_1$-C$_4$)alkyl]$_2$, —C(O)-(5- to 6-membered heterocycle containing 1 to 3 hetero atoms independently selected from O, N, and S), —C(O)—NH(5- to 6-membered heterocycle containing 1 to 3 hetero atoms independently selected from O, N, and S), —C(O)-(5- to 6-membered carbocycle), —CH$_2$—C(O)—O(C$_1$-C$_4$) alkyl, a 3- to 6-membered heterocyclic ring containing 1 to 3 heteroatoms independently selected from O, N or S, and a 5- to 6-membered heteroaryl containing 1 to 3 heteroaroms independently selected from O, N or S which is optionally substituted with one to three substituents independently selected from F, Cl, Br, I, and —CF$_3$; or a pharmaceutically acceptable salt of said compound.

19. The compound of claim 1 wherein R$^1$ is a 5- to 6-membered heteroaryl which is pyridyl or pyrimidinyl, where said pyridyl and said pyrimidinyl are optionally substituted with cyano, F, Cl, Br, I, methyl, methoxy or —C(O)OCH$_3$; or a pharmaceutically acceptable salt of said compound.

20. The compound selected from the group consisting of: compounds of the formula

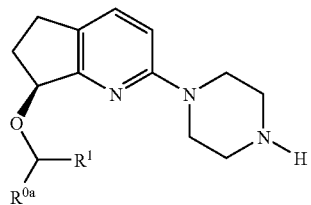

wherein
R$^{oa}$ is H and R$^1$ is 2-ethyl-phenyl, phenyl, naphthalen-1-yl, quinotin-5-yl, quinolin-8-yl, 2-chloro-phenyl, 3-chlorophenyl, 2-fluoro-phenyl, 3-fluoro-phenyl, 3-bromo-phenyl, 2-methyl-phenyl, 3-methyl-phenyl, 2-isopropylphenyl, 2-trifluoromethyl-phenyl, 3-trifluoromethyphenyl, 2-cyano-phenyl, 3-cyano-phenyl, 2-trifluoromethoxy-phenyl, 3-trifluoromethoxy-phenyl, fluoromethyl)-phenyl, 3-(2-fluoromethyl)-phenyl, 3-phenoxy-phenyl, 3-benzyloxy-phenyl, fluorophenoxy)-phenyl, 3-(triftuoromethyl-thio)-phenyl, biphenyl-2-yl, 4'-(trifluoromethyl)biphenyl-2-yl, 3-(6-bromo-2-chloro-pyrimidin4-amino)-phenyl, 4-(N-methyl(methanesulfon-amido))-phenyl, 2-(2,2,2-trifluoroacetamido)-phenyl, pyrazol-1-yl-phenyl, [1,2,4]triazol-1-yl-phenyl, 3-benzamido, 3-(N-methylbenzamido), 2,4-difluorophenyl, 2,3-difluorophenyl, 2,5-difluorophenyl, 3,5-difluorophenyl, 2,6-difluorophenyl, 2,5-dichlorophenyl, 2,6-dichlorophenyl, 2,3-dichlorophenyl, 2-chloro-6-fluorophenyl, 3-chloro-2-fluorophenyl, 2,3-dimethylphenyl, 2,6-dimethylphenyl, 3,5-dimethylphenyl, 3,5-bis-trifluoromethylphenyl, 2,5-bis-trifluoromethyl-phenyl, 3,5-dimethoxyphenyl, 2,3-dimethoxyphenyl, 3-fluoro-5-methylphenyl, 2-fluoro-3-methylphenyl, 5-fluoro-2-methylphenyl, 3-fluoro-2-methylphenyl, 5-chloro-2-methylphenyl, 5-fluoro-2-trifluoromethyl-phenyl, 2-fluoro-6-trifluoromethyl-phenyl, 2-fluoro-3-triftuoromethyl-phenyl, 3-fluoro-2-trifluoromethyl-phenyl, 2-chloro-5-trifluoromethyl-phenyl, 2-chloro-5-methoxy-phenyl, 2-methoxy-5-acetyl-phenyl, 4'-chloro-4-methoxy-biphenyl, 2,3,5-trifluorophenyl, 2-chloro-3,6-difluorophenyl, 2-ethyl-3,5-difluorophenyl, 2-methyl-3,5-difluorophenyl, 6-fluoro-4H-benzo[1,3]dioxin-8-yl, 6,7-dichloro-4H-benzo[1,3]-dioxin-8-yl, pyridin-3-yl, pyridin-6-yl, 3,5-dimethyl-isoxazol-4-yl, 6-chloro-pyridin-3-yl, 3-methyl-pyridin-2-yl, or 3-(N-morpholin-4-yl -benzamido);
R$^{oa}$ is CH$_3$ and R$^1$ is 2-chlorophenyl, 3-chlorophenyl, 2-fluorophenyl, 3-fluorophenyl, 2-methylphenyl, 3-methylphenyl; or
R$^{oa}$ is CH$_3$ having an (S) or an (R) configuration and R$^1$ is 2-chlorophenyl;

compounds of the formula

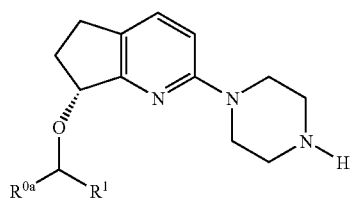

wherein
R$^{oa}$ is CH$_3$ and R$^1$ 3-chlorophenyl or 2-chlorophenyl; and compounds of the formula

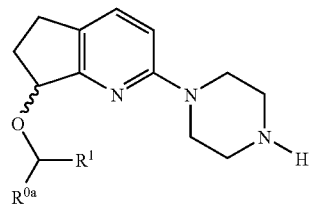

wherein
R$^{oa}$ is H and R$^1$ is 2-chloro-phenyl, 3-chloro-phenyl, 4-chloro-phenyl, 2-fluoro-phenyl, 2-bromo-phenyl, 2-cyano-phenyl, 3-cyano-phenyl, 4-cyano-phenyl, or 2-methoxy-phenyl;
or a pharmaceutically acceptable salt of said compound.

21. The compound of claim 1 having the formula

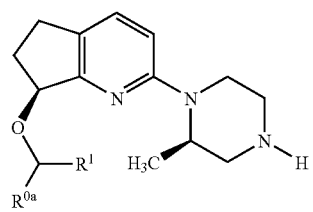

wherein
R$^{oa}$ is H; and R$^1$ is 3-fluorophenyl, 2-chlorophenyl, 2-cyanophenyl, 3-cyanophenyl, 2-trifluoromethyl-phenyl, 2,5-difluorophenyl, 2,5-dichiorophenyl, 2-chloro-5-fluorophenyl, 5-fluoro-2-methylphenyl, 5-chloro-2-methylphenyl, 2-fluoro-5-trifluoromethyl-phenyl, 5-fluoro-2-trifluoromethyl-phenyl, 2-chloro-5-trifluoromethyl-phenyl, 2-fluorophenyl, 3-chiorophenyl, 2-fluoro-5-chlorophenyl, 2-fluoro-5-cyanohenyl, or 2-methyl-5-cyanophenyl;
or a pharmaceutically acceptable salt of said compound.

22. The compound of claim 1 selected from the group consisting of:

compounds of the formula

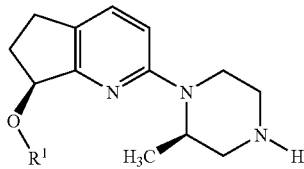

wherein

R¹ is 2,3-dichlorophenyl, 2-chlorophenyl, 3-chlorophenyl, 2-fluorophenyl, 3-fluorophenyl, 2-methylphenyl, 3-methylphenyl, 2-trifluoromethylphenyl, 2-cyanophenyl, 3-cyanophenyl, 3,5-difluorophenyl, 2,5-difluorophenyl, 2,3-difluorophenyl, 2,5-dimethylphenyl, 2-fluoro-5-methylphenyl, 5-fluoro-2-methylphenyl, isoquinolin-8-yl, 2-methyl-quinolin-8-yl, indan-4-yl, 6-fluoro-indan-4-yl, or 6-methyl-pyridin-2-yl;

compounds of the formula

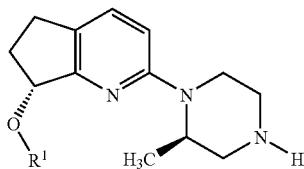

wherein

R¹ is 2-chlorophenyl, 3-chlorophenyl, 2-fluorophenyl, 3-fluorophenyl, 2-methylphenyl, 3-methylphenyl, 2-trifluoromethylphenyl, 2-cyanophenyl, 3-cyanophenyl, 2,5-difluorophenyl, 3,5-difluorophyenyl, 2,3-difluorophenyl, 5-fluoro-2-methylphenyl, 2-fluoro-5-methylphenyl, 2-chloro-5-methylphenyl, or 6-methyl-pyridin-2-yl; and a compound of the formula

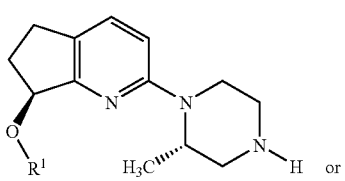

or

-continued

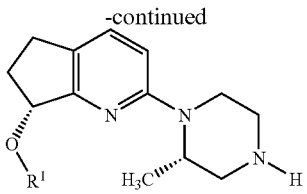

wherein

R¹ is 2-chlorophenyl;

or a pharmaceutically acceptable salt of said compound.

23. The compound (7S)-7-[(5-fluoro-2-methyl-benzyl)oxy]-2-[(2R)-2-methylpiperazin-1-yl]-6,7-dihydro-5H-cyclopenta[b]pyridine or a pharmaceutically acceptable salt thereof.

24. The compound (7R)-7-(3,5-difluorophenoxy)-2-piperazin-1-yl-6,7-dihydro-5H-cyclopenta[b]pyridine or a pharmaceutically acceptable salt thereof.

25. The compound 3-Chloro-8-(5-fluoro-2-methyl-phenoxy)-2-piperazin-1-yl-5,6,7,8-tetrahydro-quinoline or a pharmaceutically acceptable salt thereof.

26. A pharmaceutical composition comprising
(a) a compound or a pharmaceutically acceptable salt thereof according to claim 1; and
(b) a pharmaceutically acceptable carrier.

27. A method for treating a disease, condition, or disorder in a mammal, comprising administering to said mammal a therapeutically effective amount of a compound of claim 1, or a pharmaceutically acceptable salt thereof, wherein the disease, condition or disorder is selected from the group consisting of, weight loss or control, obesity, depression, atypical depression, anxiety, epilepsy, and lower urinary tract dysfunction.

28. The method of claim 27 wherein the disease, condition or disorder is selected from the group consisting of anxiety.

29. The method of claim 27 wherein the disease, condition or disorder is selected from the group consisting of, weight loss or control, or obesity.

30. The method of claim 27 comprising administering to said mammal a therapeutically effective amount of a compound of claim 1, a pharmaceutically acceptable salt thereof, and an additional pharmaceutically active agent.

31. The method of claim 29 wherein the disease, condition or disorder is a weight loss or control condition selected from the group consisting of reduction in calorie or food intake, and/or appetite suppression.

32. The method of claim 29 wherein the disease, condition or disorder is obesity.

33. The method of claim 27 wherein the disease, condition or disorder is a lower urinary tract dysfunction.

34. The method of claim 27 wherein the disease, condition or disorder is urinary incontinence.

* * * * *